(12) United States Patent
Ke et al.

(10) Patent No.: US 12,415,830 B2
(45) Date of Patent: Sep. 16, 2025

(54) STEROID COMPOUND, AND USE THEREOF AND PREPARATION METHOD THEREFOR

(71) Applicant: Chengdu Kanghong Pharmaceutical Co Ltd, Chengdu (CN)

(72) Inventors: Xiao Ke, Chengdu (CN); Yiqian Wang, Chengdu (CN); Pei Chen, Chengdu (CN)

(73) Assignee: Chengdu Kanghong Pharmaceutical Co Ltd, Chengdu (CN)

( * ) Notice: Subject to any disclaimer, the term of this patent is extended or adjusted under 35 U.S.C. 154(b) by 1011 days.

(21) Appl. No.: 17/421,336

(22) PCT Filed: Jan. 7, 2020

(86) PCT No.: PCT/CN2020/070755
§ 371 (c)(1),
(2) Date: Jul. 7, 2021

(87) PCT Pub. No.: WO2020/143640
PCT Pub. Date: Jul. 16, 2020

(65) Prior Publication Data
US 2022/0089637 A1     Mar. 24, 2022

(30) Foreign Application Priority Data

Jan. 8, 2019    (CN) .......................... 201910017373.2

(51) Int. Cl.
*C07J 63/00*    (2006.01)

(52) U.S. Cl.
CPC .................................. *C07J 63/008* (2013.01)

(58) Field of Classification Search
CPC .................................................... C07J 63/008
USPC ......................................................... 514/176
See application file for complete search history.

(56) References Cited

U.S. PATENT DOCUMENTS

| | | | |
|---|---|---|---|
| 4,045,574 A | 8/1977 | Kerb et al. | |
| 4,056,633 A | 11/1977 | Kerb et al. | |
| 5,939,545 A | 8/1999 | Upasani et al. | |
| 2009/0131503 A1 | 5/2009 | Annedi | |
| 2009/0221611 A1 | 9/2009 | Devita | |
| 2017/0240589 A1 | 8/2017 | Martinez Botella | |
| 2021/0139530 A1 | 5/2021 | Su et al. | |
| 2022/0315621 A1* | 10/2022 | Robichaud | ............... C07J 61/00 |

FOREIGN PATENT DOCUMENTS

| | | |
|---|---|---|
| CN | 1190404 A | 8/1998 |
| CN | 101784558 A | 7/2010 |
| CN | 103958540 A | 7/2014 |
| CN | 105339381 A | 2/2016 |
| CN | 106432380 A | 2/2017 |
| DE | 2360443 A | 6/1975 |
| DE | 2461312 A | 6/1976 |
| EP | 2842955 A1 | 3/2015 |
| EP | 3750808 A1 | 12/2020 |
| EP | 3750908 A1 | 12/2020 |
| RU | 2458065 C2 | 8/2012 |
| RU | 2020123930 A | 1/2022 |
| RU | 2020126096 A | 3/2022 |
| WO | 199521617 A1 | 8/1995 |
| WO | 199805337 A1 | 2/1998 |
| WO | 2008063128 A1 | 5/2008 |
| WO | 2014169833 A1 | 10/2014 |
| WO | 2016061527 A1 | 4/2016 |
| WO | 2019126761 A1 | 6/2019 |
| WO | 2019154247 A1 | 8/2019 |
| WO | 2019154257 A1 | 8/2019 |
| WO | 2020264512 A1 | 12/2020 |

OTHER PUBLICATIONS

International Search Report and Written Opinion, mailed on Apr. 8, 2020, for PCT Application No. PCT/CN2020/070755, filed on Jan. 7, 2020, 11 pages.
Bastin, R.J. et al. (Jan. 1, 2000, e-Jul. 19, 2000. "Salt Selections and Optimisation for Pharmaceutical New Chemical Entities," Organic Process Research and Development 4(5):427-435.
Belikov, V.G. (2007). "Pharmaceutical Chemistry," Textbook, Ed. Fourth, Moscow: Medpress-Inform, 622 P., 11, 27-29, 12 pages. Machine Translation.
Gavrilov, A.S. (2010). Pharmaceutical Technology. Manufacture Of Medicines, Textbook, Moscow: Geotar-Media Publishing Group, 624, p. 20. 6 pages. Machine Translation.
Khan, R.S. et al. (2018). "Biomarker Detection of Neurological Disorders Through Spectroscopy Analysis," International Dental & Medical Journal Of Advanced Research 4:1-9.
Novosibirsk. (2016). "Concept And Types of Medical Prevention. Forms And Methods of Carrying Out Various Types Of Prevention," Fundamentals of Medical Prevention. Educational And Methodological Manual for Students and Cadets of Advanced Training Cycles of State Professional Educational Institutions, Novosibirsk 206, p. 13-21, 19 pages total. Machine Translation.
International Preliminary Report on Patentablity, issued on Jun. 16, 2021, for PCT Application No. PCT/CN2020/070755, filed on Jan. 7, 2020, 16 pages, with English Translation.
Belikov V.G. (1993). "Relation Between the Molecular Structure of Compounds and their Action on an Organism," Pharmaceutical Chemistry pp. 43-47, 10 pages with English translation.
Dyson, G. et al. (1964). "Introduction. The Mechanism of Action of Medicinal Substances," Chapter 1 in Chemistry of Synthetic Drugs, Translated English. MIR, pp. 12-19, 20 pages.
Aird, R.B. et al. (Mar. 10, 1951). "Anticonvulsive Properties of Desoxycorticosterone," J. Amer. Med. Soc. 145(10):715-719.
Backstrom, T. et al. (1985). "Ovarian Steroid Hormones Effects on Mood, Behavior and Brain Excitability," Acta Obstet. Gynecol. Scand. Suppl. 130:19-24.

(Continued)

Primary Examiner — Kristin A Vajda
(74) Attorney, Agent, or Firm — MORRISON & FOERSTER LLP

(57) ABSTRACT

The present invention relates to a steroid compound, a use thereof and a preparation method therefor. It is expected that such compound can effectively treat mental and neurological diseases, and has good active efficacy, pharmacokinetic (PK) performance, oral bioavailability, stability, safety, clearance rate, and/or metabolic performance and the like.

13 Claims, 1 Drawing Sheet

(56) References Cited

OTHER PUBLICATIONS

Berge, S.M et al. (Jan. 1977). "Pharmaceuticals Salts," J. Pharmaceutical Sciences 66(1):1-19.

Brighton, S.W. et al. (1987). "The Effect of an Oral Gold Preparation on the Gastrointestinal Tract Motility in Two Species of Experimental Animals," Journal of Pharmacological Methods 17:185-188.

European Search Report and Search Opinion mailed on Oct. 12, 2022, for European Patent Application No. 20738082.5, filed on Jan. 1, 2020, 14 pages.

Glykys, J. et al. (Dec. 6, 2007). "Activation Of GABAA Receptors: Views From The Outside The Synaptic Cleft," Neuron, 56:763-770.

Gyermek, L. et al. (Jan. 1, 1968). "Steroids. CCCX. Structure-Activity Relation off Some Steroidal Hypnotic Agents," J. Med. Chem. 11:117-125.

Harrison, N.L. et al. (1987). "Structure-Activity Relationships for Steroid Interaction With The Gamma-Aminobutyric Acida Receptor Complex," J. Pharmacol. Exp. Ther. 241(1):346-353.

Hosie, A.M. et al. (Nov. 23, 2006, E-PUB. Nov. 15, 2006). "Endogenous Neurosteroids Regulate GABAA Receptors Through Two Discrete Transmembrane Sites," Nature 444(7818):486-489.

Kudova, E. et al. (Jul. 14, 2015). "A New Class of Potent N-Methyl-D-Aspartate Receptor Inhibitors: Sulfated Neuroactive Steroids With Lipophilic D-Ring Modifications," Journal of Medicinal Chemistry 58(15):5950-5966.

Laidlaw, J. et al. (Dec. 15, 1956). "Catamenial Epilepsy," The Lancet 268(6955)1235-1237.

Lambert, J. et al. (Jun. 1987). "Actions of Synthetic and Endogenous Steroids on The Gabaa Receptor," Trends Pharmacol. Sci. 8:224-227.

Lan, N.C. et al. (1991). "Identification And Characterization of A Pregnane Steroid Recognition Site That Is Functionally Coupled To An Expressed GabaA Receptor," Neurochem. Res. 16(3):347-356.

Majewska, M.D. et al. (May 23, 1986). "Steroid Hormone Metabolites Are Barbiturate-Like Modulators of the GABA Receptor," Science 232:1004-1007.

Pfaff, D.W. et al. (Feb. 18, 1983). "Actions of Estrogens and Progestins on Nerve Cells," Science 219:808-814.

Rosciszewska, D. et al. (Jan. 1986). "Ovarian Hormones, Anticonvulsant Drugs, And Seizures During the Menstrual Cycle In Women With Epilepsy," J. Neurol. Neurosurgery. Psychiatry 49:47-51.

Wang, J. et al. (2009). "Current Situation and Recommendations of Mental Health Services in China," China Health Service Management 5:348-350. (English Translation of the Abstract).

\* cited by examiner

STEROID COMPOUND, AND USE THEREOF AND PREPARATION METHOD THEREFOR

CROSS REFERENCE TO RELATED APPLICATIONS

This application is a national stage application under 35 U.S.C. § 371 of International Application No. PCT/CN2020/070755, filed internationally on Jan. 7, 2020 which claims the benefit of Chinese Application No. 201910017373.2 filed on Jan. 8, 2019, the entire contents of which are hereby incorporated herein by reference in their entirety.

FIELD OF THE INVENTION

The present invention relates to the pharmaceutical area, in particular to steroid compounds, applications and preparation methods therefore.

BACKGROUND OF THE INVENTION

Neuropsychiatric diseases include anxiety, depression, schizophrenia and so on, ranking first in the total burden of diseases in China, accounting for about 20% of the total diseases (Wang Juncheng et al., China Health Service Management, 2009 (5): 348-350). With the continuous social modernization, the accelerated working rhythm and the increased living pressure, the number of patients with various neuropsychiatric diseases has increased dramatically, and the progression of symptoms has accelerated significantly, making it more urgent to develop, research and produce new drugs for the treatment of these diseases. Meanwhile, clinical data suggests that many patients are troubled by a variety of neuropsychiatric disorders at the same time. The high comorbidity of neuropsychiatric diseases makes clinical treatment face greater challenges.

In animals, GABA (gamma-aminobutyric acid) γ-aminobutyric acid) only exists in nerve tissues and immunological studies have shown that the highest concentration of GABA is found in the substantia nigra. GABA is an important inhibitory neurotransmitter that has been studied in depth. It participates in a variety of metabolic activities and has high physiological. The GABA system is the main inhibitory signal pathway of the brain and central nervous system, which is of great significance for the function of the central nervous system. GABA(A) receptor (GARBAAR) is an ionic receptor and ligand-gated ion channel. Its endogenous ligand γ-aminobutyric acid (GABA), the main inhibitory neurotransmitter is in the central nervous system. After the GABA(A) receptor activation, extracellular Cl⁻ is selectively allowed to pass through the pores of the GABA receptors. Cl⁻ flows out of the neuron cells when the internal potential is less than the resting potential, and flows into the neuron cells when the internal potential is greater than the resting potential (i.e., −75 mv). This can successfully reduce the chance of action potentials, and inhibit neurotransmission. Anxiety and depression have extremely high comorbidities and are considered to have overlapping and co-occurring phenomena. Anxiety and depression are also important emotional symptoms of schizophrenia. Research results confirm that GABAergic system and GABA(A) receptor play an important role in the etiology and pathology of these three diseases, indicating that a pathophysiological process related to the GABAergic system may be one of the decisive factors for all three diseases. The GABAergic system and GABA(A) receptor have been shown to be involved in the pathological processes of anxiety, depression and schizophrenia at the molecular level, pre-clinical and clinical lever, and the GABA(A) receptor has long been used as an important drug target in the treatment for these diseases.

It was confirmed by clinical trials that in addition to binding to GABA itself, forming receptor complex (GRC) to change brain excitability, the GABA(A) receptor can bind to other small molecule compounds, such as barbiturates (trade name Secobarbital Sodium), benzodiazepine (trade name diazepam), etc. These drugs bind to specific allosteric sites on the GABA(A) receptor, respectively, and produce their therapeutic effects. Furthermore, studies have shown that there are unique binding sites on the GABA(A) receptor for steroid compounds (Lan, N C et al., Neurochem. Res. 16:347-356 (1991)).

Neuroactive steroids can occur endogenously. The most potent endogenous neuroactive steroids are 3α-hydroxy-5-reduced pregnan-20-one and 3α-21-dihydroxy-5-reduced pregnan-20-one, metabolites of hormonal steroids progesterone and deoxycorticosterone, respectively. The ability of these steroid metabolites to alter brain excitability was recognized in 1986 (Majewska, M. D. et al., Science 232: 1004-1007 (1986); Harrison, N. L. et al., J. Pharmacol. Exp. Ther. 241:346-353 (1987)). The ovarian hormone progesterone and its metabolites have been demonstrated to have profound effects on brain excitability (Backstrom, T. et al, Acta Obstet. Gynecol. Scand. Suppl. 130:19-24 (1985); Pfaff, D. W and McEwen, B. S., Science 219:808-814 (1983); Gyermek et al, J Med Chem. 11:117 (1968); Lambert, J. et al, Trends Pharmacol. Sci. 8:224-227 (1987)). The levels of progesterone and its metabolites vary with the phases of the menstrual cycle. It has been well documented that the levels of progesterone and its metabolites decrease before menstruation begins. The monthly recurrence of certain physical symptoms prior to the onset of menstruation has also been well documented. These symptoms, which have become associated with premenstrual syndrome (PMS), include stress (tension), anxiety, and migraine headaches (Dalton, K., Premenstrual Syndrome and Progesterone Therapy, 2nd edition, Chicago Yearbook, Chicago (1984)). Subjects with PMS have symptoms that recur once a month and are present pre-menstruation and absent post-menstruation.

Other studies have found that a reduction in progesterone is associated with an increase in seizure frequency in female patients with epilepsy (Laidlaw, J., Lancet, 1235-1237 (1956)). A more direct correlation has been observed with a reduction in progesterone metabolites (Rosciszewska et al, J. Neurol. Neurosurg. Psych. 49:47-51 (1986)). In addition, for subjects with primary generalized petit mal epilepsy, the temporal incidence of seizures has been correlated with the incidence of the symptoms of premenstrual syndrome (Backstrom, T. et al, J. Psychosom. Obstet. Gynaecol. 2:8-20 (1983)). The steroid deoxycorticosterone has been found to be effective in treating subjects with epileptic spells correlated with their menstrual cycles (Aird, R B. and Gordan, G, J. Amer. Med. Soc. 145:715-719 (1951)).

A syndrome also related to low progesterone levels is postpartum depression (PPD). Immediately after birth, progesterone levels decrease dramatically leading to the onset of PPD. The symptoms of PPD range from mild depression to psychosis requiring hospitalization. PPD is also associated with severe anxiety and irritability. PPD is not amenable to treatment by classic antidepressants, and women experiencing PPD show an increased incidence of PMS (Dalton, K., Premenstrual Syndrome and Progesterone Therapy, 2nd edition, Chicago Yearbook, Chicago (1984)).

Collectively, these observations imply a crucial role for progesterone and deoxycorticosterone and more specifically their metabolites in the homeostatic regulation of brain excitability, which is manifested as an increase in seizure activity or symptoms associated with catamenial epilepsy, PMS, and PPD.

Many studies are based on GABA(A) receptors in order to obtain drugs that can effectively treat related diseases. CN103958540A, CN10533928A, etc. have disclosed a series of neurological steroid compounds for the treatment of neuropsychiatric diseases. GABA(A): a subtype of γ-aminobutyric acid receptor (GABA R), GARA R has three subtypes, including GABA(A). GABA(B) and GABA(C). GABA(A) is a chloride ion channel.

The GABA(A) is composed of five subunits (polypeptide chain) to form a heteropentameric structure. Among the five subunits, two pairs are the same, so a specific GABA(A) receptor contains three types of subunits, commonly known as α, β and γ. Each subunit has several different subtypes, such as α has $\alpha_1, \alpha_2, \alpha_3, \alpha_4, \alpha_5, \alpha_6$, β has $\beta_1, \beta_2, \beta_3$, γ has $\gamma_1, \gamma_2, \gamma_3, \gamma_4$. Furthermore, there are subunits such as δ, ε, $\rho_{1-3}$, θ, π, etc., which can form pentamers with α and β.

According to statistics, there are a total of 23 GABA(A) receptors with different combinations of subunits. The specific isoform of the receptors are related to the distribution area of neurons in the brain. For example, the GABA(A) receptors containing γ-subunit are mainly located inside the synapses, while the GABA(A) receptors containing δ-subunit are mainly distributed outside the synapses (extrasynaptic). (Activation of GABA(A) Receptors: Views from Outside the Synaptic Cleft, Neuron, Vol 56, 2007, 763-770); Study (Endogenous neurosteroids regulate GABA(A) receptors through two discrete transmembrane sites: Nature. Vol 444.23 November. 2006.486-489) has showed that endogenous steroids such as tetrahydrodeoxycorticosterone (THDOC) can directly activate the GABA receptor $\alpha_1\beta_2\gamma_2$ in the synapses (hereinafter referred as $GABA_{A1}$) at high concentration (micro-molar level), while potentiating the GABA receptor $\alpha_1\beta_2\gamma_2$ at lower concentration (submicromolar level).

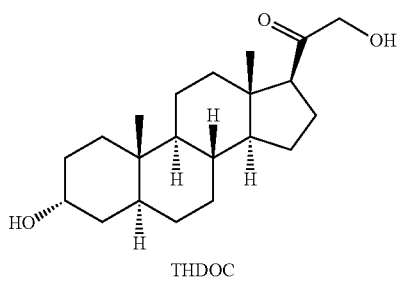

THDOC

However, there are no reports about steroid compounds that can directly activatereceptor subtypes outside the synapses (such as $\alpha_4\beta_3\delta$, hereinafter referred as $GABA_{A4}$).

SUMMARY OF THE INVENTION

One of the purposes of the invention is to provide steroid compounds which can treat neurological diseases more effectively. Compounds of the invention are expected to provide good potency, pharmacokinetic (PK) properties, oral bioavailability, formulatability, stability, safety, clearance and/or metabolism, and reduce side effects, like anesthesia and sedation.

In view of the above purposes, the invention provides a compound of Formula (I) or a pharmaceutically acceptable salt thereof:

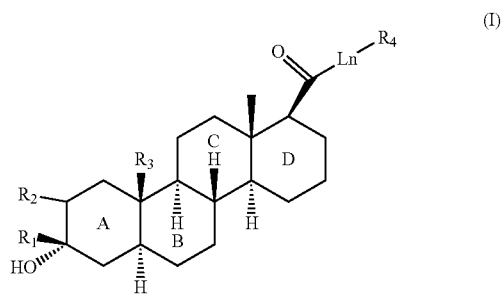

wherein R1 is hydrogen, substituted or unsubstituted C1-6 alkyl, substituted or unsubstituted C1-6 alkoxy, substituted or unsubstituted C2-6 alkenyl, substituted or unsubstituted C2-6 alkynyl, or substituted or unsubstituted C3-6 carbocyclyl; R2 is hydrogen, halogen, substituted or unsubstituted C1-6 alkyl, substituted or unsubstituted C1-6 alkoxy, substituted or unsubstituted C2-6 alkenyl, substituted or unsubstituted C2-6 alkynyl, substituted or unsubstituted C3-6 carbocyclyl; R3 is hydrogen, unsubstituted C1-6 alkyl or —CH$_2$OR$^a$, wherein R$^a$ is hydrogen, substituted or unsubstituted C1-6 alkyl, substituted or unsubstituted C1-6 alkoxy, substituted or unsubstituted C2-6 alkenyl, substituted or unsubstituted C2-6 alkynyl, substituted or unsubstituted C3-6 carbocyclyl;

L is —C(Rb)(Rb)-, each Rb is independently hydrogen or C1-C6 alkyl, n is an integer of 0 to 3;

R4 is halogen or substituted or unsubstituted heteroaryl or heterocyclyl.

Further preferred compounds, wherein R1 is hydrogen, substituted or unsubstituted C1-6 alkyl; R2 is hydrogen, substituted or unsubstituted C1-6 alkyl; R3 is hydrogen, an unsubstituted C1-6 alkyl; Rb is hydrogen, n is an integer of 1 to 2; R4 is heteroaryl, optionally substituted with cyano, nitro, hydroxy, halo, C1-C6 alkyl, C1-C6 alkoxy, C1-C6 haloalkyl, —C(O)Rd, —C(O)N(Re)(Rf), —C(O)O(Rd), —N(Re)(Rf), —OC(O)N(Re)(Rf), —OC(O)O(Rd), —OC(O)Rd, —S(O)$_{0-2}$Rd, —S(O)$_{0-2}$ORd or —S(O)$_{0-2}$N(Re)(Rf); each Rd is independently hydrogen or C1-C6 alkyl; each Re and Rf is independently hydrogen, C1-C6 alkyl, carbocyclyl, heterocyclyl, aryl, heteroaryl.

Further preferred compounds, wherein R1 is hydrogen or methyl; R2 is hydrogen; R3 is hydrogen; L is —CH$_2$—; R4 is a monocyclic or bicyclic-heteroaryl or a monocyclic or bicyclic-heterocyclyl, each heteroatom is oxygen or nitrogen or sulfur, the bicyclic ring can be spiro or fused.

Further preferred compounds, R4 is a five- or six-membered heteroaryl containing 2-4 nitrogen atoms and optionally substituted with cyano, nitro, hydroxy, halo, C1-C6 alkyl, C1-C6 alkoxy, C1-C6 haloalkyl.

Or as shown in the compound of formula II:

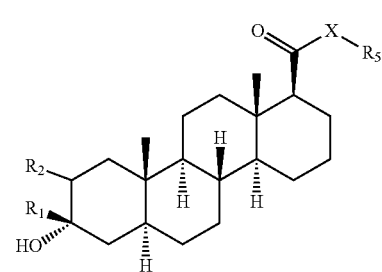

wherein $R^1$ is hydrogen, or C1-3 alkyl group substituted or unsubstituted with halogen; R2 is hydrogen, halogen, C1-6 alkyl group substituted or unsubstituted with halogen or C1-6 alkoxy group substituted or unsubstituted with halogen; X is $CH_2$, N, O or S; R5 is selected from the following groups:

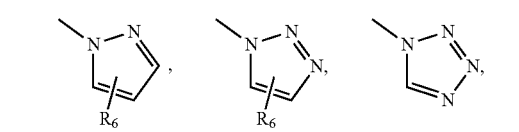

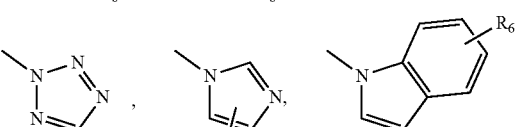

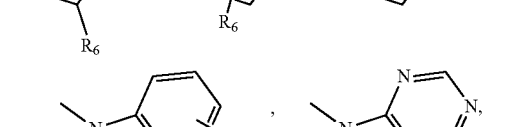

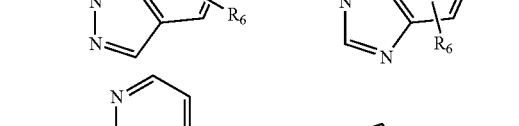

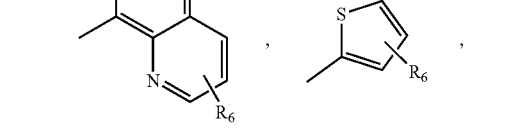

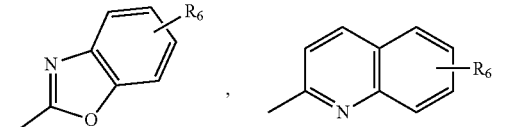

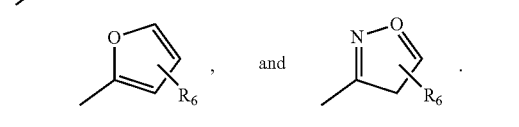

wherein $R^6$ is H, halogen, CN, CF3, NO2, C1-6 alkyl substituted or unsubstituted with halogen or C1-6 alkoxy substituted or unsubstituted with halogen.

Alternatively, the preferred compound is selected from:

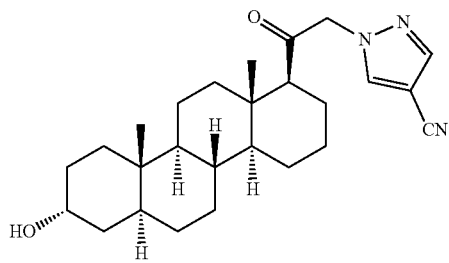

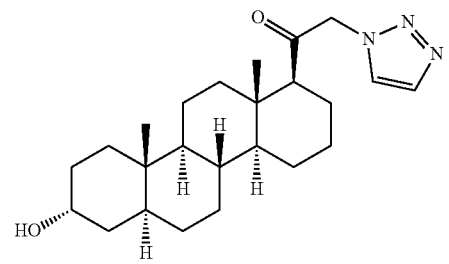

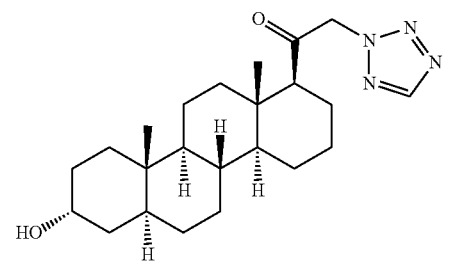

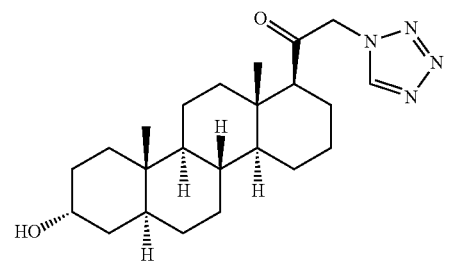

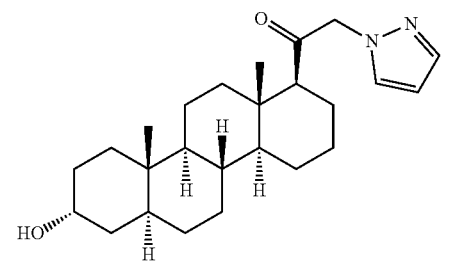

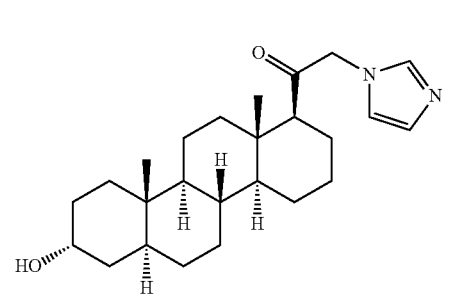

-continued
| 7 | 8 |
|---|---|
| 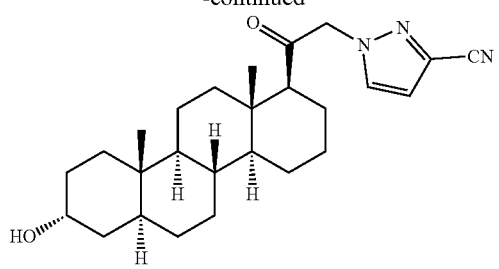 | 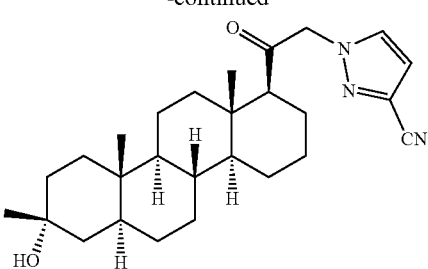 |
| 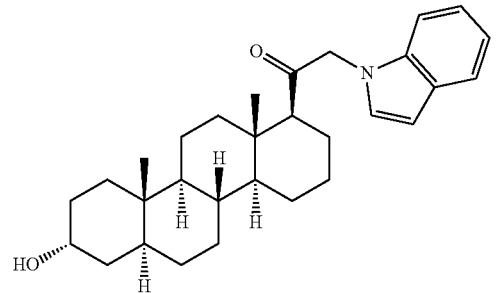 | 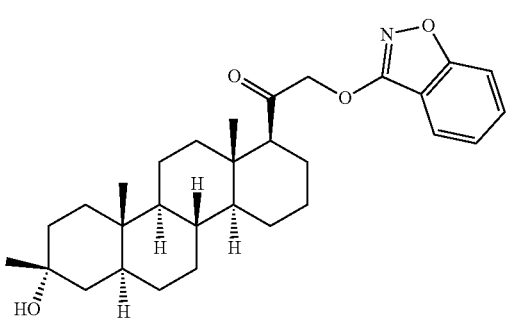 |
| 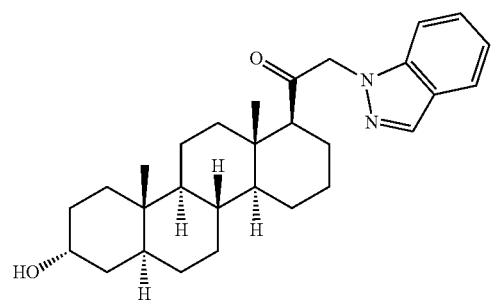 | 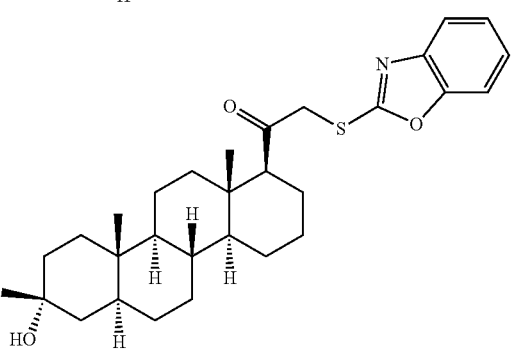 |
| 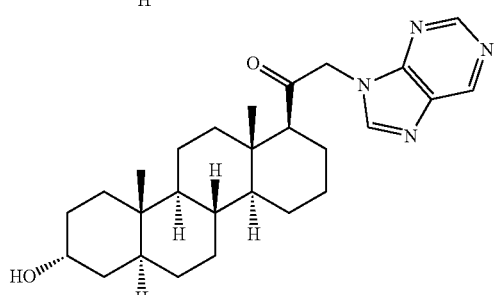 | 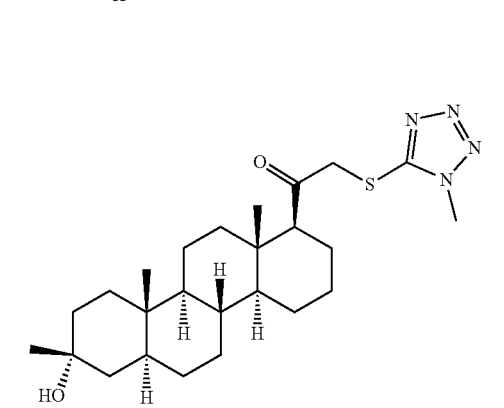 |
| 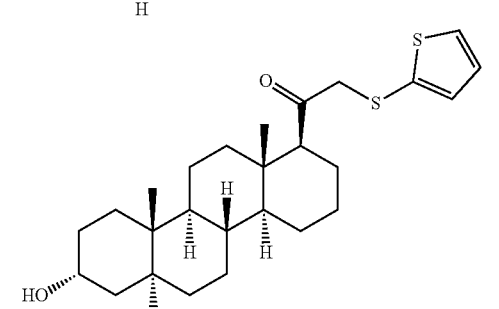 | 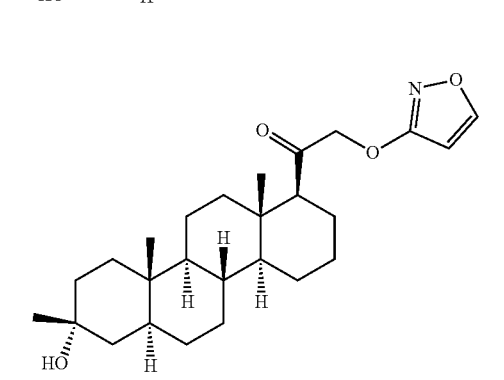 |
| 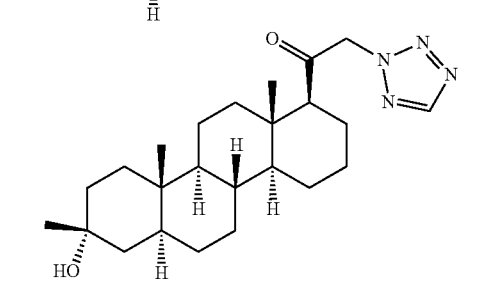 | |

-continued

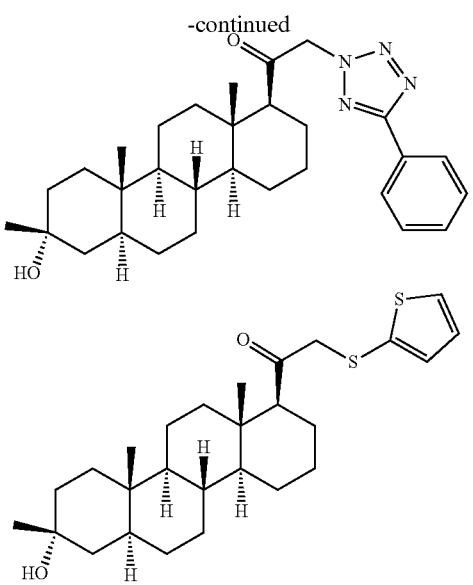

The present invention also provides pharmaceutical compositions, comprising any of the above compounds or pharmaceutically acceptable salts thereof, or pharmaceutically acceptable excipients.

The present invention also provides compounds described herein which can act as GABA modulators, such as positively or negatively effecting GABA(A) receptors. As modulators of the excitability of central nervous system (CNS), such compounds are expected to have CNS-activity by their ability to modulate GABA(A) receptors.

The present invention further provides the application of compounds described herein or the pharmaceutical compositions in preventing or treating neurological diseases; wherein the neurological disease is preferably selected from a sleep disorder, a mood disorder, a schizophrenia spectrum disorder, a spasmodic disorder, a memory and/or cognitive disorder, a movement disorder, a personality disorder, an autism spectrum disorder, pain, traumatic brain injury, a vascular disease, a substance abuse disorder and/or withdrawal syndrome or tinnitus; wherein the mood disorder is depression; wherein the depression is destructive mood disorder, severe depressive disorder, persistent depressive disorder, premenstrual dysphoria, substance or drug-induced disorder, disorder due to physical diseases, other specific depressive disorder and nonspecific depressive disorder, preferably mild depression, moderate depression, severe depression or postpartum depression. Preferably severe depression or postpartum depression. And the above compounds or pharmaceutical compositions can be administered orally, subcutaneously, intravenously or intramuscularly.

Definition

Chemical Definition

Compounds described herein may include one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses.

The following terms are intended to have the following meanings provided therewith, and are useful in understanding the description and the intended scope of the present invention. When describing the present invention, it may include compounds, pharmaceutical compositions containing the compounds, and the compounds and compositions of the test method. For definitions of terms involved in the present invention, reference may be made to the following description, any part defined below may be substituted with many substituents, and the corresponding definitions are within their scope listed below, including such substituted parts. Unless otherwise specified, the term "substituted" is as defined below.

"Alkyl" refers to a straight-chain or branched saturated hydrocarbon group having from 1 to 20 carbon atoms ("C1-20 alkyl"). In some embodiments, an alkyl group has 1 to 12 carbon atoms ("C1-12 alkyl"). In some embodiments, an alkyl group has 1 to 10 carbon atoms ("C1-10 alkyl"). In some embodiments, an alkyl group has 1 to 9 carbon atoms ("C1-9 alkyl"). In some embodiments, an alkyl group has 1 to 8 carbon atoms ("C1-8 alkyl"). In some embodiments, an alkyl group has 1 to 7 carbon atoms ("C1-7 alkyl"). In some embodiments, an alkyl group has 1 to 6 carbon atoms ("C1-6 alkyl", also referred to herein as "lower alkyl"). In some embodiments, an alkyl group has 1 to 5 carbon atoms ("C1-5 alkyl"). In some embodiments, an alkyl group has 1 to 4 carbon atoms ("C1-4 alkyl"). In some embodiments, an alkyl group has 1 to 3 carbon atoms ("C1-3 alkyl"). In some embodiments, an alkyl group has 1 to 2 carbon atoms ("C1-2 alkyl"). In some embodiments, an alkyl group has 1 carbon atom ("C1 alkyl"). In some embodiments, an alkyl group has 2 to 6 carbon atoms ("C2-6 alkyl"). Examples of C1-6 alkyl group include methyl (C1), ethyl (C2), n-propyl (C3), isopropyl (C3), n-butyl (C4), tert-butyl (C4), sec-butyl (C4), iso-butyl (C4), n-pentyl (C5), 3-pentanyl (C5), neopentyl (C5), 3-methyl-2-butanyl (C5), tertiary amyl (C5), and n-hexyl (C6). Additional examples of alkyl group include n-heptyl (C7), n-octyl (C8) and the like. Unless otherwise specified, each instance of an alkyl group is independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent. In certain embodiments, the alkyl group is unsubstituted C1-10 alkyl (e.g., —CH3). In certain embodiments, the alkyl group is substituted C1-10 alkyl.

"Alkenyl" refers to a straight-chain or branched hydrocarbon group having from 2 to 20 carbon atoms, one or more carbon-carbon double bonds (e.g., 1, 2, 3, or 4 carbon-carbon double bonds), and optionally one or more carbon-carbon triple bonds (e.g., 1, 2, 3, or 4 carbon-carbon triple bonds) ("C2-20 alkenyl"). In certain embodiments, alkenyl does not contain any triple bonds. In some embodiments, an alkenyl group has 2 to 10 carbon atoms ("C2-10 alkenyl"). In some embodiments, an alkenyl group has 2 to 9 carbon atoms ("C2-9 alkenyl"). In some embodiments, an alkenyl group has 2 to 8 carbon atoms ("C2-8 alkenyl"). In some embodiments, an alkenyl group has 2 to 7 carbon atoms ("C2-7 alkenyl"). In some embodiments, an alkenyl group has 2 to 6 carbon atoms ("C2-6 alkenyl"). In some embodiments, an alkenyl group has 2 to 5 carbon atoms ("C2-5 alkenyl"). In some embodiments, an alkenyl group has 2 to 4 carbon atoms ("C2-4 alkenyl"). In some embodiments, an alkenyl group has 2 to 3 carbon atoms ("C2-3 alkenyl"). In some embodiments, an alkenyl group has 2 carbon atoms ("C2 alkenyl"). The one or more carbon-carbon double bonds can be internal (such as in 2-butenyl) or terminal (such as in 1-butenyl). Examples of C2-4 alkenyl group include ethenyl (C2), 1-propenyl (C3), 2-propenyl (C3), 1-butenyl (C4), 2-butenyl (C4), butadienyl (C4), and the like. Examples of C2-6 alkenyl group include the aforementioned C2-4 alkenyl groups as well as pentenyl (C5), pentadienyl (C5), hexenyl (C6), and the like. Additional examples of alkenyl include heptenyl (C7), octenyl (C8), octatrienyl (C8), and the like. Unless otherwise specified, each instance of an alkenyl group is independently optionally substituted, i.e., unsubstituted (an "unsubstituted alkenyl") or substituted (a "substituted alkenyl") with one or more substituents e.g., for instance from 1 to 5 substituents, 1 to 3 substituents, or 1 substituent. In certain embodiments, the alkenyl group is unsubstituted C2-10 alkenyl. In certain embodiments, the alkenyl group is substituted C2-10 alkenyl.

"Alkynyl" refers to a straight-chain or branched hydrocarbon group having from 2 to 20 carbon atoms, one or more carbon-carbon triple bonds (e.g., 1, 2, 3, or 4 carbon-carbon triple bonds), and optionally one or more carbon-carbon double bonds (e.g., 1, 2, 3, or 4 carbon-carbon double bonds) ("C2-20 alkynyl"). In certain embodiments, alkynyl does not contain any double bonds. In some embodiments, an alkynyl group has 2 to 10 carbon atoms ("C2-10 alkynyl"). In some embodiments, an alkynyl group has 2 to 9 carbon atoms ("C2-9 alkynyl"). In some embodiments, an alkynyl group has 2 to 8 carbon atoms ("C2-8 alkynyl"). In some embodiments, an alkynyl group has 2 to 7 carbon atoms ("C2-7 alkynyl"). In some embodiments, an alkynyl group has 2 to 6 carbon atoms ("C2-6 alkynyl"). In some embodiments, an alkynyl group has 2 to 5 carbon atoms ("C2-5 alkynyl"). In some embodiments, an alkynyl group has 2 to 4 carbon atoms ("C2-4 alkynyl"). In some embodiments, an alkynyl group has 2 to 3 carbon atoms ("C2-3 alkynyl"). In some embodiments, an alkynyl group has 2 carbon atoms ("C2 alkynyl"). The one or more carbon-carbon triple bonds can be internal (such as in 2-butynyl) or terminal (such as in 1-butynyl). Examples of C2-4 alkynyl group include, without limitation, ethynyl (C2), 1-propynyl (C3), 2-propynyl (C3), 1-butynyl (C4), 2-butynyl (C4), and the like. Examples of C2-6 alkynyl group include the aforementioned C2-4 alkynyl group as well as pentynyl (C5), hexynyl (C6), and the like. Additional examples of alkynyl group include heptynyl (C7), octynyl (C8), and the like. Unless otherwise specified, each instance of an alkynyl group is independently optionally substituted, i.e., unsubstituted (an "unsubstituted alkynyl") or substituted (a "substituted alkynyl") with one or more substituents; e.g., for instance from 1 to 5 substituents, 1 to 3 substituents, or 1 substituent. In certain embodiments, the alkynyl group is unsubstituted C2-10 alkynyl. In certain embodiments, the alkynyl group is substituted C2-10 alkynyl.

"Aryl" refers to a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("C6-14 aryl"). In some embodiments, an aryl group has a ring of six carbon atoms ("C6 aryl"; e.g., phenyl). In some embodiments, an aryl group has ten ring carbon atoms ("C10 aryl"; e.g., naphthyl such as 1 naphthyl and 2-naphthyl). In some embodiments, an aryl group has fourteen ring carbon atoms ("C14 aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, and trinaphthalene. Particularly aryl groups include phenyl, naphthyl, indenyl, and tetrahydronaphthyl. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted C6-14 aryl. In certain embodiments, the aryl group is substituted C6-14 aryl.

"Heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system.

"Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl). In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl. Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Carbocyclyl" or "carbocyclic" refers to a radical of a non-aromatic cyclic hydrocarbon group having from 3 to 10 ring carbon atoms ("C3-10 carbocyclyl") and zero heteroatoms in the non-aromatic ring system. In some embodiments, a carbocyclyl group has 3 to 8 ring carbon atoms ("C3-8 carbocyclyl"). In some embodiments, a carbocyclyl group has 3 to 6 ring carbon atoms ("C3-6 carbocyclyl"). In some embodiments, a carbocyclyl group has 3 to 6 ring carbon atoms ("C3-6 carbocyclyl"). In some embodiments, a carbocyclyl group has 5 to 10 ring carbon atoms ("C5-10 carbocyclyl"). Exemplary C3-6 carbocyclyl groups include, but not limited to: cyclopropyl (C3), cyclopropenyl (C3), cyclobutyl (C4), cyclobutenyl (C4), cyclopentyl (C5), cyclopentenyl (C5), cyclohexyl (C6), cyclohexenyl (C6), cyclohexadienyl (C6), and the like. Exemplary C3-8 carbocyclyl groups include, but are not limited to: the above-mentioned C3-6 carbocyclic group, and cycloheptyl (C7), cycloheptenyl (C7), cycloheptadienyl (C7), cycloheptatrienyl (C7), cyclooctyl (C8), cyclooctenyl (C8), bicyclo[2.2.1]heptyl (C7), bicyclo[2.2.2]octyl (C8), and the like. Exemplary C3-10 carbocyclyl groups include, but are not limited to: the above-mentioned C3-8 carbocyclyl group, and cyclononyl (C9), cyclononenyl (C9), cyclodecyl (C10), cyclodecenyl (C10), octahydro-1H-indenyl (C9), decahydronaphthyl (C10), spiro[4.5]decyl (C10), etc. As illustrated by the foregoing examples, in some embodiments, a carbocyclyl group is a monocyclic ring ("monocyclic carbocyclyl") or a carbocyclyl group that comprises a fused ring system, a bridged ring system, or a spiro ring system, such as a bicyclic ring system ("bicyclic carbocyclyl"), and can be saturated or a partially unsaturated carbocyclyl group. "carbocyclyl" also includes ring systems in which the aforementioned carbocyclic ring is fused to one or more aryl or heteroaryl groups, wherein the point of attachment is on the carbocyclic ring, and in such cases the number of carbons continues to represent the number of carbons in the carbocyclic ring system. Unless otherwise specified, each of the carbocyclyl groups is independently optionally substituted, i.e., unsubstituted (an "unsubstituted carbocyclyl") or substituted with one or more substituents (a "substituted carbocyclyl"). In some embodiments, carbocyclyl is unsubstituted C3-10 carbocyclyl. In some embodiments, carbocyclyl is substituted C3-10 carbocyclyl. In some embodiments, "carbocyclyl" is a monocyclic, saturated carbocyclyl ("C3-10 cycloalkyl") having from 3 to 10 ring carbon atoms. In some embodiments, a cycloalkyl group has 3 to 8 ring carbon atoms ("C3-8 cycloalkyl"). In some embodiments, a cycloalkyl group has 3 to 6 ring carbon atoms ("C3-6 cycloalkyl"). In some embodiments, a cycloalkyl group has 5 to 6 ring carbon atoms ("C5-6 cycloalkyl"). In some embodiments, cycloalkyl groups have 5 to 10 ring carbon atoms ("C5-10 cycloalkyl"). Examples of C5-6 cycloalkyl include cyclopentyl (C5) and cyclohexyl (C6). Examples of the C3-6 cycloalkyl group include the above-mentioned C5-6 cycloalkyl groups, as well as cyclopropyl (C3) and cyclobutyl (C4). Examples of the C3-8 cycloalkyl group include the above-mentioned C3-6 cycloalkyl group, as well as cycloheptyl (C7) and cyclooctyl (C8). Unless otherwise specified, each instance of a cycloalkyl group is independently unsubstituted (an "unsubstituted cycloalkyl") or substituted (a "substituted cycloalkyl") with one or more substituents. In some embodiments, cycloalkyl is unsubstituted C3-10 cycloalkyl. In some embodiments, cycloalkyl is substituted C3-10 cycloalkyl.

"Heterocyclyl" or "heterocyclic" refers to a radical of a 3 to 10 membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclic groups containing one or more nitrogen atoms, the point of attachment can be carbon or a nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl. In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

"Hetero" when used to describe a compound or group present on a compound means that one or more carbon atoms in the compound or group have been replaced with a nitrogen, oxygen, or sulfur heteroatom. Hetero can be applied to any of the hydrocarbyl described above: for example, alkyl, e.g., heteroalkyl; cycloalkyl groups, e.g., heterocyclyl groups; aryl, e.g., heteroaryl; cycloalkenyl groups, e.g., cycloheteroalkenyl and the like; having from 1 to 5 heteroatoms, in particular 1 to 3 heteroatoms.

"Alkoxy" refers to the group —OR where R is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy.

Particular alkoxy groups are lower alkoxy, i.e. with between 1 and 6 carbon atoms. Further particular alkoxy groups have between 1 and 4 carbon atoms. Exemplary substituted alkoxy groups include, but are not limited to, —O—$(CH_2)_t(C_6$-$C_{10}$ aryl), —O—$(CH_2)_t$(5-10 membered heteroaryl), —O—$(CH_2)_t(C_3$-$C_{10}$ cycloalkyl), and —O—$(CH_2)_t$(4-10 membered heterocyclyl), wherein t is an integer from 0 to 4, and any substituted groups include aryl, heteroaryl, cycloalkyl or heterocyclyl groups present, can themselves be substituted by unsubstituted a $C_1$-$C_4$ alkyl group, halo, a unsubstituted $C_1$-$C_4$ alkoxy group, a unsubstituted $C_1$-$C_4$ haloalkyl group, a unsubstituted $C_1$-$C_4$ hydroxyalkyl group, or a unsubstituted $C_1$-$C_4$ haloalkoxy group or a hydroxy group.

"Carboxy" refers to the —C(O)OH.

"Cyano" refers to the —CN.

"Halo" or "halogen" refers to a fluoro atom (F), a chloro atom (Cl), a bromo atom (Br), and an iodo atom (I). In certain embodiments, the halo group is either a fluoro atom or a chloro atom.

"Hydroxy" refers to the —OH.

"Nitro" refers to the —NO2.

Other Definitions

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in J. Pharmaceutical Sciences (1977) 66:1-19. Pharmaceutically acceptable salts of the compounds of the present invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and N+ (C1-4alkyl) 4 salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

DETAILED DESCRIPTION OF CERTAIN EMBODIMENTS OF THE INVENTION

Figure 1:
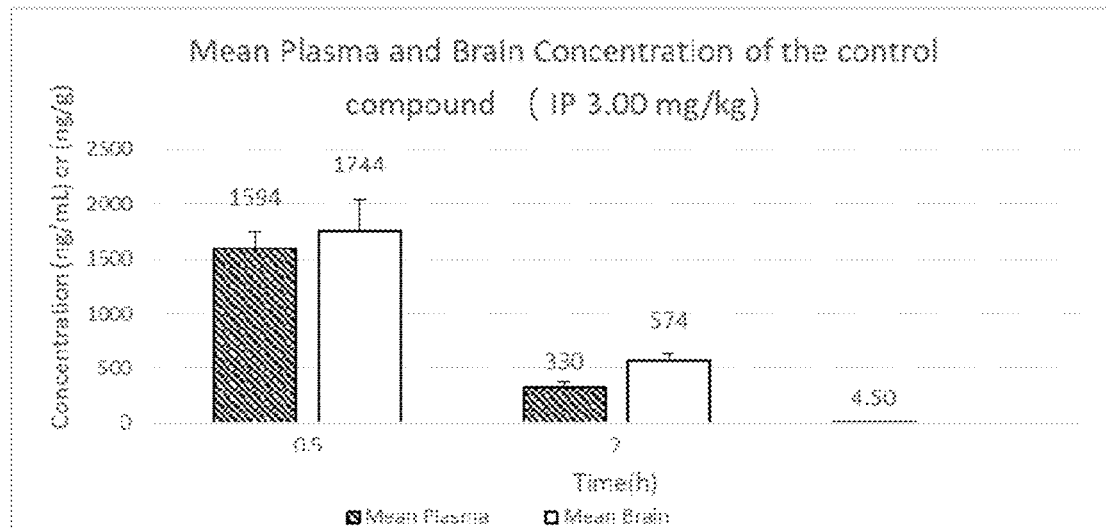
FIG. 1 is a graph showing changes of the control in plasma and brain over time.

In order to better explain the technical scheme of the invention, the invention provides synthesis or biological examples of a part of compounds, and does not further limit the protection scope of the invention.

Materials and Methods

The compounds provided herein can be prepared from easily available starting materials using the following general methods and procedures. It is understood that under typical or preferred process conditions (i.e., reaction temperature, time, mole ratio of reactants, solvent, pressures, etc.), other process conditions can be also used unless otherwise specified. Optimum reaction conditions can vary with the particular reactants or solvents used, but such conditions can be determined by those skilled in the art based on routine optimization.

In addition, it is obvious to those skilled in the art that conventional protecting groups can be required to prevent undesirable reactions of certain functional groups. How to select suitable protecting groups for particular functional groups and how to select suitable conditions for protection and de-protection are well known in the art.

The compounds provided herein can be isolated and purified by known standard methods, including, but not limited to, recrystallization, column chromatography, HPLC, or Supercritical Fluid Chromatography (SFC). The preparation details of the representative pyrazoles herein are provided in the following reaction schemes.

The compounds provided herein can be prepared according to methods described in the art using appropriate reagents, starting materials and purification methods known to those skilled in the art.

Example 1: Synthesis of Compound KH001

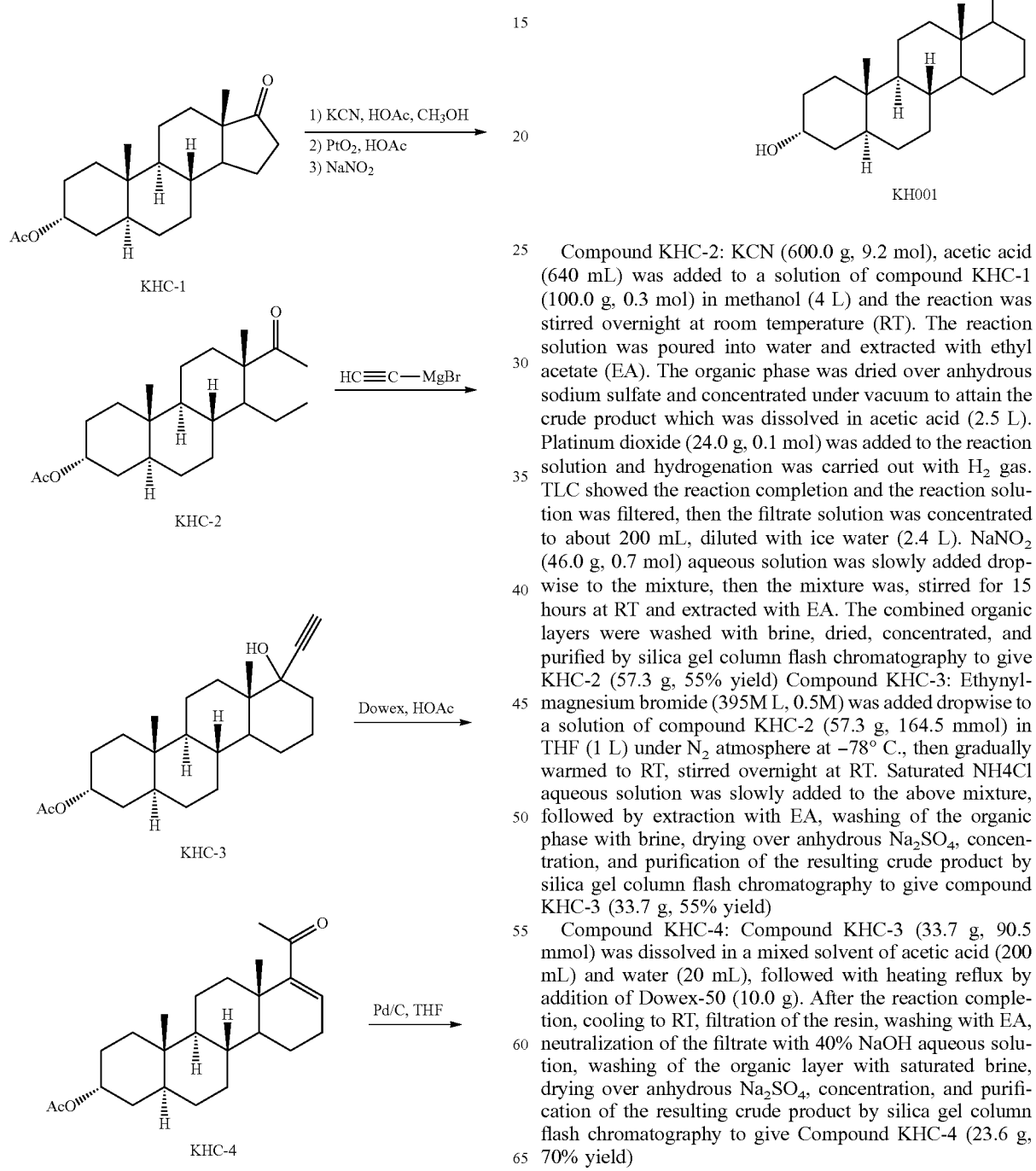

Compound KHC-2: KCN (600.0 g, 9.2 mol), acetic acid (640 mL) was added to a solution of compound KHC-1 (100.0 g, 0.3 mol) in methanol (4 L) and the reaction was stirred overnight at room temperature (RT). The reaction solution was poured into water and extracted with ethyl acetate (EA). The organic phase was dried over anhydrous sodium sulfate and concentrated under vacuum to attain the crude product which was dissolved in acetic acid (2.5 L). Platinum dioxide (24.0 g, 0.1 mol) was added to the reaction solution and hydrogenation was carried out with $H_2$ gas. TLC showed the reaction completion and the reaction solution was filtered, then the filtrate solution was concentrated to about 200 mL, diluted with ice water (2.4 L). $NaNO_2$ (46.0 g, 0.7 mol) aqueous solution was slowly added dropwise to the mixture, then the mixture was, stirred for 15 hours at RT and extracted with EA. The combined organic layers were washed with brine, dried, concentrated, and purified by silica gel column flash chromatography to give KHC-2 (57.3 g, 55% yield) Compound KHC-3: Ethynyl-magnesium bromide (395M L, 0.5M) was added dropwise to a solution of compound KHC-2 (57.3 g, 164.5 mmol) in THF (1 L) under $N_2$ atmosphere at −78° C., then gradually warmed to RT, stirred overnight at RT. Saturated NH4Cl aqueous solution was slowly added to the above mixture, followed by extraction with EA, washing of the organic phase with brine, drying over anhydrous $Na_2SO_4$, concentration, and purification of the resulting crude product by silica gel column flash chromatography to give compound KHC-3 (33.7 g, 55% yield)

Compound KHC-4: Compound KHC-3 (33.7 g, 90.5 mmol) was dissolved in a mixed solvent of acetic acid (200 mL) and water (20 mL), followed with heating reflux by addition of Dowex-50 (10.0 g). After the reaction completion, cooling to RT, filtration of the resin, washing with EA, neutralization of the filtrate with 40% NaOH aqueous solution, washing of the organic layer with saturated brine, drying over anhydrous $Na_2SO_4$, concentration, and purification of the resulting crude product by silica gel column flash chromatography to give Compound KHC-4 (23.6 g, 70% yield)

Compound KHC-5: Compound KHC-4 (23.6 g, 63.3 mmol) and palladium black (1.2 g) in THF (200 mL) were hydrogenated with H₂ gas, after stirring overnight at RT, the mixture was filtered through a pad of celite, washed with EA, and the filtrate was concentrated in vacuo to provide the crude compound which was recrystallized from acetone to give compound KHC-5 (19.0 g, 80% yield)

Compound KH001: NaOH aqueous solution (50ML, 1M) was added slowly to a solution of compound KHC-5 (19.0 g, 50.8 mmol) in THF (200 ml) and stirring overnight at RT, the pH of the reaction solution was adjusted with dilute HCl and then the solution was extracted with EA. The organic phase was washed with brine, dried over anhydrous Na₂SO₄, and concentrated to give the crude product which was purified by silica gel column flash chromatography to give Compound KH001 (13.5 g, 80% yield) ¹H NMR (400 MHZ, CDCl₃), δ 4.06 (s, 1H), 2.32-2.28 (dd, 1H), 2.15 (s, 3H), 1.84-1.77 (m, 2H), 1.74-1.61 (m, 5H), 1.61-1.54 (m, 3H), 1.48-1.46 (m, 1H), 1.33-1.14 (m, 10H), 1.02-0.95 (m, 1H), 0.93 (s, 3H), 0.85-0.79 (m, 3H), 0.75 (s, 3H).

Example 2: Synthesis of Compound KH002

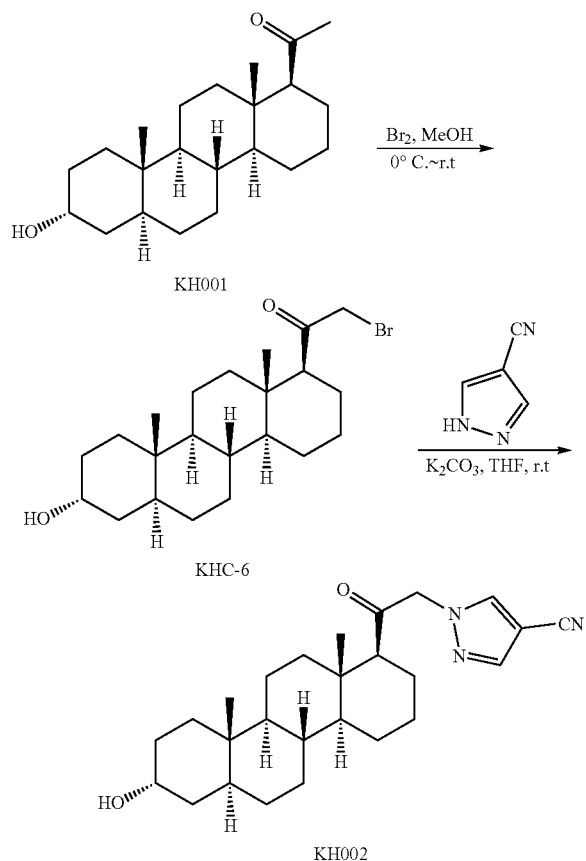

Compound KHC-6: Compound KH001 (1.5 g, 4.5 mmol) synthesized in example 1 was dissolved in CH₃OH (40 mL) until the solution was clear, then the solution was cooled to 5° C. in the wet ice Subsequently bromine (1.5 g, 9.2 mmol) was added dropwise to the cooled solution. The ice-bath was removed and the reaction was carried out at RT for 4 hours, the reaction solution became pale yellow from the orange color. TLC monitoring of the reaction showed that the reaction was complete, water (30 mL) was added to the reaction solution, extraction was carried out with EA (2×35 mL), the combined organic layers were washed with saturated brine, dried over anhydrous Na₂SO₄, and the solvent was distilled under reduced pressure to give crude pale yellow solid which was purified by silica gel column flash chromatography (eluent:CH₂Cl₂) to give a white solid (1.0 g, 56.7% yield).

Compound KH002: Compound KHC-6 (80 mg, 0.2 mmol) was dissolved in THF (5 mL) until the solution was clear, then K₂CO₃ (83 mg, 0.6 mmol) and 4-cyanopyrazole (56 mg, 0.6 mmol) was added, Reaction was performed at room temperature. overnight. TLC monitoring of the reaction showed that the reaction was complete, then the reaction was washed with 10 ml of water and extracted with EA (2×20 mL), the combined organic layers were washed with saturated brine, dried over anhydrous Na₂SO₄ and the solvent was distilled under reduced pressure to give crude pale yellow solid which was purified by silica gel column flash chromatography (eluent:CH₂Cl₂/CH₃OH=100:1) and then recrystallized EA/PE=1:10) to attain white solid (36 mg, 42.5% yield). ¹H NMR (400 MHZ, CDCl₃) δ 7.82 (s, 1H), 7.80 (s, 1H), 5.06-4.93 (m, 2H), 4.05-4.04 (m, 1H), 2.32 (dd, 1H), 1.88-1.83 (m, 2H), 1.79-1.66 (m, 4H), 1.64-1.58 (m, 2H), 1.54-1.44 (m, 4H), 1.39-1.13 (m, 9H), 1.04-0.97 (m, 1H), 0.94 (s, 3H), 0.85-0.75 (m, 3H), 0.74 (s, 3H).

Example 3: Synthesis of Compound KH003

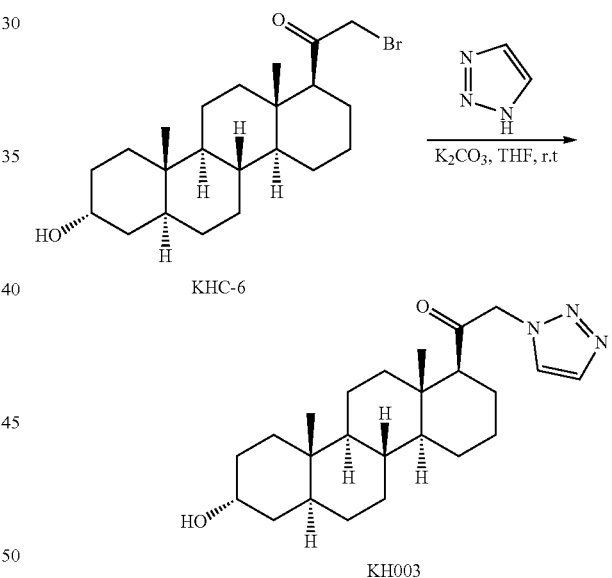

Compound KH003: Compound KHC-6 (50 mg, 0.1 mmol) was dissolved in THF (5 mL) until the solution was clear, then K₂CO₃ (50 mg, 0.3 mmol) and 1H-triazole (25 mg, 0.3 mmol) was added, Reaction was performed at room temperature overnight. TLC monitoring of the reaction showed that the reaction was complete, then the reaction was washed with 10 ml water, extracted with EA (2×20 mL), the combined organic layers were washed with saturated brine, dried over anhydrous Na₂SO₄ and the solvent was distilled under reduced pressure to give crude pale yellow solid which was purified by silica gel column flash chromatography (eluent:CH₂Cl₂/CH₃OH=150:1) and then recrystal- lized (EA/PE=1:10) to attain white solid (17 mg, 35.5% yield). ¹H NMR (400 MHZ, CDCl₃) δ 7.76 (s, 1H), 7.60 (s, 1H), 5.31-5.17 (m, 2H), 4.06-4.05 (m, 1H), 2.37 (d, 1H), 1.87-1.61 (m, 8H), 1.52-1.10 (m, 13H), 1.04-0.98 (m, 1H), 0.95 (s, 3H), 0.92-0.79 (m, 3H), 0.74 (s, 3H).

Example 4: Synthesis of Compound KH004 and KH005

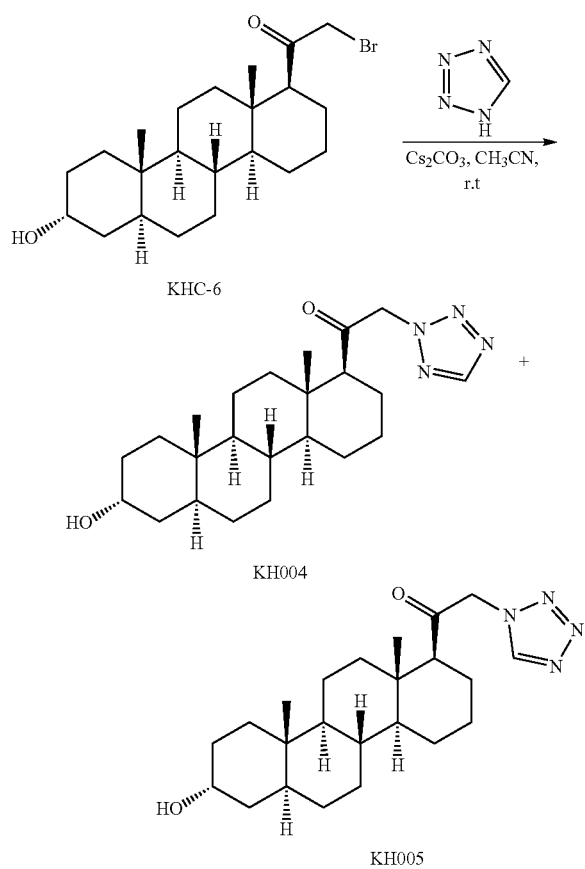

Compound KH004 and KH005: Compound KHC-6 (103 mg, 0.2 mmol) was dissolved in CH₃CN (15 mL) until the solution was clear, then Cs₂CO₃ (244 mg, 0.7 mmol) and 1H-tetrazolium (53 mg, 0.7 mmol) was added, Reaction was performed at room temperature. TLC monitoring of the reaction showed that the reaction was complete, the reaction was washed with 10 ml water and extracted with EA (2×25 mL), the combined organic layers were washed with saturated brine, dried over anhydrous Na₂SO₄ and the solvent was distilled under reduced pressure to give crude pale yellow solid which was purified by silica gel column flash chromatography (eluent:CH₂Cl₂/CH₃OH=150:1 to 90:1) to give two compounds which were respectively recrystallized (EA/PE=1:10) to attain white solid one (24 mg, 24.0%) and white solid two (36 mg, 36.0% yield). White solid 1 (KH004) ¹H NMR (400 MHZ, CDCl₃) δ 8.57 (s, 1H), 5.50 (s, 2H), 4.06-4.05 (m, 1H), 2.35 (dd, 1H), 1.92-1.81 (m, 3H), 1.74-1.68 (m, 3H), 1.64-1.57 (m, 4H), 1.46-1.11 (m, 10H), 1.05-0.98 (m, 2H), 0.96 (s, 3H), 0.88-0.78 (m, 3H), 0.75 (s, 3H). White solid 2 (KH005) ¹H NMR (400 MHZ, CDCl₃) δ 8.71 (s, 1H), 5.38-5.23 (m, 2H), 4.06-4.05 (m, 2H), 2.41 (dd, 1H), 2.28 (dd, 1H), 1.91-1.72 (m, 4H), 1.68-1.51 (m, 7H), 1.47-1.11 (m, 10H), 1.06-0.99 (m, 1H), 0.95 (s, 3H), 0.91-0.78 (m, 3H), 0.75 (s, 3H).

Example 5: Synthesis of Compound KH006

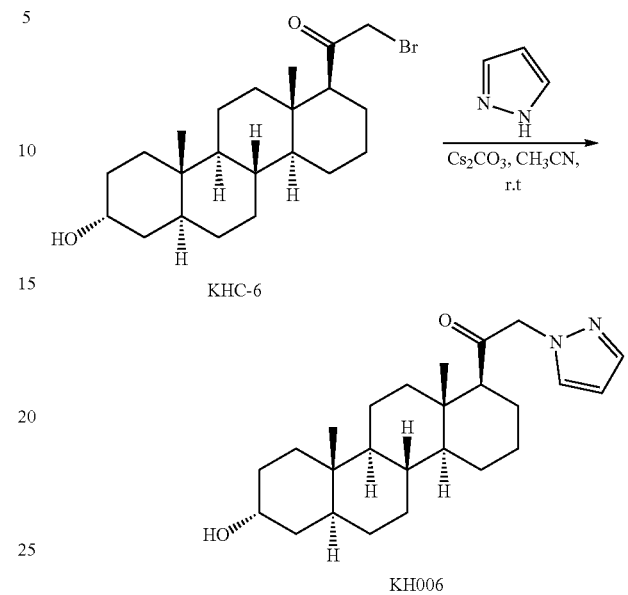

Compound KH006: Compound KHC-6 (50 mg, 0.1 mmol) was dissolved in CH₃CN (8 mL), then Cs₂CO₃ (117 mg, 0.3 mmol) and 1H-pyrazole (24 mg, 0.3 mmol) was added, Reaction was performed at room temperature overnight. TLC monitoring of the reaction showed that the reaction was complete, The reaction was washed with water 10 ml and extracted with EA (2×20 mL), the combined organic layers were washed with saturated brine, dried over anhydrous Na₂SO₄, and the solvent was distilled under reduced pressure to give a crude pale yellow solid which was purified by flash chromatography on silica gel column (eluent:CH₂Cl₂/CH₃OH=100:1) and recrystallized (EA/PE=1:10) to attain a white solid (24 mg, 50.2% yield). ¹H NMR (400 MHZ, CDCl₃) δ 7.56 (d, 1H), 7.39 (d, 1H), 6.34 (s, 1H), 5.03-4.92 (m, 2H), 4.05-4.04 (m, 1H), 2.28 (dd, 1H), 1.86-1.73 (m, 4H), 1.71-1.61 (m, 3H), 1.60-1.49 (m, 4H), 1.48-1.09 (m, 10H), 1.03-0.97 (m, 1H), 0.95 (s, 3H), 0.81-0.76 (m, 3H), 0.74 (s, 3H).

Example 6: Synthesis of Compound KH007

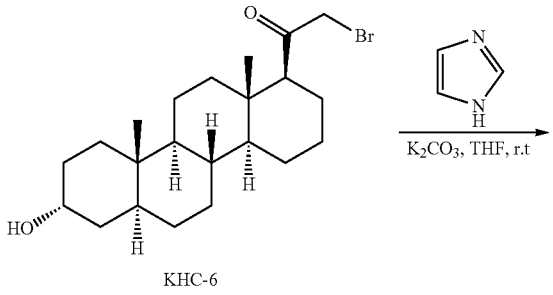

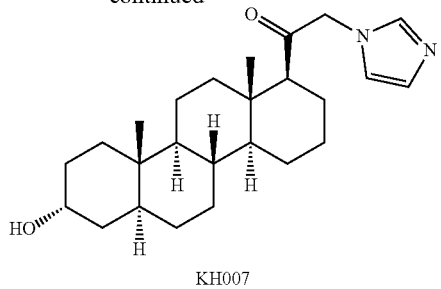

KH007

Compound KH007: Compound KHC-6 (150 mg, 0.3 mmol) was dissolved in THF (10 mL), then K₂CO₃ (152 mg, 1.1 mmol) and 1H-imidazole (75 mg, 1.1 mmol) was added. Reaction was performed at room temperature overnight. TLC monitoring of the reaction showed that the reaction was complete. Water (10 mL) was added to the reaction solution, extraction was carried out with EA (2×20 mL), the combined organic layers were washed with saturated brine, dried over anhydrous Na₂SO₄, and the solvent was distilled under reduced pressure to give crude pale yellow solid which was purified by silica gel column flash chromatography (eluent: CH₂Cl₂/CH₃OH=30:1), followed by recrystallization (EA) to give white solid (35 mg, 24.1% yield). $^1$H NMR (400 MHZ, CDCl₃) δ 7.47 (s, 1H), 7.11 (s, 1H), 6.85 (s, 1H), 4.74 (d, 2H), 4.06-4.05 (m, 1H), 2.30 (dd, 1H), 1.88-1.68 (m, 4H), 1.64-1.56 (m, 3H), 1.52-1.45 (m, 4H), 1.40-1.11 (m, 10H), 1.04-0.97 (m, 1H), 0.95 (s, 3H), 0.83-0.77 (m, 3H), 0.75 (s, 3H).

Example 7: Synthesis of Compound KH008

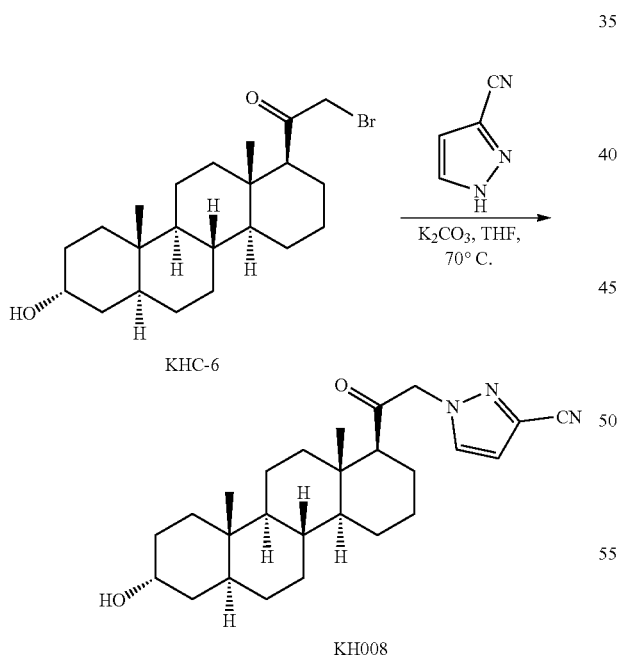

KHC-6

KH008

Compound KH008: Compound KHC-6 (100 mg, 0.2 mmol) was dissolved in THF (10 mL), then K₂CO₃ (97 mg, 0.7 mmol) and 3-cyanopyrazole (68 mg, 0.7 mmol) was added, Reaction was performed at 70° C. over 2 hours. TLC monitoring of the reaction showed that the reaction was complete, water (10 mL) was added to the reaction solution, extraction was carried out with EA (2×20 mL), the combined organic layers were washed with saturated brine, dried over anhydrous Na₂SO₄, and the solvent was distilled under reduced pressure to give crude pale yellow solid which was purified by TLC (eluent:PE/ACETONE=3:1), followed by recrystallization (CH₃CN) to give white solid (20 mg, 19.4% yield). $^1$H NMR (400 MHZ, CDCl₃) δ 7.44 (d, 1H), 6.72 (d, 1H), 6.34 (s, 1H), 5.00 (q, 2H), 4.06-4.05 (m, 1H), 2.32 (dd, 1H), 1.88-1.68 (m, 4H), 1.63-1.60 (m, 3H), 1.50-1.45 (m, 4H), 1.41-1.11 (m, 10H), 1.04-0.97 (m, 1H), 0.95 (s, 3H), 0.87-0.79 (m, 3H), 0.75 (s, 3H).

Example 8: Synthesis of Compound KH009

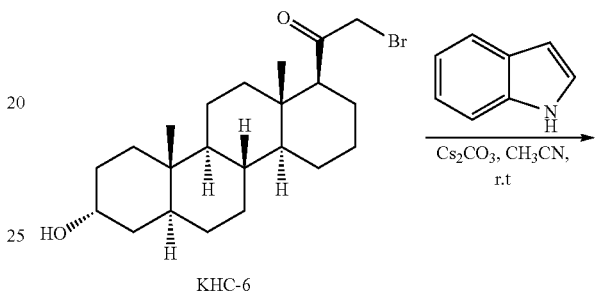

KHC-6

KH009

Compound KH009: Compound KHC-6 (50 mg, 0.1 mmol) was clearly dissolved in CH₃CN (5 mL), then Cs₂CO₃ (120 mg, 0.3 mml) and 1H-indole (68 mg, 0.7 mmol) was added, Reaction was performed at room temperature overnight. TLC monitoring of the reaction showed that the reaction was complete, Water (10 mL) was added to the reaction solution, extraction was carried out with EA (2×20 mL), the combined organic layers were washed with saturated brine, dried over anhydrous Na₂SO₄, and the solvent was distilled under reduced pressure to give crude pale yellow solid which was purified by TLC (eluent: CH₂Cl₂/EA=10:1) to give pale yellow solid (34 mg, 62.4% yield). $^1$H NMR (400 MHZ, CDCl₃) δ 7.65-7.63 (m, 1H), 7.21-7.18 (m, 1H), 7.13-7.10 (m, 2H), 7.01-7.00 (m, 1H), 6.57 (d, 1H), 4.83 (d, 2H), 4.06-4.05 (m, 1H), 2.30 (dd, 1H), 1.82-1.72 (m, 4H), 1.64-1.61 (m, 3H), 1.51-1.45 (m, 4H), 1.41-1.11 (m, 10H), 1.01-0.96 (m, 1H), 0.96 (s, 3H), 0.92-0.77 (m, 3H), 0.74 (s, 3H).

Example 9: Synthesis of Compound KH010

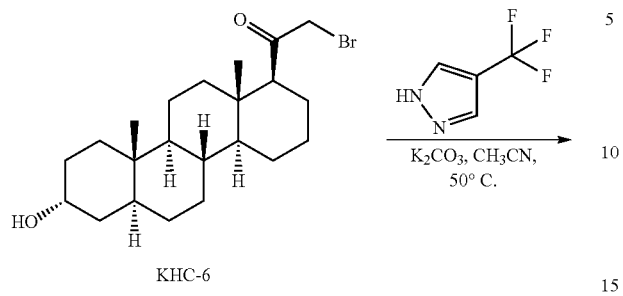

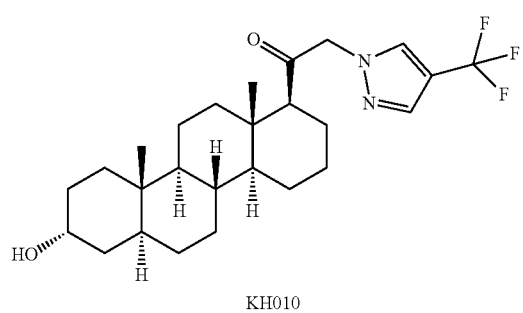

Compound KH010: Compound KHC-6 (100 mg, 0.2 mmol) was dissolved in CH₃CN (5 mL), then K₂CO₃ (101 mg, 0.7 mml) and 4-(trifluoromethyl)-1H-pyrazole (35 mg, 0.2 mmol) was added, Reaction was performed at 50° C. over 2 hours. TLC monitoring of the reaction showed that the reaction was complete, Water (10 mL) was added to the reaction solution, extraction was carried out with EA (2×20 mL), the combined organic layers were washed with saturated brine, dried over anhydrous Na₂SO₄, and the solvent was distilled under reduced pressure to give crude pale yellow solid which was purified by silica gel column flash chromatography (eluent:PE/ACETONE=7:1), followed by recrystallization (CH₃CN) to give white solid (61 mg, 53.1% yield). ¹H NMR (400 MHZ, CDCl₃) δ 7.71 (d, 2H), 4.98 (q, 2H), 4.06-4.05 (m, 1H), 2.32 (dd, 1H), 1.87-1.68 (m, 4H), 1.64-1.57 (m, 3H), 1.52-1.45 (m, 4H), 1.41-1.11 (m, 10H), 1.04-0.97 (m, 1H), 0.95 (s, 3H), 0.87-0.82 (m, 3H), 0.74 (s, 3H).

Example 10: Synthesis of Compound KH011

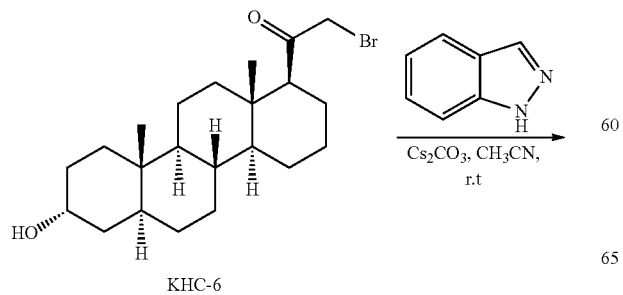

Compound KH011: Compound KHC-6 (50 mg, 0.1 mmol) was dissolved in CH₃CN (5 mL), then Cs₂CO₃ (120 mg, 0.3 mml) and 1H-indazole (43 mg, 0.3 mmol) was added, Reaction was performed at room temperature overnight. TLC monitoring of the reaction showed that the reaction was complete, Water (10 mL) was added to the reaction solution, extraction was carried out with EA (2×20 mL), the combined organic layers were washed with saturated brine, dried over anhydrous Na₂SO₄, and the solvent was distilled under reduced pressure to give crude pale yellow solid which was purified by TLC (eluent:PE/ACETONE=3:1), followed by recrystallization (CH₃CN) to give white solid (20 mg, 36.6%). ¹H NMR (400 MHZ, CDCl₃) δ 8.11 (s, 1H), 7.78 (d, 1H), 7.45-7.41 (m, 1H), 7.23-7.19 (m, 2H), 5.31-5.20 (m, 2H), 4.06-4.05 (m, 1H), 2.35 (dd, 1H), 1.87-1.72 (m, 4H), 1.67-1.63 (m, 3H), 1.54-1.45 (m, 4H), 1.42-1.14 (m, 10H), 1.01-0.98 (m, 1H), 0.96 (s, 3H), 0.93-0.78 (m, 3H), 0.75 (s, 3H).

Example 11: Synthesis of Compound KH012

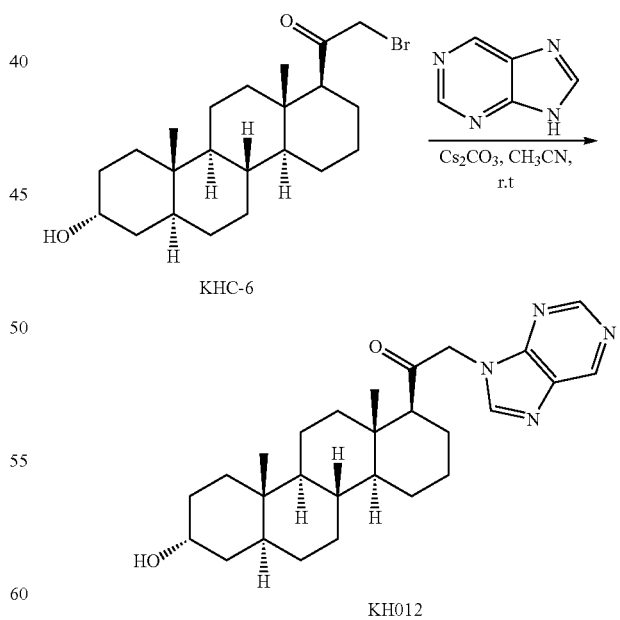

Compound KH012: Compound KHC-6 (50 mg, 0.1 mmol) was dissolved in CH₃CN (5 ml), then Cs₂CO₃ (120 mg, 0.3 mmol) and 1H-purine (44 mg, 0.3 mmol) was added Reaction was performed at room temperature overnight. TLC monitoring of the reaction showed that the reaction was complete, Water (10 mL) was added to the reaction solution, the mixture was extracted with EA (2×20 mL), the combined organic layers were washed with saturated brine, dried over anhydrous Na$_2$SO$_4$ and the solvent was distilled under reduced pressure to give crude product was obtained as a pale yellow solid which was purified by TLC (eluent: CH$_2$Cl$_2$/CH$_3$OH=20:1) followed by recrystallisation (CH$_3$CN) to give a white solid (5 mg, 9.1% yield). $^1$H NMR (400 MHZ, CDCl$_3$) δ 9.22 (s, 1H), 9.06 (s, 1H), 8.25 (s, 1H), 5.18 (q, 2H), 4.07-4.06 (m, 1H), 2.49 (dd, 1H), 1.93-1.72 (m, 4H), 1.68-1.65 (m, 3H), 1.58-1.45 (m, 4H), 1.42-1.13 (m, 10H), 1.06-1.00 (m, 1H), 0.96 (s, 3H), 0.90-0.80 (m, 3H), 0.74 (s, 3H).

Example 12: Synthesis of Compound KH013

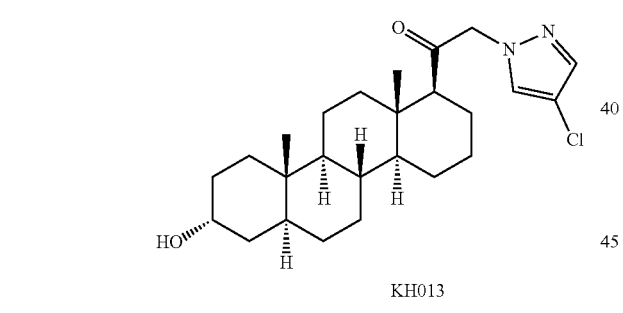

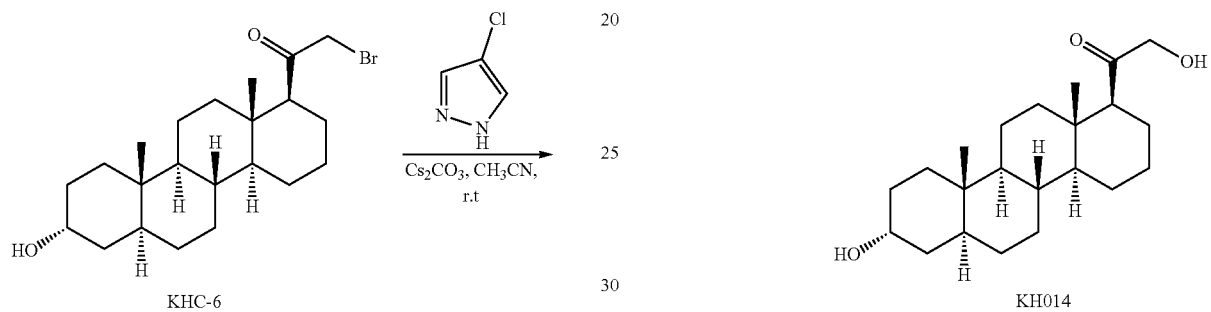

Compound KH013: Compound KHC-6 (80 mg, 0.2 mmol) was dissolved in CH$_3$CN (8 mL), then Cs$_2$CO$_3$ (196 mg, 0.6 mmol) and 4-chloropyrazole (62 mg, 0.6 mmol) was added, Reaction was performed at room temperature overnight. TLC monitoring of the reaction showed that the reaction was complete, 15 mL water was added to the reaction mixture, the mixture was extracted with EA (2×30 mL), the combined organic layers were washed with saturated brine, dried over anhydrous Na$_2$SO$_4$, and the solvent was distilled under reduced pressure to give crude pale yellow solid, which was purified by silica gel column flash chromatography (eluent:CH$_2$Cl$_2$/CH$_3$OH=100:1) and then recrystallized (EA/PE=1:10) to give a white solid (28 mg, 32.3% yield). $^1$H NMR (400 MHZ, CDCl$_3$) δ 7.46 (s, 1H), 7.38 (s, 1H), 4.96-4.83 (m, 2H), 4.06-4.05 (m, 1H), 2.19 (dd, 1H), 1.86-1.71 (m, 4H), 1.64-1.55 (m, 3H), 1.51-1.45 (m, 4H), 1.45-1.10 (m, 10H), 1.03-0.96 (m, 1H), 0.95 (s, 3H), 0.86-0.77 (m, 3H), 0.74 (s, 3H).

Example 13: Synthesis of Compound KH014

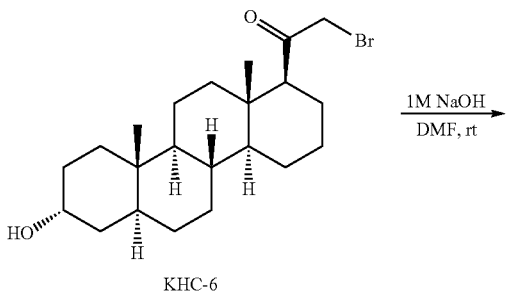

Compound KH014: compound KHC-6 (60 mg, 0.15 mmol) was dissolved in DMF (5 mL) then NaOH (1 mL, 1.0 mmol) was added, Reaction was performed at room temperature overnight. TLC monitoring of the reaction showed that the reaction was complete, 10 mL water was added to the reaction mixture, the mixture was extracted with EA (2×20 mL), the combined organic layers were washed with saturated NaCl, dried over anhydrous Na$_2$SO$_4$, and the solvent was distilled under reduced pressure to give crude product which was purified by TLC (eluent:CH$_2$Cl$_2$/CH$_3$OH=50:1) to give a white solid (12 mg, 22.92% yield).

$^1$H NMR (400 MHZ, DMSO-d6) δ 4.94-4.89 (m, 1H), 4.18 (t, 1H), 4.06-4.02 (m, 2H), 3.80 (t, 1H), 2.27 (dd, 1H), 1.77-0.65 (m, 27H), 0.68 (s, 3H).

Example 14: Synthesis of Compound KH015

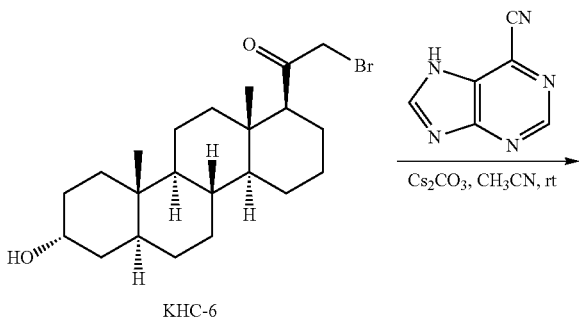

-continued

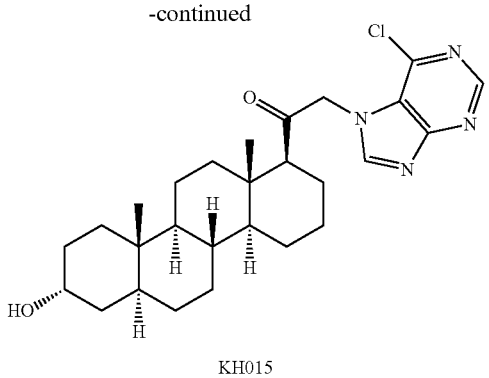

KH015

Compound KH015: Compound KHC-6 (60 mg, 0.15 mmol) was dissolved in CH$_3$CN (5 mL), then Cs$_2$CO$_3$ (98 mg, 0.30 mmol) and 6-chloropurine (46 mg, 0.30 mmol) was added, Reaction was performed at room temperature overnight. TLC monitoring of the reaction showed that the reaction was complete, 10 ml water was added to the reaction mixture, the mixture was extracted with EA (2×20 mL), the combined organic layers were washed with saturated NaCl, dried over anhydrous Na$_2$SO$_4$, and the solvent was distilled under reduced pressure to give crude product which was purified by TLC (eluent:CH$_2$Cl$_2$/CH$_3$OH=40:1) to give a white solid (39 mg, 53.61% yield).

$^1$H NMR (400 MHZ, DMSO-d6) δ 8.60 (s, 1H), 8.37 (s, 1H), 5.41 (q, 2H), 4.20 (d, 1H), 3.79 (t, 1H), 2.56 (dd, 1H), 1.80-0.75 (m, 27H), 0.69 (s, 3H).

Example 15: Synthesis of Compound KH016

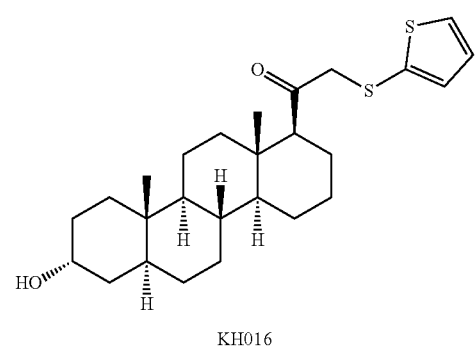

KH016

Compound KH016: KHC-6 (60 mg, 0.15 mmol) was dissolved in CH$_3$CN 5 mL, then Cs$_2$CO$_3$ (98 mg, 0.30 mmol) and 2-mercaptothiophene (17 mg, 0.30 mmol) was added, Reaction was performed at room temperature overnight. TLC monitoring of the reaction showed that the reaction was complete, 10 ml water was added to the reaction mixture, the mixture was extracted with EA (2×20 mL), the combined organic layers were washed with saturated NaCl, dried over anhydrous Na$_2$SO$_4$, and the solvent was distilled under reduced pressure to give crude product which was purified by TLC (eluent:CH$_2$Cl$_2$/CH$_3$OH=40:1) to give a white solid (19 mg, 28.34% yield).

$^1$H NMR (400 MHZ, CDCl$_3$) δ 7.35 (d, 1H), 7.14 (d, 1H), 6.95 (dd, 1H), 4.04 (t, 1H), 3.62 (q, 2H), 2.45 (dd, 1H), 1.65-0.81 (m, 27H), 0.73 (s, 3H).

Example 16: Synthesis of Compound KH017

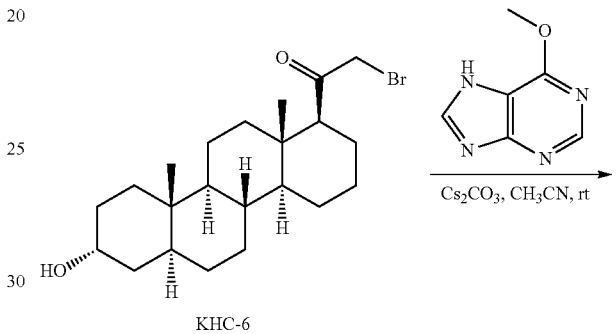

KHC-6

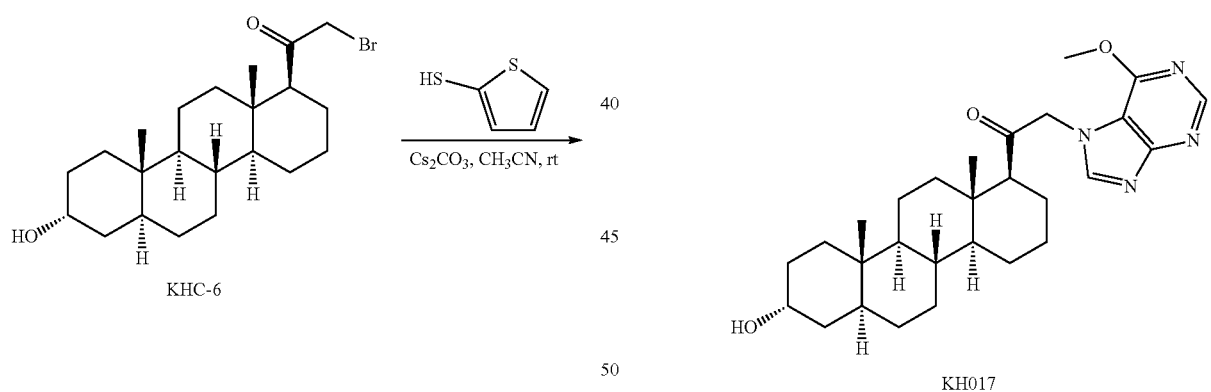

KH017

Compound KH017: KHC-6 (60 mg, 0.15 mmol) was dissolved in CH$_3$CN 5 mL, then Cs$_2$CO$_3$ (98 mg, 0.30 mmol) and 6-methoxypurine (45 mg, 0.30 mmol) was added, Reaction was performed at room temperature overnight. TLC monitoring of the reaction showed that the reaction was complete, 10 ml water 10 mL was added to the reaction mixture, the mixture extracted with EA (2×20 mL), the combined organic layers were washed with saturated NaCl, dried over anhydrous Na$_2$SO$_4$, and the solvent was distilled under reduced pressure to give crude product which was purified by TLC (eluent:CH$_2$Cl$_2$/CH$_3$OH=40:1) to give a white solid (46 mg, 63.76% yield).

$^1$H NMR (400 MHZ, DMSO-d6) δ 8.57 (s, 1H), 8.32 (s, 1H), 5.37 (q, 2H), 4.20 (d, 1H), 3.91 (s, 3H), 3.79 (t, 1H), 2.53 (dd, 1H), 1.79-0.75 (m, 27H), 0.69 (s, 3H).

Example 17: Synthesis of Compound KH018 and KH019

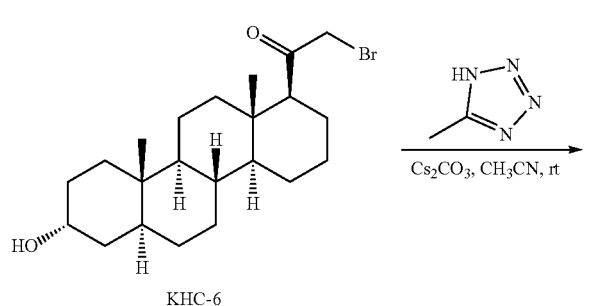

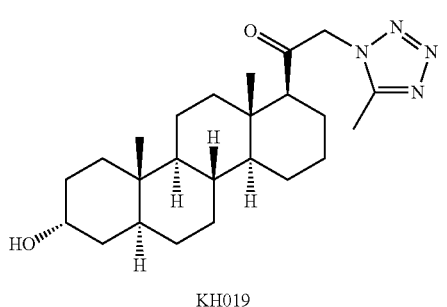

Compound KH018 and KH019: KHC-6 (60 mg, 0.15 mmol) was dissolved in CH$_3$CN 5 mL, then Cs$_2$CO$_3$ (98 mg, 0.30 mmol) and 5-methyl-1H-tetrazole (25 mg, 0.30 mmol) was added, Reaction was performed at room temperature overnight. TLC monitoring of the reaction showed that the reaction was complete, 10 ml water was added to the reaction mixture, the mixture was extracted with EA (2×20 mL), the combined organic layers were washed with saturated NaCl, dried over anhydrous Na$_2$SO$_4$, and the solvent was distilled under reduced pressure to give crude product which was purified by TLC (eluent:CH$_2$Cl$_2$/CH$_3$OH=40:1) to give white solid KH6070053-1 (13 mg, 20.88%) and KH6070053-2 (27 mg, 43.37%) as white solids, respectively.

$^1$H NMR (400 MHZ, CDCl$_3$) δ 4.39 (s, 2H), 4.05 (t, 1H), 2.56 (s, 3H), 2.34 (dd, 1H), 1.92-0.76 (m, 27H), 0.74 (s, 3H).

$^1$H NMR (400 MHZ, CDCl$_3$) δ 5.15 (dd, 2H), 4.06 (t, 1H), 2.43 (s, 3H), 2.39 (dd, 1H), 1.95-0.78 (m, 27H), 0.75 (s, 3H).

Example 18: Synthesis of Compound KH020

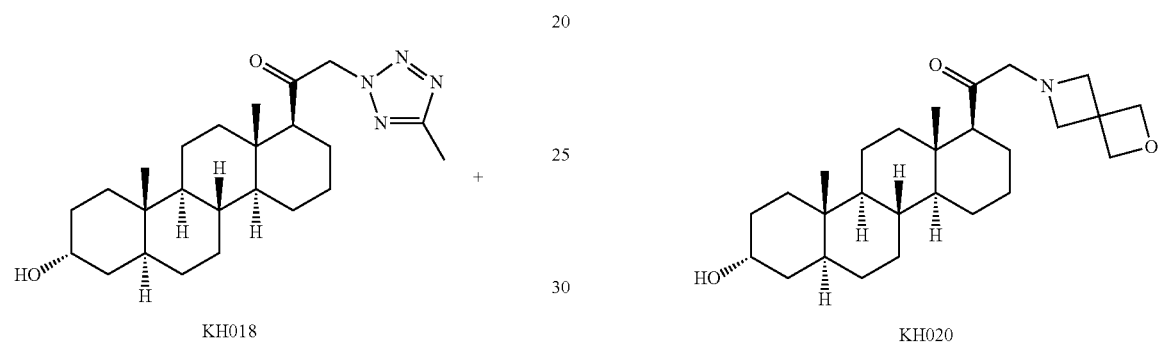

Compound KH020: KHC-6 (60 mg, 0.15 mmol) was dissolved in CH$_3$CN 5 mL, then Cs$_2$CO$_3$ (98 mg, 0.30 mmol) and 2-oxa-6-aza-spiro[3,3]Heptane (30 mg, 0.30 mmol) was added, Reaction was performed at room temperature overnight. TLC monitoring of the reaction showed that the reaction was complete, 10 ml water was added to the reaction mixture, the mixture was extracted with EA (2×20 mL), the combined organic layers were washed with saturated NaCl, dried over anhydrous Na$_2$SO$_4$, and the solvent was distilled under reduced pressure to give crude product which was purified by TLC (eluent:CH$_2$Cl$_2$/CH$_3$OH=40:1) to give a white solid (21 mg, 32.56% yield).

$^1$H NMR (400 MHZ, CDCl$_3$) δ 4.75 (s, 4H), 4.04 (t, 1H), 3.57 (dd, 4H), 3.40 (dd, 2H), 2.13 (dd, 1H), 1.90-0.75 (m, 27H), 0.73 (s, 3H).

Example 19: Synthesis of Compound KH021

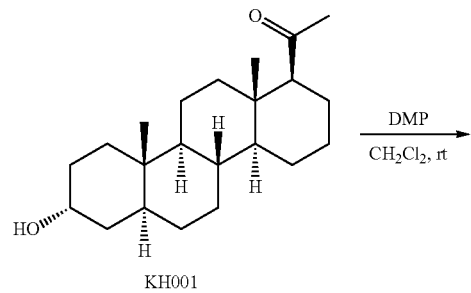

-continued

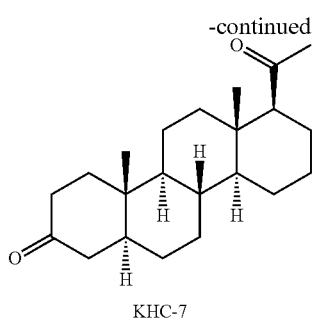
KHC-7

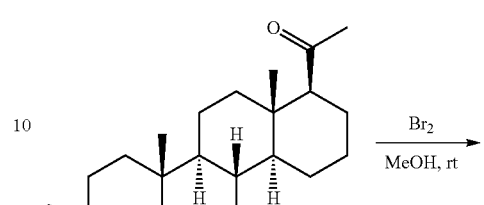

Example 20: Synthesis of Compound KH022 and KH023

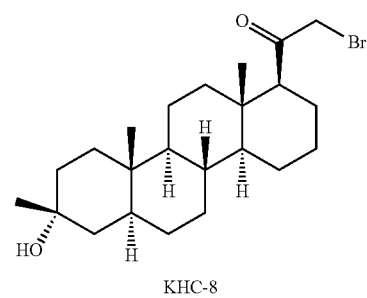
KH021

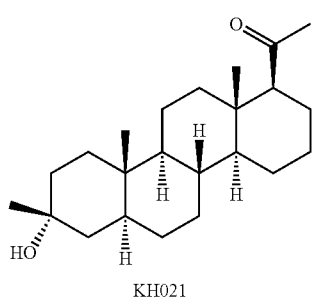
KH021

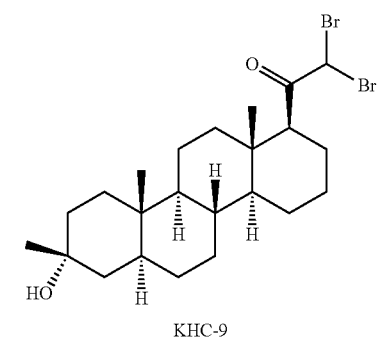
KHC-8

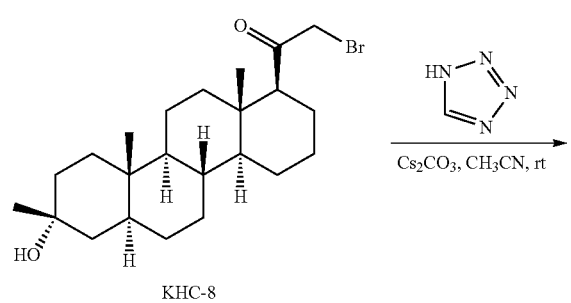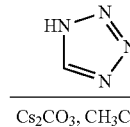
KHC-9

Compound KHC-7: KH001 (0.70 g, 2.11 mmol) was dissolved in 100 mL $CH_2Cl_2$ and DMP (1.78 g, 4.20 mmol) was added in batches, Reaction was performed at room temperature overnight under $N_2$ atmosphere. TLC monitoring of the reaction showed that the reaction was complete 40 mL of water was added to the reaction mixture, the mixture was extracted with EA (2×80 mL), the combined organic layers were washed with saturated NaCl, dried over anhydrous $Na_2SO_4$, and the solvent was distilled under reduced pressure to give crude product which was purified by flash chromatography on silica gel (eluent:PE/Acetone=40:1→30:1) to give KHC-7 as a white solid (0.62 g, 89.47% yield).

Compound KH021: $FeCl_3$ (0.61 g, 3.75 mmol) and LiCl (0.34 g, 8.07 mmol) were mixed and added into a 100 mL of three-necked flask under $N_2$ atmosphere, then anhydrous THF (40 mL) was added and the mixture was stirred at RT for 5 minutes. and cooled to −45° C. Then $CH_3MgBr$ (15.20 mL, 15.20 mmol) was added dropwise and the mixture was stirred at −40° C. for 15 minutes, then compound KHC-7 (0.62 g, 1.88 mmol) dissolved in anhydrous THF was added dropwise. The reaction was heated to about −20° C. and stirred for 2 hours. TLC monitoring of the reaction showed that the reaction was complete. The reaction solution was quenched with 40 mL saturated $NH_4Cl$ aqueous solution and the mixture was extracted with EA (2*80 mL). The combined organic layers were washed with saturated NaCl, dried over anhydrous $Na_2SO_4$, and the solvent was distilled under reduced pressure to give crude product which was purified by flash chromatography on silica gel (eluent:PE/acetone=40:1→35:1) to give a white solid KH021 (0.52 g, 78.50% yield).

$^1$H NMR (400 MHZ, $CDCl_3$) 2.29 (dd, 1H), 2.13 (s, 3H), 1.88-1.25 (m, 21H), 1.20 (s, 3H), 0.95 (s, 3H), 0.88-0.78 (m, 3H), 0.70 (s, 3H).

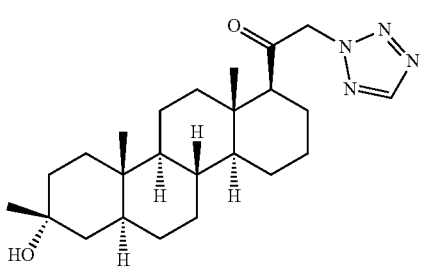
KH022

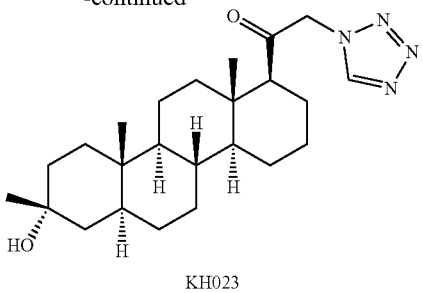

KH023

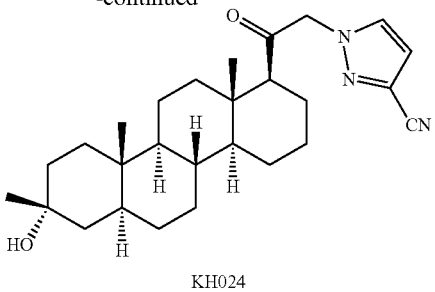

KH024

Compounds KHC-8 and KHC-9: Compound KH021 (1.25 g, 3.60 mmol) was dissolved in 40 mL of methanol until clear, then bromine (0.86 g, 5.40 mmol) was added dropwise. After 4 hours of reaction at room temperature, the reaction solution turned from orange to light yellow, and TLC monitoring showed that the reaction was complete. The reaction mixture was added with 30 ml of water, extracted with EA (2×65 mL), the combined organic layers were washed with saturated sodium chloride, dried over anhydrous sodium sulfate, and the solvent was distilled under reduced pressure to obtain a light yellow crude solid, which was purified by flash chromatography on silica gel (elute with dichloromethane) to obtain white solid KHC-8 (0.93 g, 60.78%) and white solid KHC-9 (0.36 g, 19.89%).

Compounds KH022 and KH023: Compound KHC-8 (100 mg, 0.24 mmol) was dissolved in 5 mL of acetonitrile until clear, $Cs_2CO_3$ (234 mg, 0.72 mmol) and 1H-tetrazole (50 mg, 0.72 mmol) were added. Reaction was performed at room temperature overnight, and TLC monitoring showed that the reaction was complete. The reaction mixture was added 10 ml of water, extracted with ethyl acetate (2×20 mL), the combined organic layers were washed with saturated sodium chloride, dried over anhydrous sodium sulfate, and the solvent was distilled under reduced pressure to obtain crude product. Thin layer chromatography with thick silica gel preparation plate was used for purification (elute with dichloromethane/methanol=30:1) to obtain a white solid KH022 (20 mg, 20.08%) and a white solid KH023 (47 mg, 47.19%), respectively.

$^1$H NMR (400 MHZ, $CDCl_3$) δ 8.56 (s, 1H), 5.54-5.45 (m, 2H), 2.35 (dd, 1H), 1.89-1.25 (m, 21H), 1.20 (s, 3H), 0.95 (s, 3H), 0.88-0.80 (m, 3H), 0.72 (s, 3H).

$^1$H NMR (400 MHZ, $CDCl_3$) δ 8.71 (s, 1H), 5.30 (dd, 2H), 2.35 (dd, 1H), 1.83-1.23 (m, 21H), 1.20 (s, 3H), 0.95 (s, 3H), 0.87-0.78 (m, 3H), 0.72 (s, 3H).

Example 21: Synthesis of Compound KH024

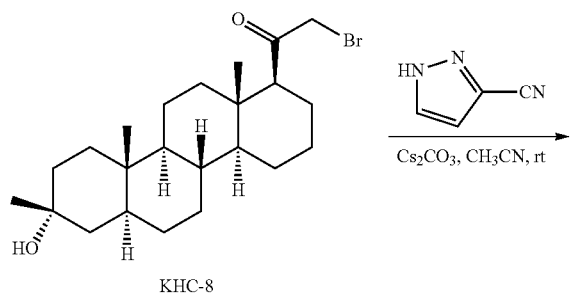

Compounds KH024: KHC-8 (60 mg, 0.14 mmol) was dissolved in $CH_3CN$ 5 mL, then $Cs_2CO_3$ (91 mg, 0.28 mmol) and 3-cyanopyrazole (26 mg, 0.28 mmol) was added, Reaction was performed at room temperature overnight. TLC monitoring showed that the reaction was complete, 10 ml water was added to the reaction mixture, the mixture was extracted with EA (2×20 mL), the combined organic layers were washed with saturated NaCl, dried over anhydrous $Na_2SO_4$, and the solvent was distilled under reduced pressure to give crude product which was purified by TLC (eluent:$CH_2Cl_2$/$CH_3OH$=40:1) to give a white solid KH024 (16 mg, 26.09%)

$^1$H NMR (400 MHZ, $CDCl_3$) 7.45 (d, 1H), 6.73 (d, 1H), 5.06 (q, 2H), 2.30 (dd, 1H), 1.86-1.23 (m, 21H), 1.20 (s, 3H), 0.95 (s, 3H), 0.87-0.77 (m, 3H), 0.72 (s, 3H).

Example 22: Synthesis of Compound KH025

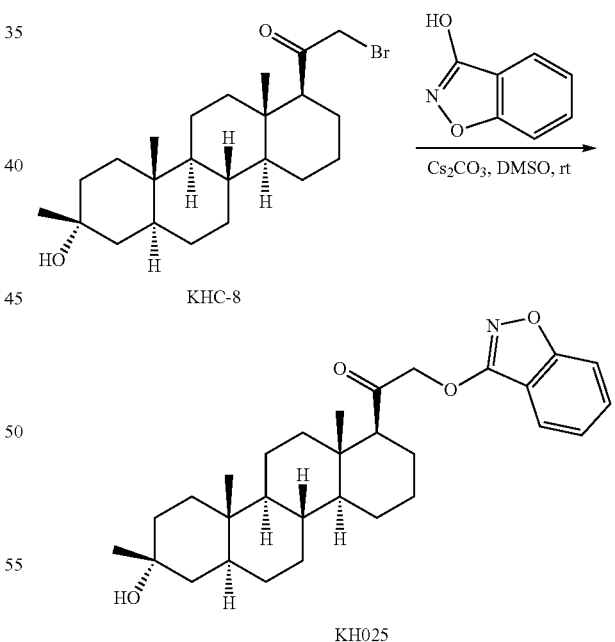

Compounds KH025: KHC-8 (100 mg, 0.24 mmol) was dissolved in DMSO 5 mL, then $Cs_2CO_3$ (235 mg, 0.72 mmol) and 3-hydroxybenzoisoxazole (97 mg, 0.72 mmol) was added, Reaction was performed at room temperature overnight. TLC monitoring showed that the reaction was complete, 10 ml water was added to the reaction mixture, the mixture was extracted with EA (2×20 mL), the combined organic layers were washed with saturated NaCl, dried over anhydrous Na$_2$SO$_4$, and the solvent was distilled under reduced pressure to give crude product which was purified by TLC (eluent:PE/acetone=5:1) to give a white solid KH025 (70 mg, 60.76%).

$^1$H NMR (400 MHZ, CDCl$_3$) δ 7.72 (d, 1H), 7.58-7.49 (m, 1H), 7.42 (d, 1H), 7.29 (d, 1H), 5.11-4.95 (m, 2H), 2.35 (dd, 1H), 1.87-1.22 (m, 21H), 1.20 (s, 3H), 0.99 (s, 3H), 0.87-0.80 (m, 3H), 0.72 (s, 3H).

Example 23: Synthesis of Compound KH026

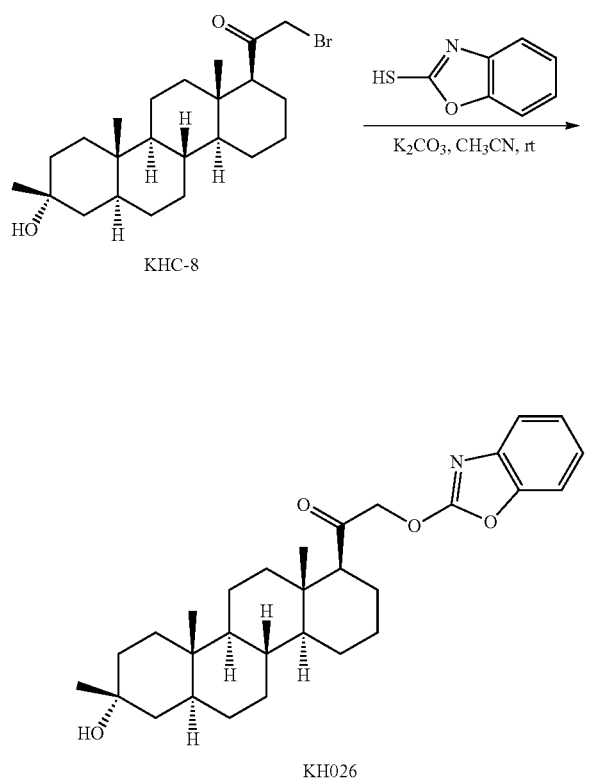

Compounds KH026: KHC-8 (53 mg, 0.12 mmol) was dissolved in CH$_3$CN 5 mL, then K$_2$CO$_3$ (100 mg, 0.72 mmol) and 2-mercaptobenzoxazole (24 mg, 0.16 mmol) was added, Reaction was performed at room temperature overnight. TLC monitoring showed that the reaction was complete, 10 ml water was added to the reaction mixture, the mixture was extracted with EA (2×20 mL), the combined organic layers were washed with saturated NaCl, dried over anhydrous Na$_2$SO$_4$, and the solvent was distilled under reduced pressure to give crude product which was purified by TLC (eluent:PE/acetone=6:1) to give a white solid KH026 (30 mg, 50.40%).

$^1$H NMR (400 MHZ, CDCl$_3$) δ 7.55 (d, 1H), 7.42 (d, 1H), 7.34-7.24 (m, 2H), 4.33 (m, 2H), 2.54 (dd, 1H), 1.83-1.23 (m, 21H), 1.18 (s, 3H), 0.94 (s, 3H), 0.85-0.78 (m, 3H), 0.70 (s, 3H).

Example 24: Synthesis of Compound KH027

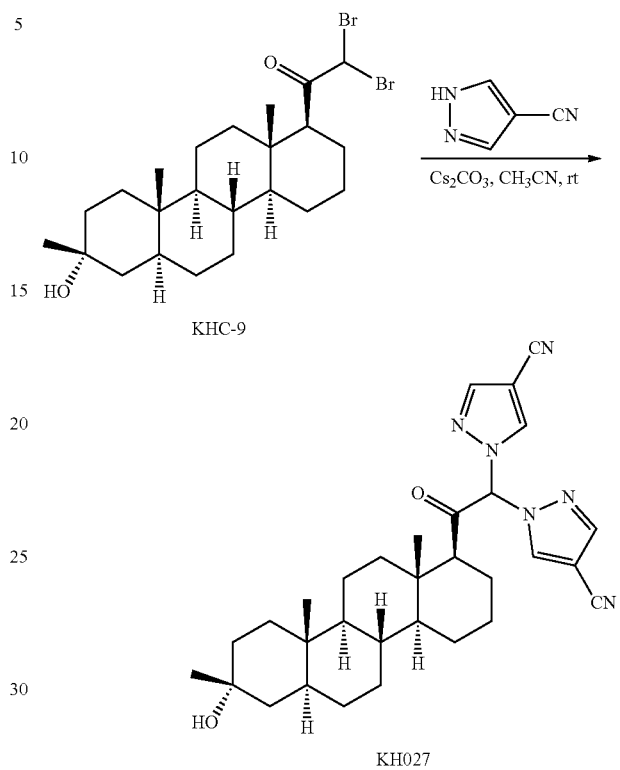

Compounds KH027: KHC-9 (110 mg, 0.22 mmol) was dissolved in 10 mL CH$_3$CN, then Cs$_2$CO$_3$ (215 mg, 0.66 mmol) and 4-cyanopyrazole (61 mg, 0.66 mmol) was added, Reaction was performed at room temperature overnight. TLC monitoring showed that the reaction was complete, 10 ml water was added to the reaction mixture, the mixture was extracted with EA (2×20 mL), the combined organic layers were washed with saturated NaCl, dried over anhydrous Na$_2$SO$_4$, and the solvent was distilled under reduced pressure to give crude product which was purified by TLC (eluent:CH$_2$Cl$_2$/CH$_3$OH=6:1) to give a white solid KH027 (76 mg, 65.30%).

$^1$H NMR (400 MHZ, CDCl$_3$) δ 8.23 (s, 1H), 8.13 (s, 1H), 7.92 (s, 1H), 7.83 (s, 1H), 7.03 (s, 1H), 2.11 (dd, 1H), 1.83-1.23 (m, 21H), 1.20 (s, 3H), 0.91 (s, 3H), 0.82-0.75 (m, 3H), 0.70 (s, 3H).

Example 25: Synthesis of Compound KH028

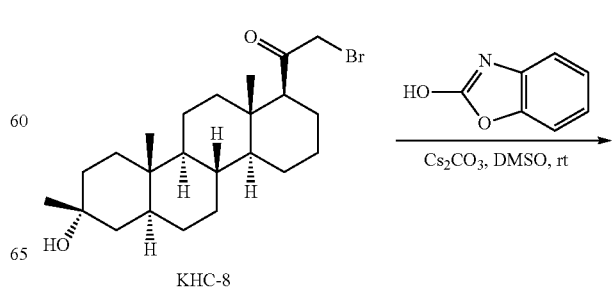

-continued

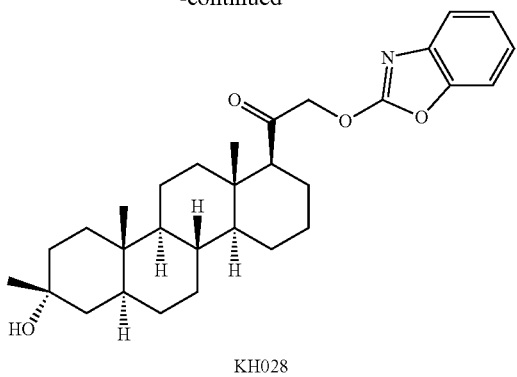
KH028

Compounds KH028: KHC-8 (70 mg, 0.16 mmol) was dissolved in 8 mL DMSO, then $Cs_2CO_3$ (160 mg, 0.49 mmol) and 2-hydroxybenzoxazole (66 mg, 0.49 mmol) was added, Reaction was performed at room temperature overnight. TLC monitoring showed that the reaction was complete 10 ml of water was added to the reaction mixture, the mixture was extracted with EA (2×20 mL), the combined organic layers were washed with saturated NaCl, dried over anhydrous $Na_2SO_4$, and the solvent was distilled under reduced pressure to give crude product which was purified by TLC (eluent:$CH_2Cl_2$/$CH_3OH$=60:1) to give a white solid KH028 (55 mg, 71.61%).

$^1$H NMR (400 MHZ, CDCl$_3$) δ 7.24-7.18 (m, 1H), 7.17-7.06 (m, 2H), 6.75-6.64 (m, 1H), 4.58 (dd, 2H), 2.38 (dd, 1H), 1.92-1.22 (m, 21H), 1.20 (s, 3H), 0.97 (s, 3H), 0.89-0.78 (m, 3H), 0.72 (s, 3H).

Example 26: Synthesis of Compound KH029

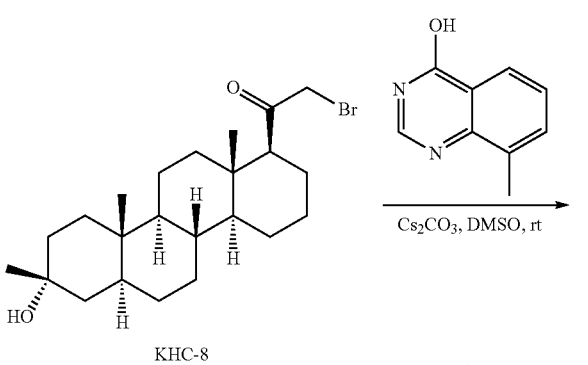
KHC-8

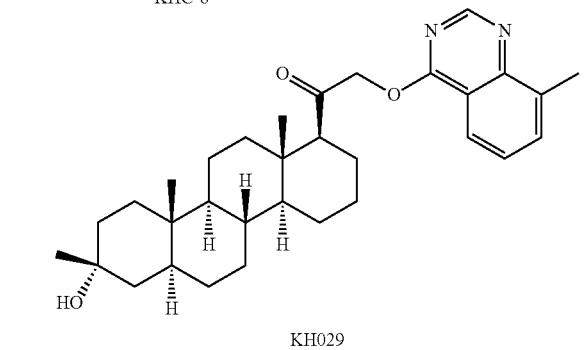
KH029

Compounds KH029: KHC-8 (60 mg, 0.14 mmol) was dissolved in 5 mL DMSO, then $Cs_2CO_3$ (138 mg, 0.42 mmol) and 8-methyl-4-hydroxyquinazoline (68 mg, 0.42 mmol) was added. Reaction was performed at room temperature overnight. TLC monitoring showed that the reaction was complete, 10 ml of water was added to the reaction mixture, the mixture was extracted with EA (2×20 mL), the combined organic layers were washed with saturated NaCl, dried over anhydrous $Na_2SO_4$, and the solvent was distilled under reduced pressure to give crude product which was purified by TLC (eluent:$CH_2Cl_2$/$CH_3OH$=60:1) to give a white solid KH029 (50 mg, 70.72%).

$^1$H NMR (400 MHZ, CDCl$_3$) δ 8.13 (d, 1H), 7.90 (s, 1H), 7.61 (d, 1H), 7.39 (t, 1H), 4.81 (s, 2H), 2.63 (s, 3H), 2.43 (dd, 1H), 1.88-1.22 (m, 21H), 1.20 (s, 3H), 0.97 (s, 3H), 0.90-0.81 (m, 3H), 0.72 (s, 3H).

Example 27: Synthesis of Compound KH030

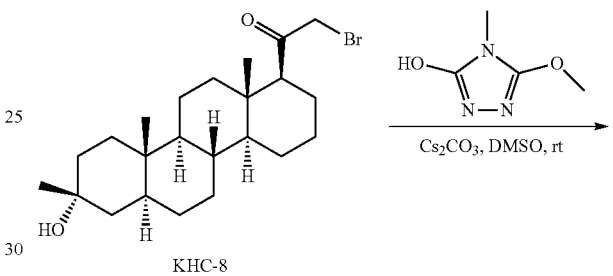
KHC-8

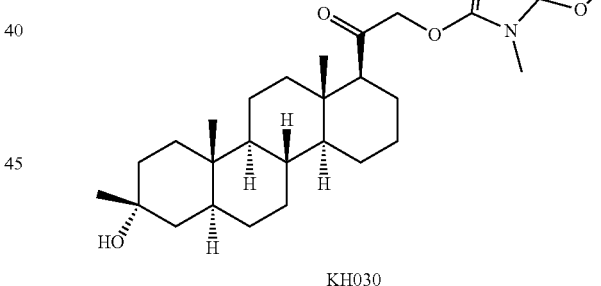
KH030

Compounds KH030: KHC-8 (50 mg, 0.12 mmol) was dissolved in 5 mL DMSO, then $Cs_2CO_3$ (78 mg, 0.24 mmol) and 3-hydroxy-4-methyl-5-methoxy-4H-1, 2, 4-triazole (31 mg, 0.24 mmol) was added, Reaction was performed at room temperature overnight. TLC monitoring showed that the reaction was complete 10 ml of water was added to the reaction mixture, the mixture was extracted with EA (2×20 mL), the combined organic layers were washed with saturated NaCl, dried over anhydrous $Na_2SO_4$, and the solvent was distilled under reduced pressure to give crude product which was purified by TLC (eluent:PE/acetone=4:1) to give a white solid KH030 (20 mg, 35.16%).

$^1$H NMR (400 MHZ, CDCl$_3$) δ 4.47 (q, 2H), 3.93 (s, 3H), 3.12 (s, 3H), 2.28 (dd, 1H), 1.86-1.22 (m, 21H), 1.19 (s, 3H), 0.94 (s, 3H), 0.85-0.78 (m, 3H), 0.70 (s, 3H).

Example 28: Synthesis of Compound KH031

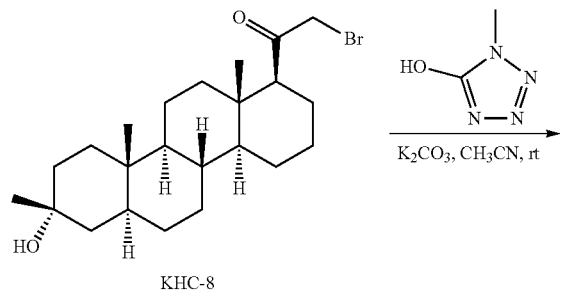

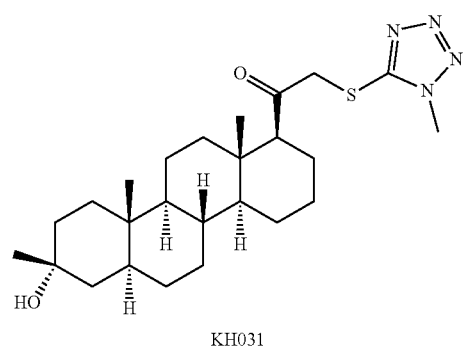

Compounds KH031: KHC-8 (60 mg, 0.14 mmol) was dissolved in 5 mL CH$_3$CN, then K$_2$CO$_3$ (58 mg, 0.42 mmol) and 1-methyl-5-mercapto-1H-tetrazole (68 mg, 0.42 mmol) was added, Reaction was performed at room temperature. TLC monitoring showed that the reaction was complete, 10 ml water was added to the reaction mixture, the mixture was extracted with EA (2×20 mL), the combined organic layers were washed with saturated NaCl, dried over anhydrous Na$_2$SO$_4$, and the solvent was distilled under reduced pressure to give crude product which was purified by TLC (eluent:PE/acetone=4:1) to give a white solid KH031 (50 mg, 77.47%).

$^1$H NMR (400 MHZ, CDCl$_3$) 4.40 (dd, 2H), 3.97 (s, 3H), 2.47 (dd, 1H), 1.88-1.22 (m, 21H), 1.19 (s, 3H), 0.93 (s, 3H), 0.87-0.79 (m, 3H), 0.71 (s, 3H).

Example 29: Synthesis of Compound KH032

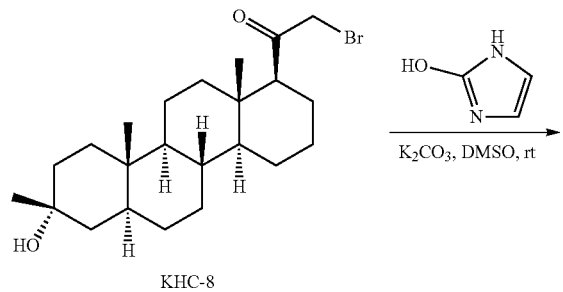

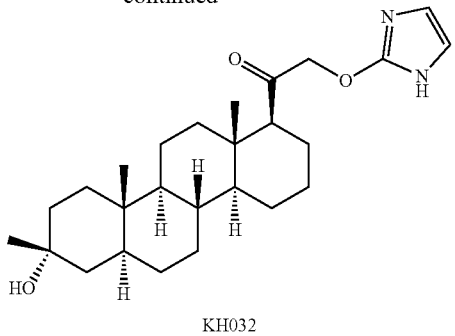

Compounds KH032: KHC-8 (50 mg, 0.12 mmol) was dissolved in 5 mL DMSO, then K$_2$CO$_3$ (50 mg, 0.36 mmol) and 1-hydroxy-1H-imidazole (30 mg, 0.36 mmol) was added, Reaction was performed at room temperature overnight. TLC monitoring of the reaction showed that the reaction was complete., 10 ml of water was added to the reaction mixture, the mixture was extracted with EA (2×20 mL), the combined organic layers were washed with saturated NaCl, dried over anhydrous Na$_2$SO$_4$, and the solvent was distilled under reduced pressure to give crude product which was purified by TLC (eluent:PE/acetone=2:1) to give a white solid KH032 (11 mg, 21.37%).

$^1$H NMR (400 MHZ, CDCl$_3$) δ 9.26 (s, 1H), 6.32 (s, 1H), 6.17 (s, 1H), 4.53-4.32 (m, 2H), 2.31 (dd, 1H), 1.86-1.25 (m, 21H), 1.21 (s, 3H), 0.95 (s, 3H), 0.88-0.78 (m, 3H), 0.71 (s, 3H).

Example 30: Synthesis of Compound KH033

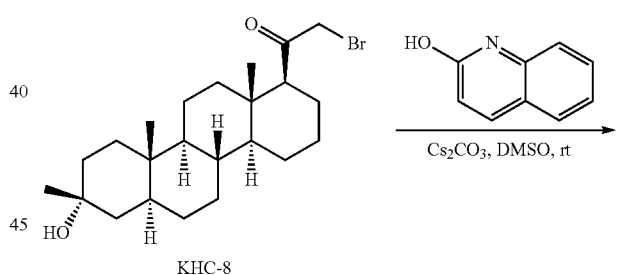

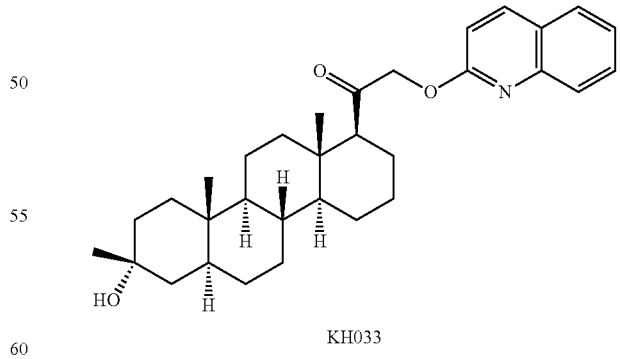

Compounds KH033: KHC-8 (60 mg, 0.14 mmol) was dissolved in 5 mL DMSO, then Cs$_2$CO$_3$ (138 mg, 0.42 mmol) and 2-hydroxyquinoline (61 mg, 0.42 mmol) was added, Reaction was performed at room temperature overnight. TLC monitoring of the reaction showed that the reaction was complete., 10 ml of water was added to the reaction mixture, the mixture was extracted with EA (2×20 mL), the combined organic layers were washed with saturated NaCl, dried over anhydrous Na₂SO₄, and the solvent was distilled under reduced pressure to give crude product which was purified by TLC (eluent:PE/acetone=4:1) to give a white solid KH033 (15 mg, 21.87%).

¹H NMR (400 MHZ, CDCl₃) δ 8.05 (d, 1H), 7.75 (dd, 2H), 7.61 (t, 1H), 7.39 (t, 1H), 7.05 (d, 1H), 5.15 (s, 2H), 2.43 (dd, 1H), 1.98-1.23 (m, 21H), 1.21 (s, 3H), 0.97 (s, 3H), 0.91-0.78 (m, 3H), 0.74 (s, 3H).

Example 31: Synthesis of Compound KH034

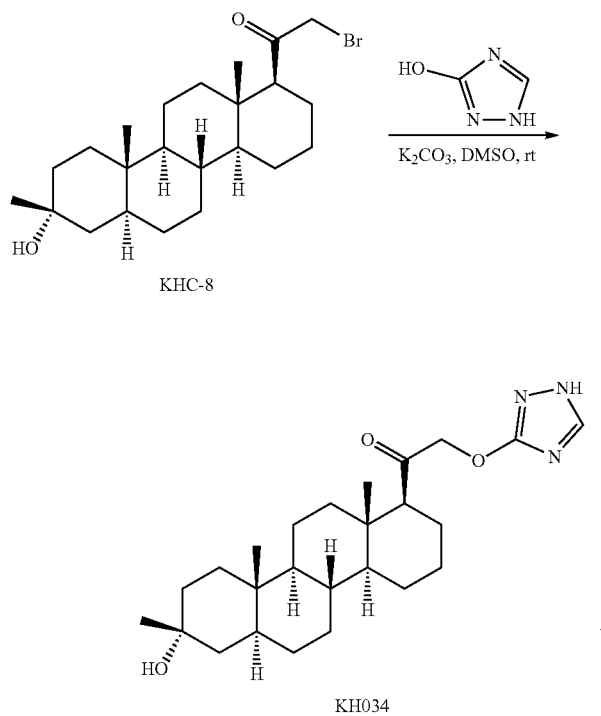

Compounds KH034: KHC-8 (60 mg, 0.14 mmol) was dissolved in DMSO 5 mL, then K₂CO₃ (58 mg, 0.42 mmol) and 3-hydroxy-1H-1, 2, 4-triazole (36 mg, 0.42 mmol) was added, Reaction was performed at room temperature overnight. TLC monitoring of the reaction showed that the reaction was complete., 10 ml of water was added to the reaction mixture, the mixture was extracted with EA (2×20 mL), the combined organic layers were washed with saturated NaCl, dried over anhydrous Na₂SO₄, and the solvent was distilled under reduced pressure to give crude product which was purified by TLC (eluent:CH₂Cl₂/CH₃OH=40:1) to give a white solid KH034 (40 mg, 66.45%).

¹H NMR (400 MHZ, CDCl₃) δ 9.30 (s, 1H), 7.42 (s, 1H), 4.47 (q, 2H), 2.33 (dd, 1H), 1.87-1.25 (m, 21H), 1.20 (s, 3H), 0.95 (s, 3H), 0.87-0.79 (m, 3H), 0.71 (s, 3H).

Example 32: Synthesis of Compound KH035

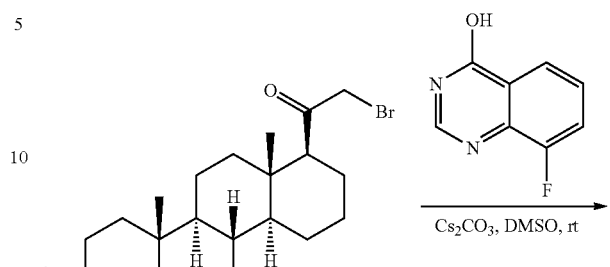

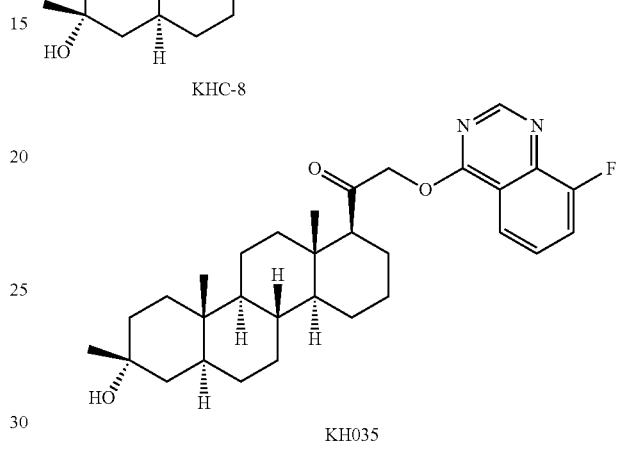

Compounds KH035: KHC-8 (80 mg, 0.19 mmol) was dissolved in DMSO 6 mL, then Cs₂CO₃ (184 mg, 0.56 mmol) and 8-fluoro-4-hydroxyquinazoline (92 mg, 0.56 mmol) was added, Reaction was performed at room temperature overnight. TLC monitoring of the reaction showed that the reaction was complete., 10 ml of water was added to the reaction mixture, the mixture was extracted with EA (2×20 mL), the combined organic layers were washed with saturated NaCl, dried over anhydrous Na₂SO₄, and the solvent was distilled under reduced pressure to give crude product which was purified by TLC (eluent:PE/acetone=2:1) to give a white solid KH035 (65 mg, 67.21%).

¹H NMR (400 MHz, CDCl₃) δ 8.06 (d, 1H), 7.88 (s, 1H), 7.55-7.40 (m, 2H), 4.79 (m, 2H), 2.43 (dd, 1H), 1.88-1.22 (m, 21H), 1.21 (s, 3H), 0.96 (s, 3H), 0.90-0.81 (m, 3H), 0.72 (s, 3H).

Example 33: Synthesis of Compound KH036

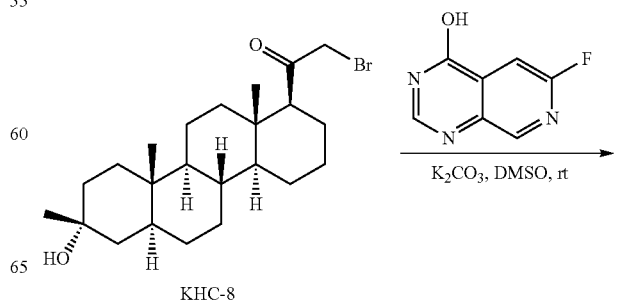

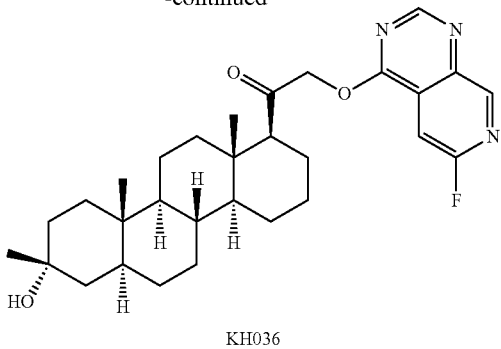

KH036

Compounds KH036: KHC-8 (60 mg, 0.14 mmol) was dissolved in DMSO 5 mL, then $K_2CO_3$ (58 mg, 0.42 mmol) and 6-fluoropyridine [3,4-d] Pyrimidin-4-one (69 mg, 0.42 mmol) was added, Reaction was performed at room temperature overnight. TLC monitoring of the reaction showed that the reaction was complete., 10 ml of water was added to the reaction mixture, the mixture was extracted with EA (2×20 mL), the combined organic layers were washed with saturated NaCl, dried over anhydrous $Na_2SO_4$, and the solvent was distilled under reduced pressure to give crude product which was purified by TLC (eluent:$CH_2Cl_2$/$CH_3OH$=40:1) to give a white solid KH036 (40 mg, 56.02%).

$^1$H NMR (400 MHZ, $CDCl_3$) δ 8.82 (s, 1H), 7.80 (s, 1H), 7.66 (d, 1H), 4.80 (q, 2H), 2.43 (dd, 1H), 1.89-1.23 (m, 21H), 1.20 (s, 3H), 0.95 (s, 3H), 0.90-0.80 (m, 3H), 0.71 (s, 3H).

Example 34: Synthesis of Compound KH037

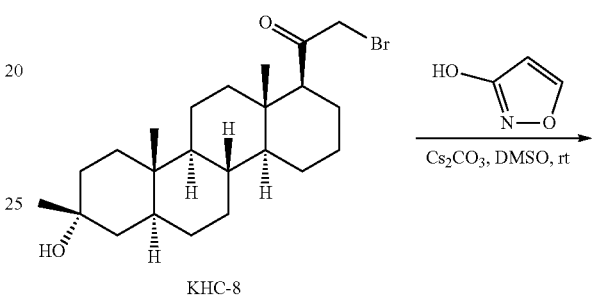

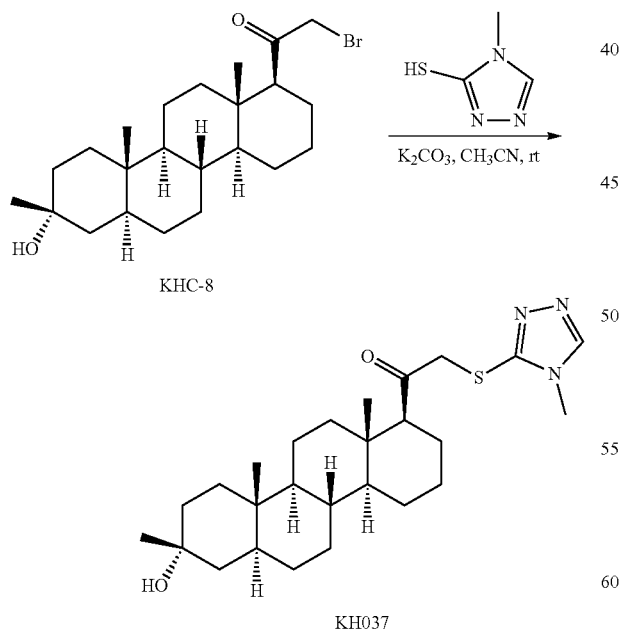

KH037

Compounds KH037: KHC-8 (60 mg, 0.14 mmol) was dissolved in $CH_3CN$ 5 mL, then $K_2CO_3$ (58 mg, 0.42 mmol) and 4-methyl-4H-3-mercapto-1, 2, 4-triazole (49 mg, 0.42 mmol) was added, Reaction was performed at room temperature overnight. TLC monitoring of the reaction showed that the reaction was complete., 10 ml of water was added to the reaction mixture, the mixture was extracted with EA (2×20 mL), the combined organic layers were washed with saturated NaCl, dried over anhydrous $Na_2SO_4$, and the solvent was distilled under reduced pressure to give crude product which was purified by TLC (eluent:PE/acetone=3:2) to give a white solid KH037 (53 mg, 82.30%).

$^1$H NMR (400 MHZ, $CDCl_3$) δ 8.16 (s, 1H), 4.34 (dd, 2H), 3.65 (s, 3H), 2.45 (dd, 1H), 1.88-1.22 (m, 21H), 1.19 (s, 3H), 0.91 (s, 3H), 0.87-0.79 (m, 3H), 0.70 (s, 3H).

Example 35: Synthesis of Compound KH038

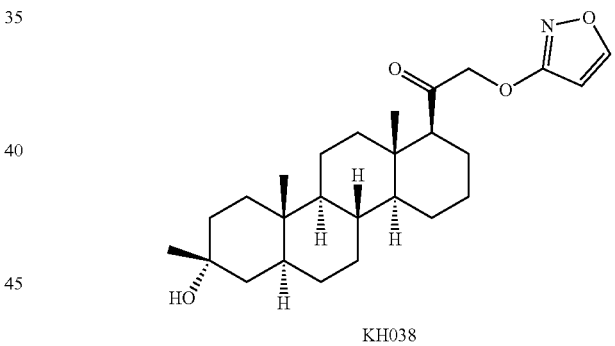

KH038

Compounds KH038: KHC-8 (60 mg, 0.14 mmol) was dissolved in DMSO 5 mL, then $Cs_2CO_3$ (138 mg, 0.42 mmol) and 3-hydroxyisoxazole (36 mg, 0.42 mmol) was added, Reaction was performed at room temperature overnight. TLC monitoring of the reaction showed that the reaction was complete., 10 ml of water was added to the reaction mixture, the mixture was extracted with EA (2×20 mL), the combined organic layers were washed with saturated NaCl, dried over anhydrous $Na_2SO_4$, and the solvent was distilled under reduced pressure to give crude product which was purified by TLC (eluent:PE/acetone=15:1) to give a white solid KH038 (39 mg, 65.00%).

$^1$H NMR (300 MHZ, $CDCl_3$) δ 8.12 (d, 1H), 6.06 (d, 1H), 4.87 (s, 2H), 2.29 (dd, 1H), 1.90-1.22 (m, 21H), 1.20 (s, 3H), 0.97 (s, 3H), 0.90-0.74 (m, 3H), 0.71 (s, 3H).

Example 36: Synthesis of Compound KH039

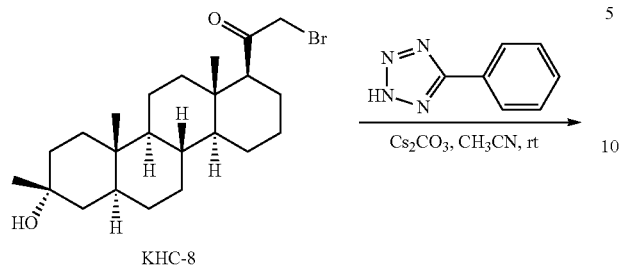

KHC-8

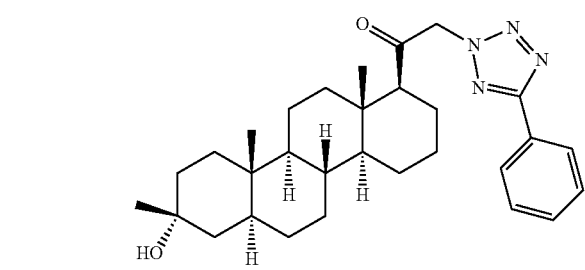

KH039

Compounds KH039: KHC-8 (75 mg, 0.18 mmol) was dissolved in CH₃CN 5 mL, then Cs₂CO₃ (171 mg, 0.53 mmol) and 5-phenyltetrazole (77 mg, 0.53 mmol) was added, Reaction was performed at room temperature overnight. TLC monitoring of the reaction showed that the reaction was complete., 10 ml of water was added to the reaction mixture, the mixture was extracted with EA (2×20 mL), the combined organic layers were washed with saturated NaCl, dried over anhydrous Na₂SO₄, and the solvent was distilled under reduced pressure to give crude product which was purified by TLC (eluent:PE/acetone=3:1) to give a white solid KH039 (79 mg, 89.39%).

$^1$H NMR (400 MHZ, CDCl₃) δ 8.19-8.07 (m, 2H), 7.55-7.42 (m, 3H), 5.54-5.40 (m, 2H), 2.37 (dd, 1H), 1.92-1.23 (m, 21H), 1.21 (s, 3H), 0.97 (s, 3H), 0.90-0.78 (m, 3H), 0.73 (s, 3H).

Example 37: Synthesis of Compound KH040

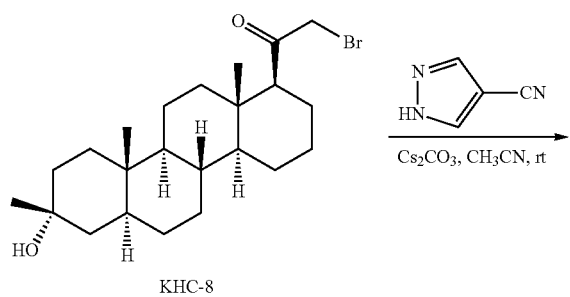

KHC-8

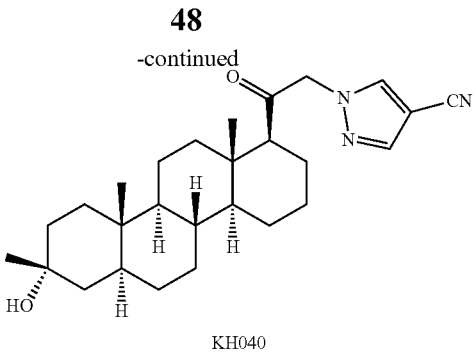

KH040

Compounds KH040: KHC-8 (60 mg, 0.14 mmol) was dissolved in CH₃CN 5 mL, then Cs₂CO₃ (91 mg, 0.28 mmol) and 4-cyanopyrazole (26 mg, 0.28 mmol) was added, Reaction was performed at room temperature overnight. TLC monitoring of the reaction showed that the reaction was complete., 10 ml of water was added to the reaction mixture, the mixture was extracted with EA (2×20 mL), the combined organic layers were washed with saturated NaCl, dried over anhydrous Na₂SO₄, and the solvent was distilled under reduced pressure to give crude product which was purified by TLC (eluent:CH₂Cl₂/CH₃OH=40:1) to give a white solid KH040 (16 mg, 26.09%).

$^1$H NMR (400 MHZ, CDCl₃) δ 7.82 (s, 1H), 7.81 (s, 1H), 5.00 (q, 2H), 2.32 (dd, 1H), 1.88-1.22 (m, 21H), 1.20 (s, 3H), 0.94 (s, 3H), 0.87-0.79 (m, 3H), 0.71 (s, 3H).

Example 38: Synthesis of Compound KH041

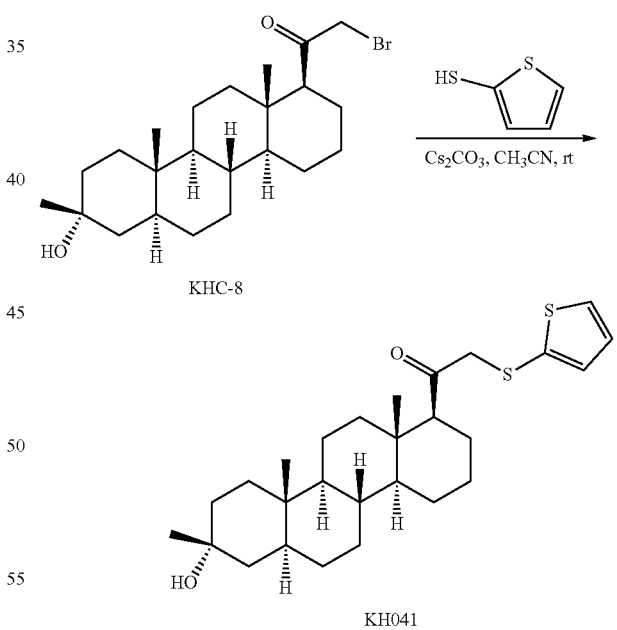

Compounds KH041: KHC-8 (70 mg, 0.16 mmol) was dissolved in 5 mL CH₃CN, then Cs₂CO₃ (160 mg, 0.49 mmol) and 2-mercaptothiophene (57 mg, 0.49 mmol) was added, Reaction was performed at room temperature overnight. TLC monitoring of the reaction showed that the reaction was complete., 10 ml of water was added to the reaction mixture, the mixture was extracted with EA (2×20 mL), the combined organic layers were washed with saturated NaCl, dried over anhydrous Na₂SO₄, and the solvent was distilled under reduced pressure to give crude product which was purified by TLC (eluent:CH$_2$Cl$_2$/PE=1:1) to give a grey solid KH041 (27 mg, 35.53%).

$^1$H NMR (400 MHZ, CDCl$_3$) δ 7.35 (dd, 1H), 7.14 (dd, 1H), 6.95 (dd, 1H), 3.62 (dd, 2H), 1.90-1.21 (m, 21H), 1.20 (s, 3H), 0.90 (s, 3H), 0.84-0.74 (m, 3H), 0.70 (s, 3H).

Example 39: Synthesis of Compound KH042

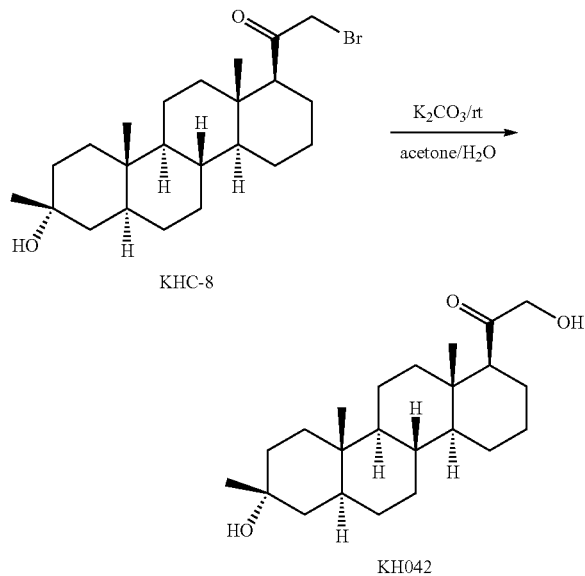

Compounds KH042: KHC-8 (150 mg, 0.35 mmol) was dissolved in 15 ml of water and 30 ml of acetone, then K$_2$CO$_3$ (49 mg, 0.35 mmol) was added, Reaction was performed at room temperature overnight. TLC monitoring of the reaction showed that the reaction was complete., 10 ml of water was added to the reaction mixture, the mixture was extracted with EA (2×30 mL), the combined organic layers were washed with saturated NaCl, dried over anhydrous Na$_2$SO$_4$, and the solvent was distilled under reduced pressure to give crude product which was purified by TLC (eluent:CH$_2$Cl$_2$/CH$_3$OH=50:1) to give a white solid KH042 (21 mg, 16.54%). $^1$H NMR (400 MHZ, DMSO-d6) δ 4.92 (t, 1H), 4.06-4.04 (m, 2H), 3.85 (t, 1H), 2.27 (dd, 1H), 1.82-1.10 (m, 21H), 1.05 (s, 3H), 0.87 (s, 3H), 0.85-0.70 (m, 3H), 0.65 (s, 3H).

Example 39: Synthesis of Compound KH043 and KH044

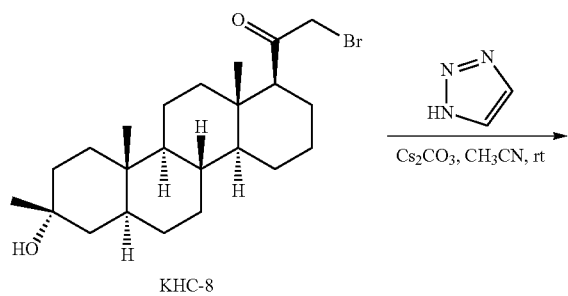

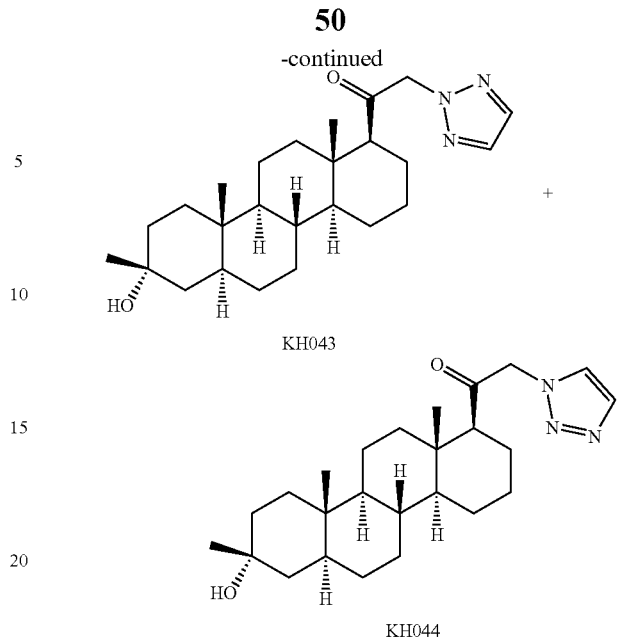

Compounds KH043 and KH044: KHC-8 (60 mg, 0.14 mmol) was dissolved in 5 ml CH$_3$CN, then Cs$_2$CO$_3$ (91 mg, 0.28 mmol) and 1H-triazole (15 mg, 0.21 mmol) was added, Reaction was performed at room temperature overnight. TLC monitoring of the reaction showed that the reaction was complete., 10 ml of water was added to the reaction mixture, the mixture was extracted with EA (2×20 mL), the combined organic layers were washed with saturated NaCl, dried over anhydrous Na$_2$SO$_4$, and the solvent was distilled under reduced pressure to give crude product which was purified by TLC (eluent:CH$_2$Cl$_2$/CH$_3$OH=40:1) to give a white solid KH6070100-1 (12 mg, 20.70%) and a white solid KH6070100-2 (27 mg, 46.58%) respectively.

$^1$H NMR (400 MHZ, CDCl$_3$) δ 7.68 (s, 2H), 5.34-5.20 (m, 2H), 2.25 (dd, 1H), 1.88-1.23 (m, 21H), 1.20 (s, 3H), 0.95 (s, 3H), 0.89-0.79 (m, 3H), 0.71 (s, 3H).

$^1$H NMR (400 MHZ, CDCl$_3$) δ 7.76 (s, 1H), 7.61 (s, 1H), 5.25 (dd, 2H), 2.37 (dd, 1H), 1.86-1.22 (m, 21H), 1.20 (s, 3H), 0.94 (s, 3H), 0.86-0.76 (m, 3H), 0.71 (s, 3H).

Example 40: Synthesis of Compound KH045

Compounds KHC-11: Compound KHC-10 (150.0 g, 183.8 mmol) was dissolved in THF 500 mL and 10% Pd/C (6.0 g) was added to the solution. Then the solution was hydrogenate under H$_2$ atmosphere and kept stirring at RT for 24 hours, subsequently filtered, The filtrate was concentrated under vacuum, to obtain crude product which was subsequently stirred with solvent (eluent:PE:acetone=1:1) to obtain compound KHC-11 (150.0 g, 99.26% yield).

Compound KHC-12: KHC-11 (150.0 g, 547.4 mmol) was dissolved in 1000 mL CH$_3$OH, then 12 (14.0 g, 54.8 mmol) was added to the solution, the solution was heated to 60° C. and kept stirring for 12 hours, Then it was concentrated under vacuum and the residue was, purified by silica gel column flash chromatography (eluent:PE:EA=10:1) to obtain a white solid KHC-12 (130.0 g, 74.20%).

Compound KHC-13: KHC-12 (130.0 g, 406.2 mmol) was dissolved in 1000 mL DMF, and t-BuOK (91.0 g, 812.4 mmol) trimethyl iodonium sulfide (165.8 g, 812.7 mmol) was added to the solution, the solution kept stirring at RT for 12 hours under N$_2$·atmosphere Then brine was added to the reaction mixture, the mixture was extracted with EA (3×1

L), the organic layers were combined, and concentrated under vacuum to obtain a white solid KHC-13 (120.0 g, 88.50%).

Compound KHC-14: KHC-13 (120.0 g, 359.4 mmol) was dissolved in 900 mL ethanol and 160 ml of water NaN$_3$ (70.2 g, 1077.9 mmol) and NH$_4$Cl (67.2 g, 1257.9 mmol) was added to the solution, the solution kept stirring at 90° C. overnight. Brine was added to the reaction mixture, the mixture was extracted with EA (3×1 L), the organic layers were combined and concentrated under vacuum, The residue was purified by silica gel column flash chromatography (eluent:PE:EA=10:1) to obtain a white solid KHC-14 (130.0 g, 95.59%).

Compound KHC-15: KHC-14 (125.6 g, 332.4 mmol) was dissolved in 1000 mL CH$_3$CN, NaI (249.3 g, 1662.0 mmol) was added to the solution, the solution kept, stirring at RT for half an hour, then TMSCl (144.9, 1329.6 mmol) was added dropwise to the reaction solution and the reaction kept stirring at RT for 4 hours. Brine was added to the reaction mixture, the mixture was extracted with EA (3×1 L), the organic layers were combined and concentrated under vacuum, The residue was purified by silica gel column flash chromatography (eluent:PE:EA=10:1) to obtain a white solid KHC-15 (72.0 g, 75.20%). Compound KHC-16: KHC-15 (72.0 g, 250.0 mmol) was dissolved in 1000 mL CH$_3$OH, 12 (19.0 g, 75.0 mmol) was added to the solution, the reaction solution was heated to 60° C. and kept stirring for 12 hours, then the reaction mixture was concentrated under vacuum, The residue was purified by silica gel column flash chromatography (eluent:PE:EA=10:1) to obtain a white solid KHC-16 (53.0 g, 63.50%).

Compound KHC-17: Taking trimethylsilyl acetylene (77.8 g, 793.0 mmol) into 1000 mL THF, n-butyl lithium solution (1.6m, 329.0 mmol, 205.6 ml) was added at −78° cand the reaction solution kept stirring for 2 hours. Then compound KHC-16 (53.0 g, 158.6 mmol) in 400 mL THF was added into the reaction solution. The mixture was stirred at −78° C. for 2 hours and was gradually heated to 0° C., then it was poured into saturated NH$_4$Cl solution, and the mixture was extracted with EA (800 mL×3). The organic layers were combined and was concentrated under vacuum, the residue was purified by chromatography column (eluent: PE:EA=10:1) to obtain a white solid KHC-17 (56.0 g, 81.55%).

Compound KHC-18: KHC-17 (56.0 g, 129.3 mmol) in 800 mL THF, were mixed with 1.0M TBAF (129.3 mmol, 129.3 ml) at 0° C. and the mixture kept stirring for 1 hours. Brine was added to the reaction mixture, the mixture was extracted with EA (3×1 L). The organic layers were combined and was concentrated under vacuum, the residue was purified by silica gel column flash chromatography (eluent: PE:EA=5:1) to obtain a white solid KHC-18 (43.0 g, 92.30%).

Compound KHC-19: KHC-18 (38.0 g, 105.6 mmol) in 800 mL THF, were mixed with 1.0M HCl to PH=3 and the mixture kept stirring at RT for 12 hours. Brine (1.0 L) was added to the reaction mixture, the mixture was extracted with EA (3×1 L) The organic layers were combined and was concentrated under vacuum. The residue was subsequently purified by silica gel column flash chromatography (eluent: PE:EA=5:1) to obtain a white solid KHC-19 (32.0 g, 96.50%).

Compound KHC-20; and methanesulfonic acid (148.0 g, 1541.6 mmol) were mixed with 1000 mL CH$_2$Cl$_2$, KHC-19 (32.0 g, 101.9 mmol) in CH$_2$Cl$_2$ 1000 ml was added dropwise to the solution, the reaction solution kept stirring at 60° C. for 2 hours and was cooled to RT. Brine (1.0 L) was added to the reaction mixture, the mixture was extracted with CH$_2$Cl$_2$ (3×1.0 L) The organic layers were combined and was concentrated under vacuum. The residue was purified by silica gel column flash chromatography (eluent:PE: EA=10:1) to obtain a white solid KHC-20 (20.0 g, 62.50%).

Compound KHC-21: Compound KHC-20 (20.0 g, 63.7 mmol) was dissolved in 500 mL THF and 10% Pd/C (3.0 g) was added to the solution. Then the solution was hydrogenated under H$_2$ atmosphere. The reaction solution kept stirring at RT for 2 days, then filtered, The filtrate was concentrated under vacuum, to obtain crude product which was subsequently purified by silica gel column flash chromatography (eluent:PE:EA=15:1) to obtain a white solid KHC-21 (17.0 g, 84.40%). Compound KH045: To a mixture of FeCl$_3$ (23.0 g, 142.0 mmol) and LiCl (13.5 g, 321.4 mmol) in a 2000 mL three-necked flask under N$_2$, 800 mL anhydrous THF was added, the mixture kept stirring at RT for 20 minutes, then cooled to −40° C., CH$_3$MgBr (3M, 190ML, 570.0 mmol) was dropwise added to the solution, then the solution kept stirring at −40° C. for 30 min. KHC-21 (17.0 g, 53.8 mmol) in anhydrous THF (200 mL) was dropwise add to the above reaction solution, then the solution was heated to −20° C. and kept stirring for 4 hours. TLC monitoring of the reaction showed that the reaction was complete., the reaction solution was quenched with saturated NH$_4$Cl (40 mL) and the mixture was extracted with EA (3×1.0 L). The combined organic layers were washed with saturated brine I, dried over anhydrous Na$_2$SO$_4$, and concentrated under vacuum to obtain crude product which was subsequently purified by flash chromatography on silica gel (eluent:PE/EA=15:1) to give a white solid KH045 (10.2 g, 57.10% yield).

$^1$H NMR (400 MHZ, CDCl$_3$) δ 2.34-2.25 (m, 1H), 2.14 (s, 3H), 2.00 (t, J=11.4 Hz, 1H), 1.87-1.78 (m, 1H), 1.75-1.54 (m, 9H), 1.51-1.43 (m, 2H), 1.39-1.30 (m, 4H), 1.27-1.13 (m, 7H), 1.09-0.84 (m, 8H).

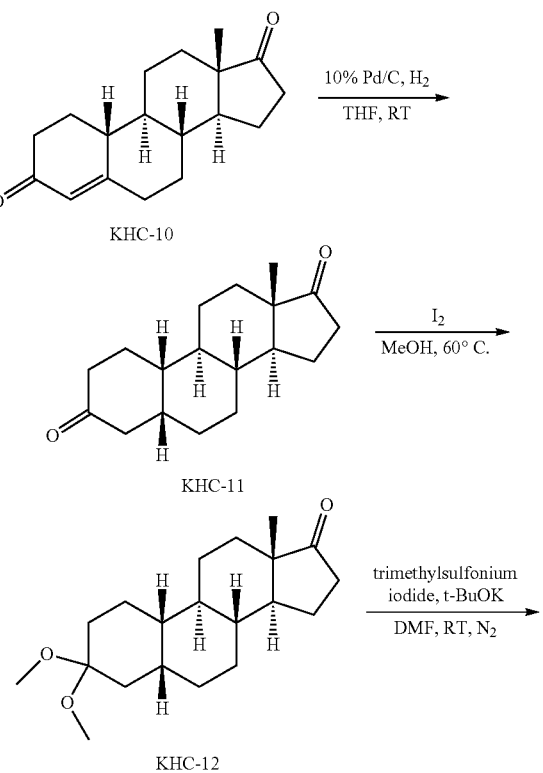

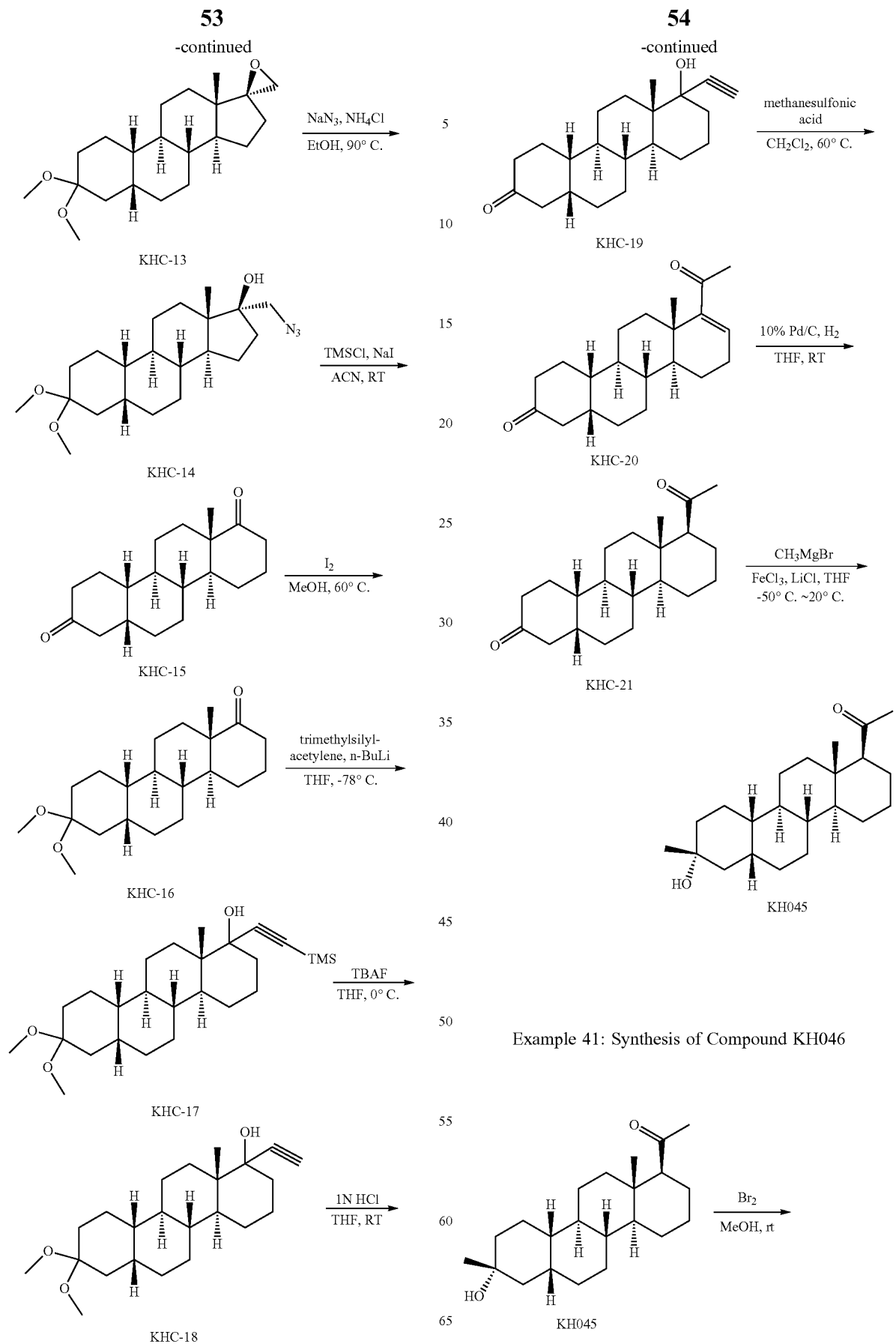
Example 41: Synthesis of Compound KH046

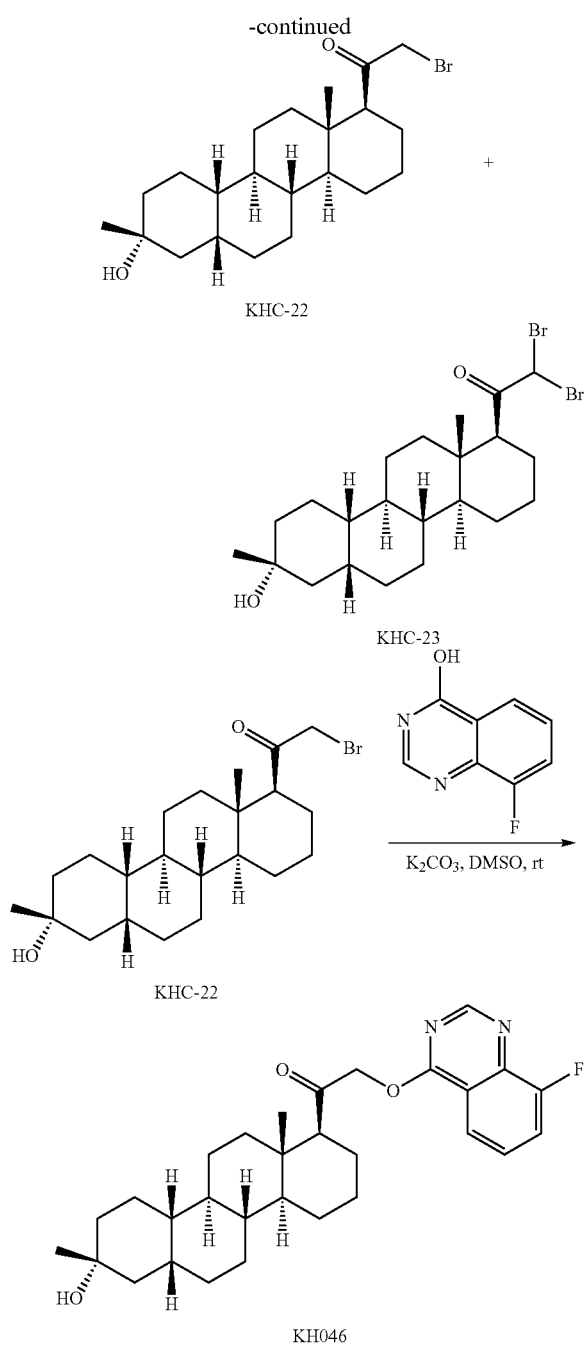

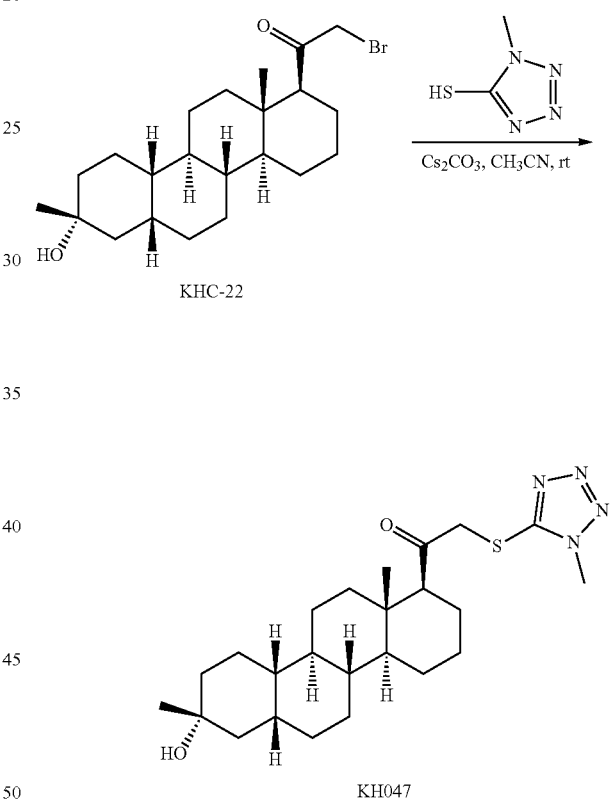

and 8-fluoro-4-hydroxyquinazoline (25 mg, 0.15 mmol) was added, Reaction was performed at room temperature overnight. TLC monitoring of the reaction showed that the reaction was complete., 10 ml of water was added to the reaction mixture, the mixture was extracted with EA (2×20 mL), the combined organic layers were washed with saturated NaCl, dried over anhydrous $Na_2SO_4$, and the solvent was distilled under reduced pressure to give crude product which was purified by TLC (eluent:PE/acetone=4:1) to give a white solid KH046 (33 mg, 55.56%).

$^1$H NMR (400 MHZ, CDCl$_3$) δ 8.06 (d, 1H), 7.88 (s, 1H), 7.55-7.40 (m, 2H), 4.80 (q, 2H), 2.44 (dd, 1H), 2.04-2.01 (m, 1H), 1.91-1.88 (m, 1H), 1.84-1.16 (m, 21H), 1.15-0.80 (m, 8H).

Example 42: Synthesis of Compound KH047

Compound KHC-22 and Compound KHC-23: Compound KH045 (1.50 g, 4.50 mmol) was dissolved in 40 mL CH$_3$OH, then Br$_2$ (1.08 g, 6.75 mmol). was added dropwise to the solution The reaction solution turned from orange to light yellow at RT for 4 hours, and TLC monitoring of the reaction showed that the reaction was complete. 30 ml of water was added to the reaction mixture, the mixture was extracted with EA (2×65 mL), the combined organic layers were washed with saturated NaCl, dried over anhydrous Na$_2$SO$_4$, and the solvent was distilled under reduced pressure to give crude product which was purified by flash chromatography on silica gel (eluent:CH$_2$Cl$_2$) to give white solid KHC-22 (1.19 g, 64.34%) and white solid KHC-23 (0.33 g, 17.84%).

Compound KH046: KHC-22 (50 mg, 0.12 mmol) was dissolved in 5 mL DMSO, then K$_2$CO$_3$ (21 mg, 0.15 mmol)

Compound KH047: KHC-22 (50 mg, 0.12 mmol) was dissolved in CH$_3$CN 5 mL, then Cs$_2$CO$_3$ (49 mg, 0.15 mmol) and 5-mercapto-1-methyl-1H-tetrazolium (17 mg, 0.15 mmol) was added, Reaction was performed at room temperature overnight. TLC monitoring of the reaction showed that the reaction was complete., 10 ml of water was added to the reaction mixture, the mixture was extracted with EA (2×20 mL), the combined organic layers were washed with saturated NaCl, dried over anhydrous Na$_2$SO$_4$, and the solvent was distilled under reduced pressure to give crude product which was purified by TLC (eluent:PE/acetone=4:1) to give a white solid KH047 (51 mg, 50.12%).

$^1$H NMR (400 MHZ, CDCl$_3$) 4.40 (dd, 2H), 3.97 (s, 3H), 2.48 (dd, 1H), 2.05-1.99 (m, 1H), 1.93-1.82 (m, 1H), 1.83-1.14 (m, 21H), 1.13-0.70 (m, 8H).

Example 43: Synthesis of Compound KH048

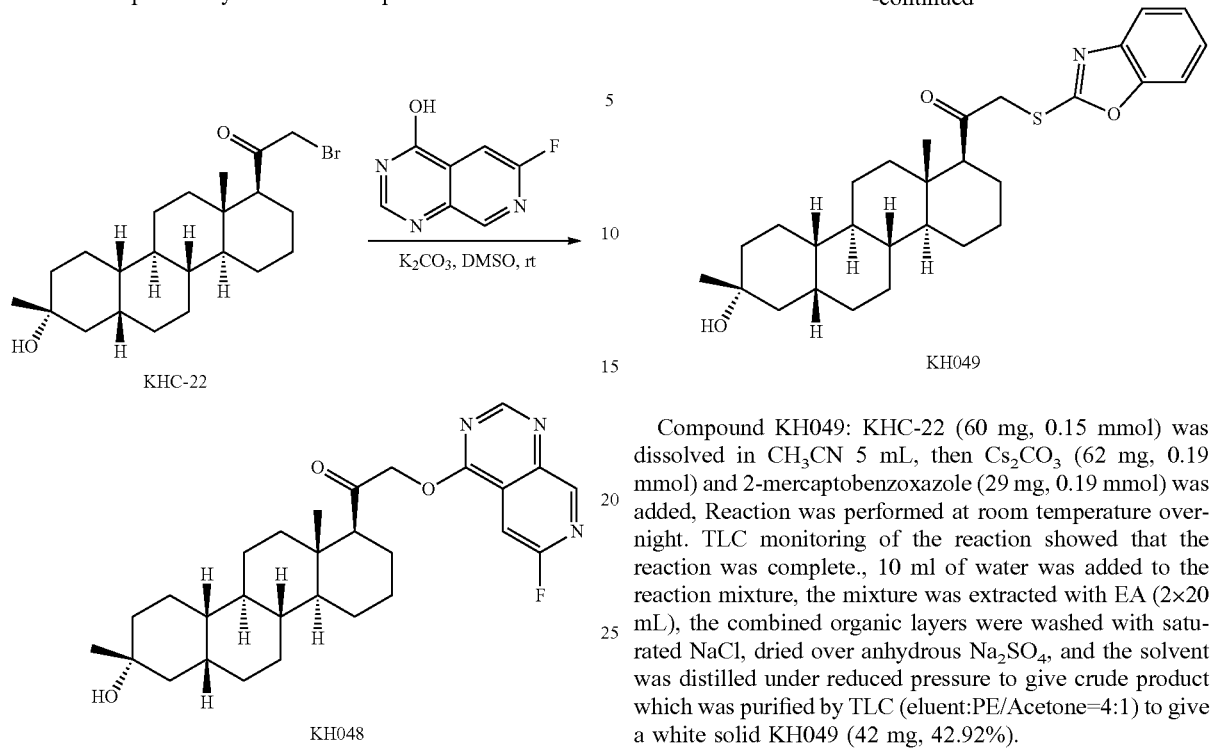

Compound KH048: KHC-22 (60 mg, 0.14 mmol) was dissolved in DMSO 5 mL, then K₂CO₃ (58 mg, 0.42 mmol) and 6-fluoropyridine [3,4-d] Pyrimidin-4-one (69 mg, 0.42 mmol) was added, Reaction was performed at room temperature overnight. TLC monitoring of the reaction showed that the reaction was complete., 10 ml of water was added to the reaction mixture, the mixture was extracted with EA (2×20 mL), the combined organic layers were washed with saturated NaCl, dried over anhydrous Na₂SO₄, and the solvent was distilled under reduced pressure to give crude product which was purified by TLC (eluent:PE/CH₃OH=40:1) to give a white solid KH048 (37 mg, 50.12%).

¹H NMR (400 MHZ, CDCl₃) δ 8.82 (s, 1H), 7.79 (s, 1H), 7.66 (d, 1H), 4.80 (dd, 2H), 2.44 (dd, 1H), 2.05-1.99 (m, 1H), 1.93-1.82 (m, 1H), 1.83-1.14 (m, 21H), 1.13-0.70 (m, 8H).

Example 44: Synthesis of Compound KH049

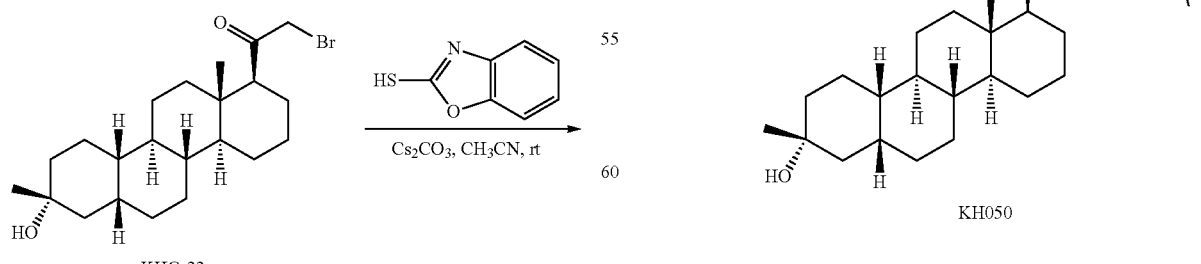

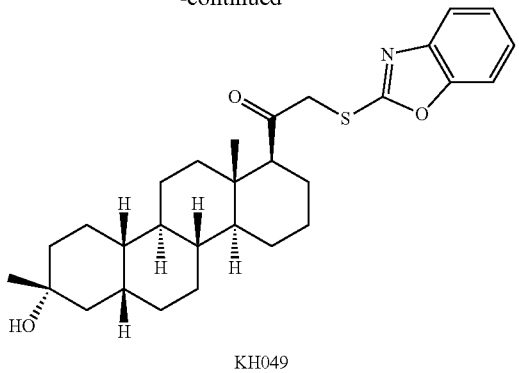

Compound KH049: KHC-22 (60 mg, 0.15 mmol) was dissolved in CH₃CN 5 mL, then Cs₂CO₃ (62 mg, 0.19 mmol) and 2-mercaptobenzoxazole (29 mg, 0.19 mmol) was added, Reaction was performed at room temperature overnight. TLC monitoring of the reaction showed that the reaction was complete., 10 ml of water was added to the reaction mixture, the mixture was extracted with EA (2×20 mL), the combined organic layers were washed with saturated NaCl, dried over anhydrous Na₂SO₄, and the solvent was distilled under reduced pressure to give crude product which was purified by TLC (eluent:PE/Acetone=4:1) to give a white solid KH049 (42 mg, 42.92%).

¹H NMR (400 MHZ, CDCl₃) δ 7.55 (d, 1H), 7.42 (d, 1H), 7.34-7.24 (m, 2H), 4.33 (dd, 2H), 2.57 (dd, 1H), 2.05-1.99 (m, 1H), 1.93-1.82 (m, 1H), 1.83-1.14 (m, 21H), 1.13-0.70 (m, 8H).

Example 45: Synthesis of Compound KH050

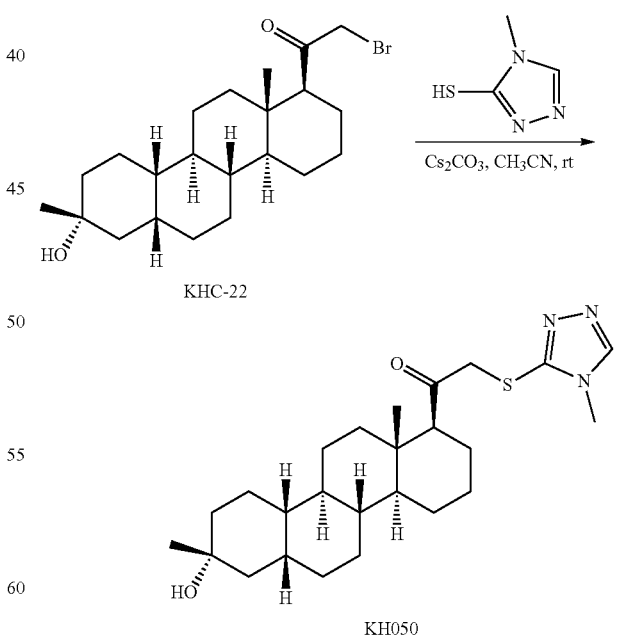

Compound KH050: KHC-22 (60 mg, 0.15 mmol) was dissolved in CH₃CN 5 mL, then Cs₂CO₃ (62 mg, 0.19 mmol) and 3-mercapto-4-methyl-4H-1, 2, 4-triazole (22 mg, 0.19 mmol) was added, Reaction was performed at room temperature overnight. TLC monitoring of the reaction showed that the reaction was complete., 10 ml of water was added to the reaction mixture, the mixture was extracted with EA (2×20 mL), the combined organic layers were washed with saturated NaCl, dried over anhydrous $Na_2SO_4$, and the solvent was distilled under reduced pressure to give crude product which was purified by TLC (eluent:$CH_2Cl_2$/$CH_3OH$=70:1) to give a white solid KH050 (17 mg, 25.41%).

$^1$H NMR (400 MHZ, $CDCl_3$) δ 8.22 (s, 1H), 4.37 (dd, 2H), 3.68 (s, 3H), 2.50 (dd, 1H), 2.10-1.97 (m, 1H), 2.06-2.02 (m, 1H), 1.79-1.14 (m, 21H), 1.12-0.79 (m, 8H).

Example 46: Synthesis of Compound KH051

Example 47: Synthesis of Compound KH052 and Compound KH053

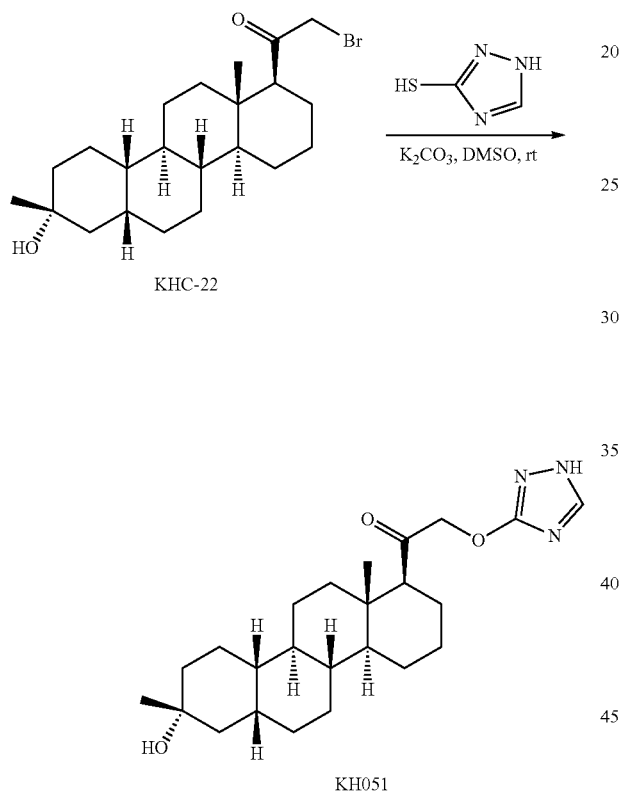

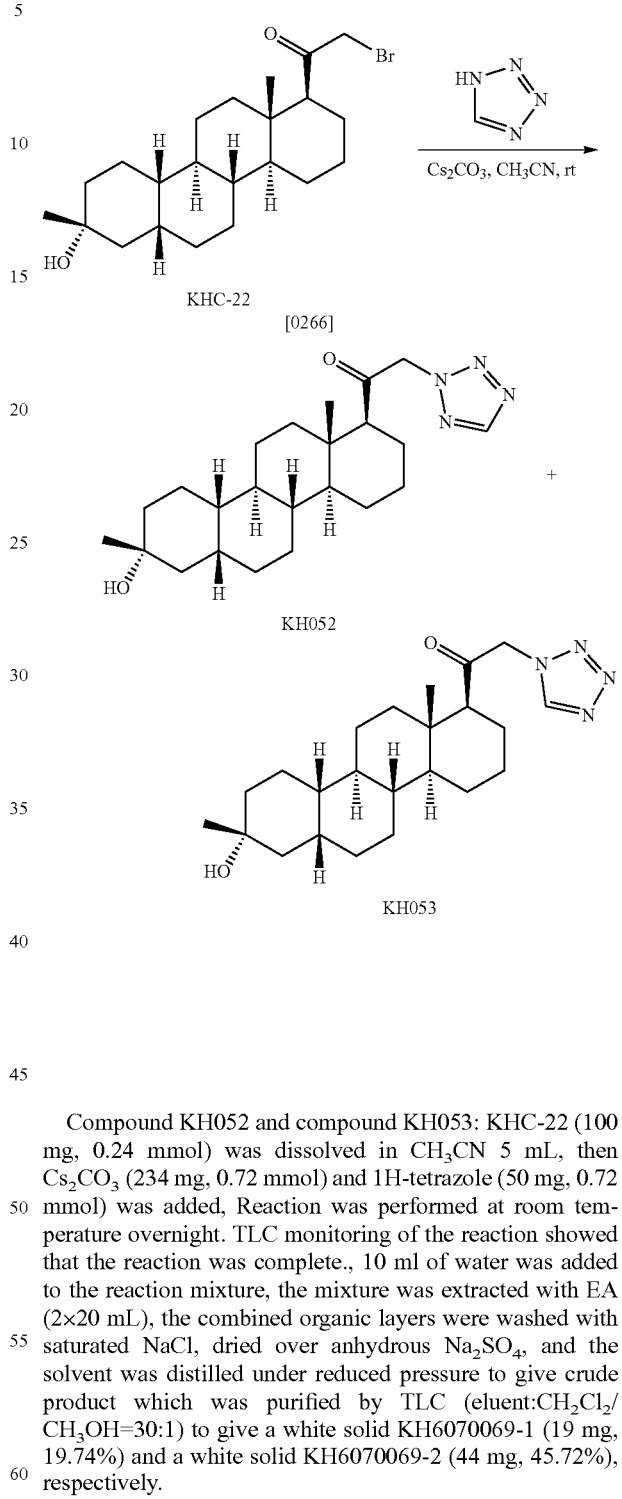

Compound KH051: KHC-22 (60 mg, 0.15 mmol) was dissolved in DMSO 5 mL, then $K_2CO_3$ (58 mg, 0.42 mmol) and 3-hydroxy-1H-1, 2, 4-triazole (36 mg, 0.42 mmol) was added, Reaction was performed at room temperature overnight. TLC monitoring of the reaction showed that the reaction was complete., 10 ml of water was added to the reaction mixture, the mixture was extracted with EA (2×20 mL), the combined organic layers were washed with saturated NaCl, dried over anhydrous $Na_2SO_4$, and the solvent was distilled under reduced pressure to give crude product which was purified by TLC (eluent:$CH_2Cl_2$/$CH_3OH$=40:1) to give a white solid KH051 (27 mg, 46.36%).

$^1$H NMR (400 MHZ, $CDCl_3$) δ 9.57 (s, 1H), 7.42 (s, 1H), 4.46 (q, 2H), 2.34 (dd, 1H), 2.07-1.96 (m, 1H), 1.88-1.82 (m, 1H), 1.79 (s, 21H), 1.11-0.81 (m, 8H).

Compound KH052 and compound KH053: KHC-22 (100 mg, 0.24 mmol) was dissolved in $CH_3CN$ 5 mL, then $Cs_2CO_3$ (234 mg, 0.72 mmol) and 1H-tetrazole (50 mg, 0.72 mmol) was added, Reaction was performed at room temperature overnight. TLC monitoring of the reaction showed that the reaction was complete., 10 ml of water was added to the reaction mixture, the mixture was extracted with EA (2×20 mL), the combined organic layers were washed with saturated NaCl, dried over anhydrous $Na_2SO_4$, and the solvent was distilled under reduced pressure to give crude product which was purified by TLC (eluent:$CH_2Cl_2$/$CH_3OH$=30:1) to give a white solid KH6070069-1 (19 mg, 19.74%) and a white solid KH6070069-2 (44 mg, 45.72%), respectively.

$^1$H NMR (400 MHZ, $CDCl_3$) δ 8.57 (s, 1H), 5.49 (s, 2H), 2.33 (dd, 1H), 2.05-2.01 (m, 1H), 1.94-1.84 (m, 1H), 1.83-1.15 (m, 21H), 1.14-0.82 (m, 8H).

$^1$H NMR (400 MHZ, $CDCl_3$) δ 8.72 (s, 1H), 5.29 (dd, 2H), 2.41 (dd, 1H), 2.06-2.01 (m, 1H), 1.95-1.85 (m, 1H), 1.85-1.15 (m, 21H), 1.14-0.82 (m, 8H).

Example 48: Synthesis of Compound KH054

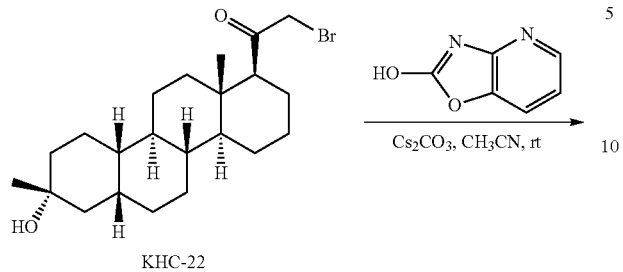

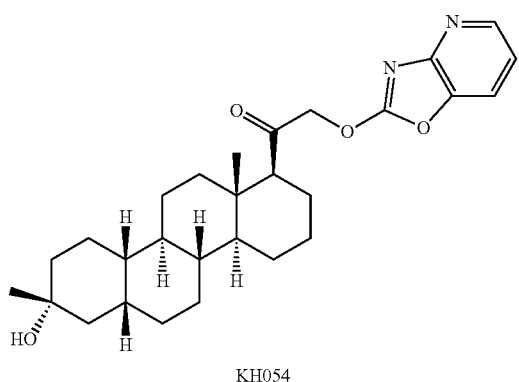

Compound KH054: KHC-22 (60 mg, 0.15 mmol) was dissolved in 5 mL CH₃CN, then Cs₂CO₃ (62 mg, 0.19 mmol) and 2-hydroxyoxazole [4,5-b]] Pyridine (26 mg, 0.19 mmol) was added, Reaction was performed at room temperature overnight. TLC monitoring of the reaction showed that the reaction was complete., 10 ml of water was added to the reaction mixture, the mixture was extracted with EA (2×20 mL), the combined organic layers were washed with saturated NaCl, dried over anhydrous Na₂SO₄, and the solvent was distilled under reduced pressure to give crude product which was purified by TLC (eluent:CH₂Cl₂/CH₃OH=70:1) to give a white solid KH054 (17 mg, 42.92%).

¹H NMR (400 MHZ, CDCl₃) δ 7.25 (d, 1H), 7.01 (d, 1H), 6.69 (t, 1H), 5.11 (q, 2H), 2.40 (dd, 1H), 2.08-1.98 (m, 1H), 1.93-1.83 (m, 1H), 1.82-1.14 (m, 21H), 1.15-0.81 (m, 8H).

Example 49: Synthesis of Compound KH055

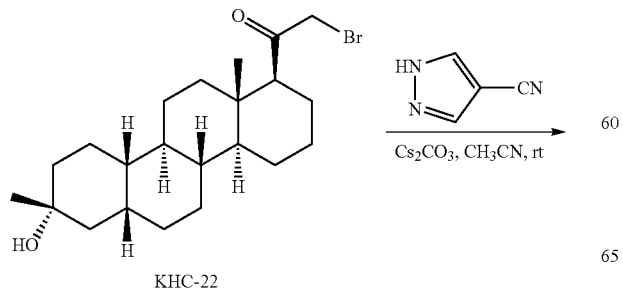

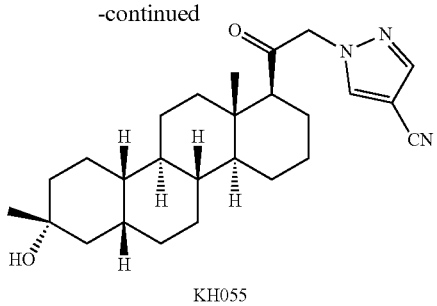

Compound KH055: KHC-22 (60 mg, 0.15 mmol) was dissolved in CH₃CN 5 mL, then Cs₂CO₃ (156 mg, 0.48 mmol) and 4-cyanopyrazole (45 mg, 0.48 mmol) was added, Reaction was performed at room temperature overnight. TLC monitoring of the reaction showed that the reaction was complete., 10 ml of water 10 ml water was added to the reaction mixture, the mixture was the mixture was extracted with EA (2×20 mL), the combined organic layers were washed with saturated NaCl, dried over anhydrous Na₂SO₄, and the solvent was distilled under reduced pressure to give crude product which was purified by TLC (eluent:CH₂Cl₂/CH₃OH=30:1) to give a white solid KH055 (51 mg, 50.12%).

¹H NMR (400 MHZ, CDCl₃) δ 7.83 (s, 1H), 7.81 (s, 1H), 4.99 (q, 2H), 2.32 (dd, 1H), 2.05-2.01 (m, 1H), 1.92-1.83 (m, 1H), 1.82-1.15 (m, 21H), 1.14-0.81 (m, 8H).

Example 50: Synthesis of Compound KH056

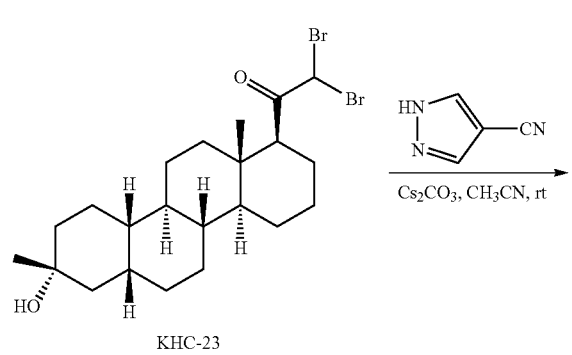

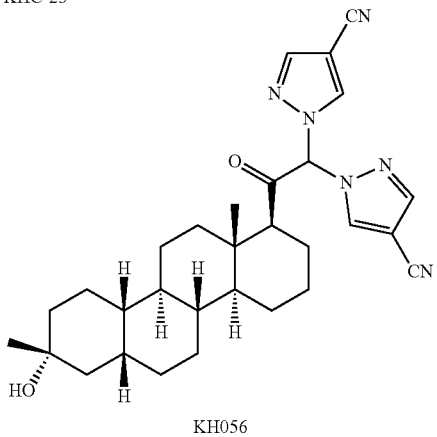

Compound KH056: KHC-23 (40 mg, 0.10 mmol) was dissolved in CH₃CN 5 mL, then Cs₂CO₃ (198 mg, 0.3 mmol) and 4-cyanopyrazole (28 mg, 0.30 mmol) was added, Reaction was performed at room temperature overnight. TLC monitoring of the reaction showed that the reaction was complete., 10 mL of water was added to the reaction mixture, the mixture was extracted with EA (2×20 mL), the combined organic layers were washed with saturated NaCl, dried over anhydrous Na₂SO₄, and the solvent was distilled under reduced pressure to give crude product which was purified by TLC (eluent:CH₂Cl₂/CH₃OH=30:1) to give a white solid KH056 (12 mg, 23.30%).

¹H NMR (400 MHZ, CDCl₃) δ 8.22 (s, 1H), 8.14 (s, 1H), 7.92 (s, 1H), 7.84 (s, 1H), 7.02 (s, 1H), 2.10 (dd, 1H), 2.05-2.00 (m, 1H), 1.87-1.78 (m, 1H), 1.78-1.14 (m, 21H), 1.12-0.79 (m, 8H).

Example 51: Synthesis of Compound KH057

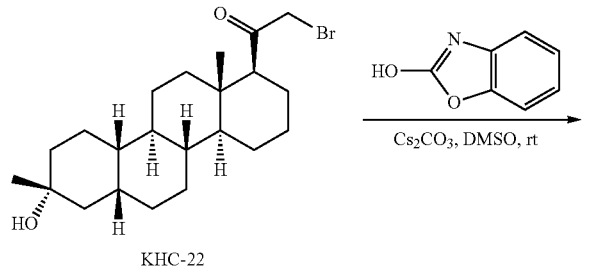

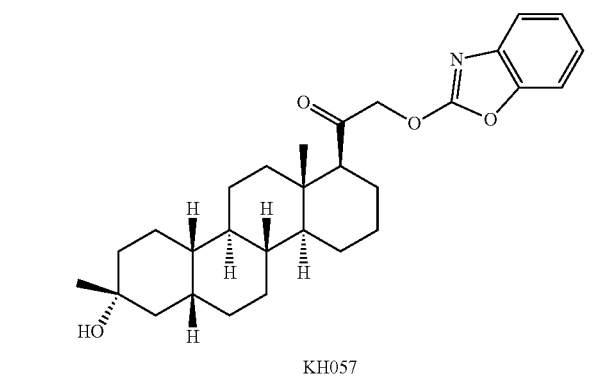

Compound KH057: KHC-22 (60 mg, 0.15 mmol) was dissolved in DMSO 5 mL, then Cs₂CO₃ (143 mg, 0.44 mmol) and 2-hydroxybenzoxazole (59 mg, 0.44 mmol) was added, Reaction was performed at room temperature overnight. TLC monitoring of the reaction showed that the reaction was complete., 10 ml of water was added to the reaction mixture, the mixture was extracted with EA (2×20 mL), the combined organic layers were washed with saturated NaCl, dried over anhydrous Na₂SO₄, and the solvent was distilled under reduced pressure to give crude product which was purified by TLC (eluent:PE/acetone=3:1) to give a white solid KH057 (30 mg, 42.92%).

¹H NMR (400 MHZ, CDCl₃) δ 7.24-7.19 (m, 1H), 7.17-7.07 (m, 2H), 6.75-6.65 (m, 1H), 4.58 (s, 2H), 2.40 (dd, 1H), 2.08-1.98 (m, 1H), 1.93-1.83 (m, 1H), 1.82-1.14 (m, 21H), 1.15-0.81 (m, 8H).

Example 52: Synthesis of Compound KH058

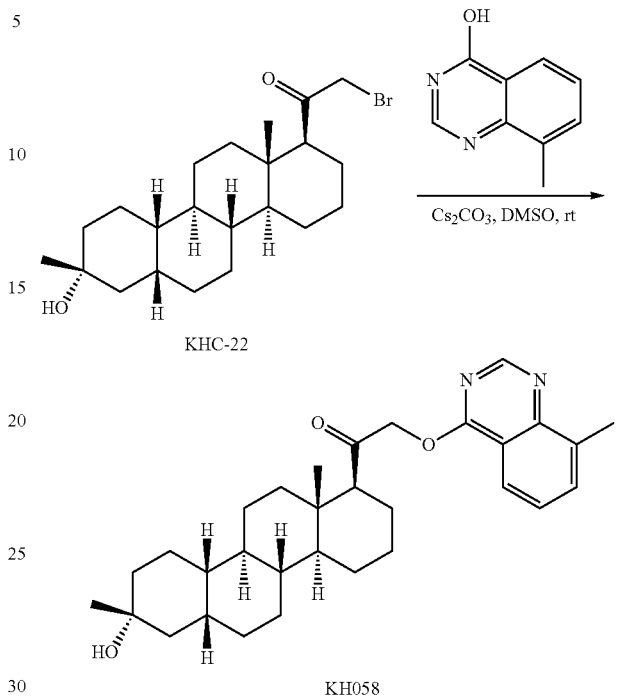

Compound KH058: KHC-22 (80 mg, 0.19 mmol) was dissolved in DMSO 5 mL, then Cs₂CO₃ (190 mg, 0.58 mmol) and 8-methyl-4-quinazolinone (93 mg, 0.58 mmol) was added, Reaction was performed at room temperature overnight. TLC monitoring of the reaction showed that the reaction was complete., 10 ml of water was added to the reaction mixture, the mixture was extracted with EA (2×20 mL), the combined organic layers were washed with saturated NaCl, dried over anhydrous Na₂SO₄, and the solvent was distilled under reduced pressure to give crude product which was purified by TLC (eluent:PE/acetone=3:1) to give a white solid KH058 (28 mg, 30.01%).

¹H NMR (400 MHZ, CDCl₃) δ 8.13 (d, 1H), 7.88 (s, 1H), 7.61 (d, 1H), 7.39 (t, 1H), 4.80 (dd, 2H), 3.49 (s, 3H), 2.45 (dd, 1H), 2.03-2.01 (m, 1H), 1.92-1.84 (m, 1H), 1.83-1.16 (m, 21H), 1.14-0.80 (m, 8H).

Example 53: Synthesis of Compound KH059

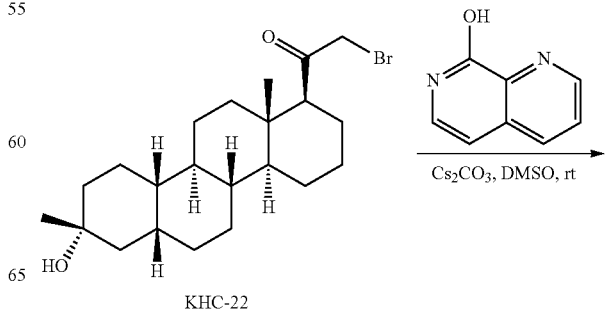

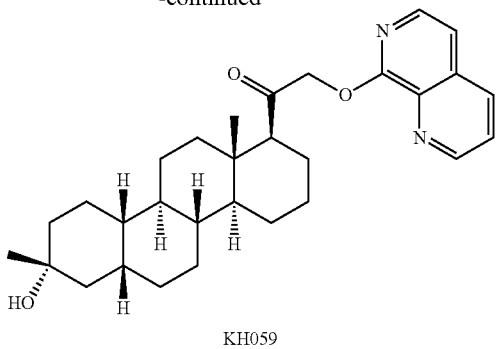

KH059

Compound KH059: KHC-22 (80 mg, 0.19 mmol) was dissolved in DMSO 5 mL, then $Cs_2CO_3$ (190 mg, 0.58 mmol) and 8-hydroxy-1, 7-naphthyridine (85 mg, 0.58 mmol) was added, Reaction was performed at room temperature overnight. TLC monitoring of the reaction showed that the reaction was complete., 10 ml of water was added to the reaction mixture, the mixture was extracted with EA (2×20 mL), the combined organic layers were washed with saturated NaCl, dried over anhydrous $Na_2SO_4$, and the solvent was distilled under reduced pressure to give crude product which was purified by TLC (eluent:PE/acetone=3:1) to give a white solid KH058 (28 mg, 30.89%).

$^1$H NMR (400 MHZ, $CDCl_3$) δ 8.86 (d, 1H), 7.88 (d, 1H), 7.54 (dd, 1H), 6.96 (d, 1H), 6.45 (d, 1H), 4.86 (s, 2H), 2.45 (dd, 1H), 2.09-1.95 (m, 1H), 1.87-1.83 (m, 1H), 1.80-1.15 (m, 21H), 1.12-0.76 (m, 8H).

Example 54: Synthesis of Compound KH060

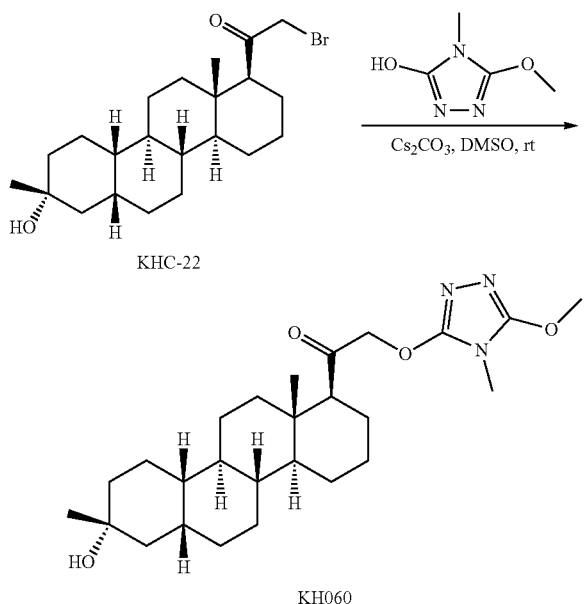

KHC-22

KH060

Compound KH060: KHC-22 (100 mg, 0.24 mmol) was dissolved in 5 mL DMSO, then $Cs_2CO_3$ (156 mg, 0.48 mmol) and 3-hydroxy-4-methyl-5-methoxy-4H-1, 2, 4-triazole (62 mg, 0.48 mmol) was added, Reaction was performed at room temperature overnight. TLC monitoring of the reaction showed that the reaction was complete., 10 ml of water was added to the reaction mixture, the mixture was extracted with EA (2×20 mL), the combined organic layers were washed with saturated NaCl, dried over anhydrous $Na_2SO_4$, and the solvent was distilled under reduced pressure to give crude product which was purified by TLC (eluent:PE/acetone=4:1) to give a white solid KH058 (56 mg, 50.72%).

$^1$H NMR (400 MHZ, $CDCl_3$) § 4.54-4.40 (m, 2H), 3.93 (s, 3H), 3.12 (s, 3H), 2.29 (dd, 1H), 2.03-1.99 (m, 1H), 1.85-1.82 (m, 1H), 1.77-1.13 (m, 21H), 1.10-0.81 (m, 8H).

Example 55: Synthesis of Compound KH061

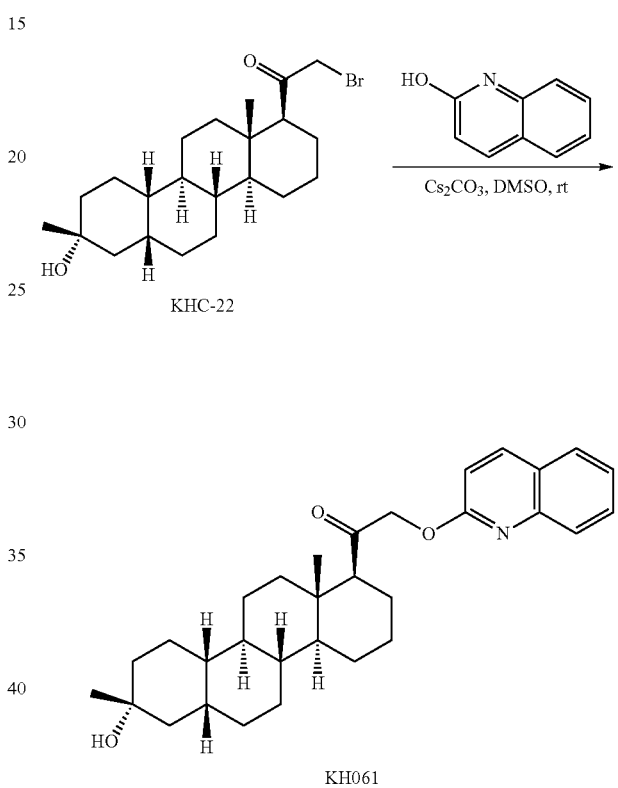

KHC-22

KH061

Compound KH061: KHC-22 (80 mg, 0.19 mmol) was dissolved in 5 mL DMSO, then $Cs_2CO_3$ (156 mg, 0.48 mmol) and 2-hydroxyquinoline (84 mg, 0.58 mmol) was added, Reaction was performed at room temperature overnight. TLC monitoring of the reaction showed that the reaction was complete., 10 ml of water was added to the reaction mixture, the mixture was extracted with EA (2×20 mL), the combined organic layers were washed with saturated NaCl, dried over anhydrous $Na_2SO_4$, and the solvent was distilled under reduced pressure to give crude product which was purified by TLC (eluent:PE/acetone=4:1) to give a white solid KH058 (45 mg, 49.76%).

$^1$H NMR (400 MHZ, $CDCl_3$) δ 8.05 (d, 1H), 7.75 (dd, 2H), 7.61 (t, 1H), 7.39 (t, 1H), 7.05 (d, 1H), 5.15 (s, 2H), 2.43 (dd, 1H), 2.04-2.00 (m, 1H), 1.86-1.83 (m, 1H), 1.78-1.12 (m, 21H), 1.10-0.80 (m, 8H).

Example 56: In Vitro Cell Viability Assay

The control compound used in the present invention has the chemical structure described below:

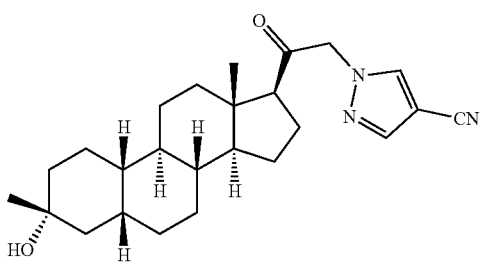

The specific synthesis of the control compound is prepared with reference to CN105339381B.

The present invention applies the two subunits of the recombinant $GABA_A$ receptor: $\alpha_1\beta_2\gamma_2$ and $\alpha_4\beta_3\delta$ to evaluate the potency of the exemplary compounds in vitro by patch-clamp electrophysiology.

56.1 Electrophysiological Testing Solution
Extracellular and Intracellular Fluid Compositions:

Extracellular fluid: 140 mM NaCl, 5 mM CsCl, 2 mM $CaCl_2\cdot 2H_2O$, 1 mM $MgCl_2\cdot 6H_2O$, 5 mM HEPES, 10 mM D-Glucose, pH=7.4 (NaOH).

Intracellular fluid: 130 mM CsCl, 0.1 mM $CaCl2\cdot H_2O$, 2 mM $MgCl_2\cdot 6H_2O$, 1.1 mM EGTA, 5 mM $Na_2$-ATP, 10 mM HEPES, pH=7.2 (CsOH).

The prepared intracellular fluid was divided into 1 mL per tube and froze and stored at −20° C. refrigerator, freshly melted intracellular fluid was used in the experiment every day. All the intracellular fluid was used up within three months.

56.2 Cell Lines with Stable Expression of Ion Channels:

| Ion Channel | Expressed Gene | Gene Info | Cell Line |
|---|---|---|---|
| $GABA_{A1}$ ($\alpha_1\beta_2\gamma_2$) | GABRA1 GABRB2 GABRG2 | NM_000806 NM_021911 NM_198904 | HEK293 |
| $GABA_{A4}$ ($\alpha_4\beta_3\delta$) | GABRA4 GABRB3 GABRD | NM_000809 NM_000814 NM_000815 | HEK293 |

56.3 Cell Culture
56.3.1 $GABA_A$ ($\alpha_1\beta_2\gamma_2$) cell culture

The HEK293 cells line stably expressing $GABA_A$ ($\alpha_1\beta_2\gamma_2$) receptors was cultured in Dulbecco's Modified Eagle Medium (DMEM) supplemented with 10% fetal bovine serum, 800 μg/mL G418, 200 μg/mL Hygromycin B and 100 μg/mL Zeocin. Cells were grown in a humidified incubator at 37° C. with 5% carbon dioxide.

Cell passage: The old medium was removed, and the cells were washed once with PBS. Then 1 mL 0.25%-Trypsin-EDTA solution was added and incubate at 37° C. for 0.5 min. When the cells are detached from the bottom of the dish, 5 ml of 37° C. pre-warmed complete medium was added. Cell aggregates were dissociated by gentle pipetting. The cell suspension was transferred into a sterile centrifuge tube and then the cell suspension was spun at 1000 rpm for 5 min to collect the cells. The cells were amplified or maintained by seeding $2.5\times10^5$ cells in a 6 cm cell culture dish (final medium volume: 5 mL).

To maintain electrophysiological performances, cell density must not exceed 80%.

Before manual patch clamp test, the cells were detached using 0.25%-Trypsin-EDTA solution. Then $8\times10^3$ cells were plated onto coverslips, and cultured in a 24-well plate (final medium volume: 500 μL) and tested after 18 hours by patch clamp.

56.3.2 $GABA_A$ ($\alpha_4\beta_3\delta$) Cell Culture

HEK293 cell line was cultured in DMEM containing 10% fetal bovine serum and 5% carbon dioxide at 37° C.

Cell passage: The old medium was removed, and the cells were washed once with PBS. Then 1 mL 0.25%-Trypsin-EDTA solution was added to digest cells. The culture dish was incubated at 37° C. in pre-warmed incubator for 0.5 minutes. As soon as cells were detached, about 5 mL 37° C. pre-warmed complete medium was added. Cell aggregates were dissociated by gentle pipetting. The cell suspension was transferred into a sterile centrifuge tube and then the cell suspension was be spun at approximately 1000 rpm for 5 minutes. The cells were amplified or maintained by seeding $2.5\times105$ cells in a 6 cm dish (final medium volume: 5 mL). For transfection, $8\times10^3$ cells were plated onto coverslips, and cultured in a 24-well plate (final medium volume: 5 mL).

Transfection: Second day, the transfection of $GABA_{A4}$ (α4, β3, δ plasmid ratio 1:1:1) was performed. The X-tremeGENE HP DAN Transfection Reagents kit were used. The ratio of the plasmid and transfection reagent was 1 μg: 2 μL. The amount of plasmid in the 24-well plate was 0.5 μg per well, and the transfection reagent was 1 μL. The following specific steps were taken for preparing the 12 wells: The 600 μL Opti-MEM was added to a sterile centrifuge tube along with 6 μg of plasmid and was allowed to mix well; Then, the 12 μL of transfection reagent was added, mixed well following 15 min incubation at room temperature. The transfection complex was then inoculated into the cell, 50 μL per well, and the transfection complex was lightly stirred and mixed.

This mixture was changed on the third day, and the patch-clamp was performed on the fourth day.

56.4 Patch-Clamp Testing

Glass pipette (BF 150-86-10, Sutter Instruments) was pulled using a micropipette puller (P97, Sutter Instruments). The glass pipette was manipulated using a micro-manipulator (MP285, Sutter Instruments) under the microscope (IX71, Olympus). After touching the cell, a slight suction was applied to achieve high seal resistance (GΩ). Fast capacitance (in pF) compensation was made after achieving high seal, and the membrane was broken. Cell capacitance (in pF) compensation was made from whole-cell capacitance compensation after the whole cell mode was achieved. No leak subtraction was made.

The test and control solutions flowed into a recording chamber mounted on the stage of an inverted microscope via a gravity-fed solution delivery system. During the experiment, solutions were withdrawn from the recording chamber by vacuum aspiration. Each concentration was tested at multiple times. All tests were performed at room temperature.

Whole cell model recorded $GABA_{A1}$ receptors current experimental protocol was indicated as follows: When sealing, cell was at a holding potential of −70 mV, with gap-free mode to record the peak current. The cell would be applied with 3 μM GABA to active current. After the test articles application for 30 s, each concentration of test articles was applied with 3 μM GABA followed by 2 minutes washout using extracellular solution. Finally, 100 μM GABA was used as a positive control. The data were collected by EPC-10 amplifier and stored in PatchMaster (HEKA) software.

Whole cell model recorded GABA$_{A4}$ receptors current experimental protocol was indicated as follows: When sealing, cell was at a holding potential of −70 mV, with gap-free mode to record the peak current. The cell would be applied with 10 nM GABA to active current. After the test articles application for 30 s, each concentration of test articles was applied with 10 nM GABA followed by 2 minutes washout using extracellular solution. Finally, 10 μM GABA was used as a positive control. The data were collected by EPC-10 amplifier and stored in PatchMaster (HEKA) software.

56.5 Data Quality Standard

The following criteria are used to determine whether the data is acceptable:
(1) Electrode resistance <5MΩ
(2) Seal resistance >1GΩ
(3) The start of access resistance <15 MΩ
(4) The end of access resistance <15 MΩ
(5) No obvious spontaneous current decay.
(6) No obvious current leakage when the membrane potential is-70 mv.

56.6 Data Analysis

In the detection of GABA$_{A1}$, the currents of 3 μM GABA and different concentrations of test compounds were respectively normalized to the current of 100 μM GABA $$\frac{\text{Peak current compound}}{\text{Peak current vehicle}},$$

and then the activation rate corresponding to each concentration was calculated.

In the detection of GABA$_{A4}$, the currents of 10 nM GABA and different concentrations of test compounds were respectively normalized to the current of 10 μM GABA $$\frac{\text{Peak current compound}}{\text{Peak current vehicle}},$$

and then the activation rate corresponding to each concentration was calculated. Means, Standard Deviation and Standard Error were calculated for each test group. EC$_{50}$ value was calculated using nonlinear regression:

$$Y=\text{Bottom}+(\text{Top}-\text{Bottom})/(1+10^{((\text{Log } EC_{50}-X)\times \text{HillSlope})})$$

To fit data to the concentration-response, EC$_{50}$ was the concentration giving a half-maximum effect and Hillslope was the Hill coefficient. Curve-fitting and EC$_{50}$ calculations were performed using Graphpad5.0 software.

56.7 Results of Experiments In Vitro

TABLE 1

Electrophysiological evaluation of the agonistic effect of the exemplary compounds on the GABA$_{A1}$ receptor

| Compounds | 0.1 μM | 1 μM |
|---|---|---|
| KH001 | D | B |
| KH002 | E | B |
| KH003 | D | B |
| KH004 | D | A |
| KH005 | D | B |
| KH006 | D | C |
| KH007 | E | C |
| KH008 | D | A |
| KH009 | D | A |
| KH010 | E | D |

TABLE 1-continued

Electrophysiological evaluation of the agonistic effect of the exemplary compounds on the GABA$_{A1}$ receptor

| Compounds | 0.1 μM | 1 μM |
|---|---|---|
| KH011 | D | B |
| KH012 | E | B |
| KH013 | E | E |
| KH014 | E | C |
| KH015 | E | E |
| KH016 | E | C |
| KH017 | E | E |
| KH018 | E | D |
| KH019 | E | E |
| KH020 | E | E |
| KH021 | E | E |
| KH022 | E | C |
| KH023 | E | E |
| KH024 | E | C |
| KH025 | E | B |
| KH026 | E | C |
| KH027 | E | E |
| KH028 | E | E |
| KH029 | E | E |
| KH030 | E | E |
| KH031 | E | C |
| KH032 | E | D |
| KH033 | E | D |
| KH034 | E | E |
| KH035 | E | D |
| KH036 | E | E |
| KH037 | E | E |
| KH038 | E | C |
| KH039 | E | B |
| KH040 | E | D |
| KH041 | E | B |
| KH042 | E | C |
| KH043 | E | D |
| KH045 | E | D |
| KH047 | E | E |
| KH048 | E | E |
| KH051 | E | E |
| KH052 | E | E |
| The control | E | D |

A: >80%, B: 60%-80% (including 60%), C: 40%-60% (including 40%), D: 20%-40% (including 20%), E: 0-20%.

Table 1 showed the potency of the exemplary compounds at concentrations 0.1 μM and 1 μM. The potency was based on the ratio of the peak current generated on the GABA$_{A1}$ receptor to the peak current generated only in 100 μmol of GABA and the ratio was multiplied by 100%. The peak current generated on the GABA$_{A1}$ receptor was that the exemplary compounds act on the GABA$_{A1}$ receptor together with 3 μmol GABA at these two concentrations respectively.

TABLE 2

Electrophysiological evaluation of the exemplary compounds at the GABA$_{A1}$ receptor

| The exemplary compounds | EC$_{50}$ (nmol) | E$_{max}$ |
|---|---|---|
| KH002 | 463.9 | 74.6% |
| KH003 | 478.1 | 72.8% |
| KH004 | 403.7 | 106.1% |
| KH022 | 821.1 | 93.1% |
| KH025 | 619.9 | 93.7% |
| The control | 1261 | 84.2% |

E$_{max}$ is defined as the ratio of the peak current generated on the GABA$_{A1}$ receptor to the peak current generated only in 100 μmol of GABA and the ratio is multiplied by 100%. The peak current generated on the GABA$_{A1}$ receptor is that the exemplary compounds act on the GABA$_{A1}$ receptor together with 3 μmol GABA.

TABLE 3

Electrophysiological evaluation of the exemplary compounds on the $GABA_{A1}$ receptor

| The exemplary compounds | $EC_{50}$(nmol) (without GABA) | $E_{max}$ (without GABA) | $EC_{50}$(nmol) (with 10 nM GABA) | $E_{max}$ (with 10 nM GABA) |
|---|---|---|---|---|
| KH001 | 172.8 | 103.2% | 132.2 | 91.7% |
| KH004 | 171.6 | 158.4% | 134.6 | 171.6% |
| KH022 | N/A | 45.8% | 385.5 | 88.6% |
| KH025 | 947.1 | 84.6% | 571.9 | 92.5% |
| KH039 | >4000 | 120.8% | >4000 | 124.6% |
| The control | N/A | 113.9% | 218.7 | 148.7% |

N/A indicates that the current does not change with concentration.

$E_{max}$ is defined as the ratio of the peak current generated on the $GABA_{A1}$ receptor to the peak current generated only in GABA and the ratio is multiplied by 100%. The peak current generated on the $GABA_{A1}$ receptor is that the exemplary compounds act alone on the $GABA_{A1}$ receptor or together with 10 nmol GABA respectively.

Example 57: Pharmacokinetics in Brain and Plasma after Dosing

1. Protocol
1.1 Tested Drugs
KH022 in the present invention and the control described in example 56
1.2 Animals
The experimental animals are CD-1 mice.
1.3 Administration
Preparation of test compounds with 30% SBECD in water for intragastric administration. On the first day of the experiment, the animals in the first group are intraperitoneally injected with the solution of KH022 or the control with the dosage of 5 mL/kg; before the administration, the animals were weighed, and the administration volume was calculated according to the body weight. Whole blood samples (about 0.03 ml per group) were collected at a specified time by saphenous vein puncture (or other suitable collection locations). Blood samples were immediately processed for plasma by centrifugation at approximately 4° C., 3,200 g for 10 min, quickly placed in dry ice, and kept below –20° C. until LC/MS/MS analysis. At each time point, animals were euthanized using CO2 and then brain tissue was collected, rinsed and dried with physiological saline, and homogenized with 4 times the brain weight (g) volume of 15 mM PBS (pH7.4):MeOH=2:1. After homogenization, samples were transferred to labeled centrifuge tubes and quickly placed in dry ice, stored at or below –20° C. for LC-MS/MS analysis.
2. Data Analysis
The concentrations of the test compound in dose formulation samples was determined by the LC/UV, and the calibration curve contains at least 6 calibration standards, $R^2 \geq 0.999$. The concentrations of the test compound in biological matrix was determined by the LC/MS/MS method. The retention time of test compounds or internal standards, chromatogram acquisition and chromatogram integration were processed by software Analyst (Applied Biosystems), and data statistics were processed by software Watson LIMS (Thermo Fisher Scientific) or Analyst (Applied Biosystems). The unit of the analyte concentration in the sample is ng/ml, with 3 significant digits reserved, and all values expressed in percentages (such as % deviation and % coefficient of variation, etc.) were kept to one decimal place. Non-compartmental models of WinNonlin™ Version 6.3 (Pharsight, Mountain View, CA) pharmacokinetic software were used to process plasma concentrations, and linear log trapezoidal method was used to calculate pharmacokinetic parameters.

Figure 2:
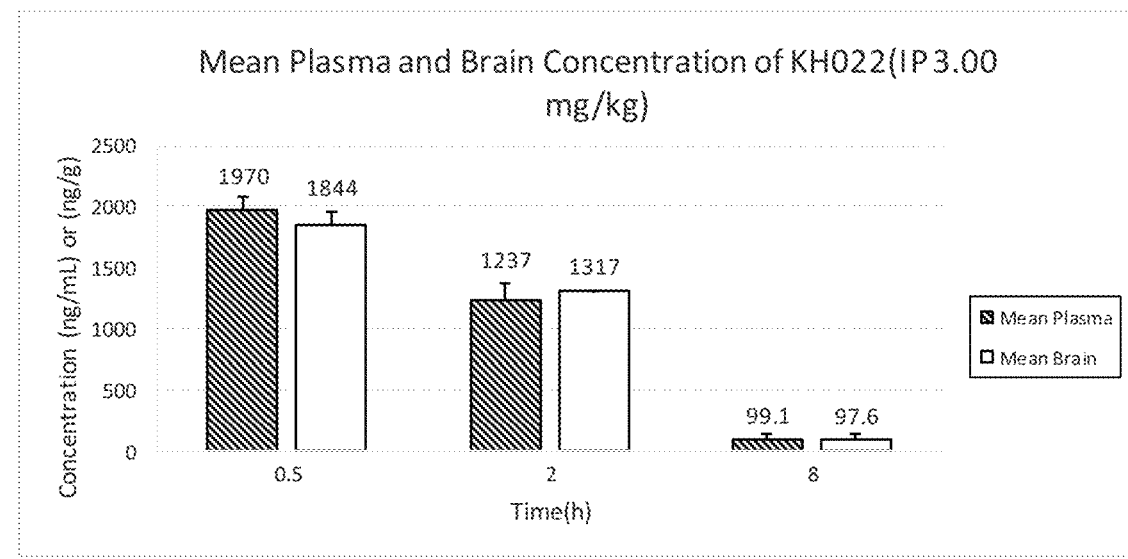
FIG. 2 is a graph showing changes of KH022 in plasma and brain over time.

3. Experimental Results
As shown in FIG. 1 and FIG. 2, KH022 is cleared more slowly in the mouse brain than the control (there is no detection of the control in the brain at 8h) at the same dosage, and the content of KH022 in the mouse brain is 2.5 times of the control at 2h.

57.3 Anti-Anxiety Test in Mice
57.3.1 light-dark shuttle box: The light-dark shuttle box is a standard and well characterized assay for anxiolytic effects of the exemplary compounds. Mice naturally avoid the light of the box because light makes mice evasive and stressful, but the exploration habit of mice also prompts mice to try to explore a bright box. Increased time on the light of the box by the exemplary compounds reflects an anxiolytic effect on mice. The experimental mice were randomly divided into 5 groups based on weight, including a negative control group, two different dosage groups (1 mg/kg and 3 mg/kg) of the tested compounds (KH004 or KH022), and every group had 10 male mice. Mice were administered with corresponding dosage for tested intervention for 5 consecutive days in advance, and conducting anxiolytic experiments after 30 min of the last administration. The retention time in the light box was selected as the main index for evaluating the anti-anxiety effect of KH004 and KH022. Experimental results are shown in Table 4.

TABLE 4

Effect of KH004 and KH022 on the retention time in the light box

| Groups | dosage (mg/kg) | Number of mice | The retention time (%) |
|---|---|---|---|
| the negative control group | 0 | 10 | 26.69 ± 8.38 |
| KH022 | 1.0 | 10 | 50.00 ± 4.59**** |
|  | 3.0 | 10 | 56.66 ± 7.96**** |
| KH004 | 1.0 | 10 | 50.30 ± 6.89**** |
|  | 3.0 | 10 | 53.91 ± 9.37**** |

Note:
data in the table are all expressed as mean ± standard deviation (Mean ± SD). Statistical analysis is performed on 10 animals in each experimental group and *P < 0.05, P < 0.01, *P < 0.001, ****P < 0.0001 represents different experimental groups and the negative control group animals.

57.3.2 Elevated Plus Maze (EPM) testing: EPM for exploratory behavior was used to assess general motor and anxiety-like behavior that was consisting of two open arms and two closed arms extending from a common central platform, thus forming anxiety-like symptoms. The anxiolytic compound would relieve the anxiety conflict status of animals in the test system. The experimental mice were randomly divided into 4 groups based on weight, including a negative control group, two different dosage groups (1 mg/kg and 3 mg/kg) of test compounds (KH004 or KH022), and every group had 10 male mice. Mice were administered with corresponding dosage for test intervention for 5 consecutive days in advance, and conducting anxiolytic experiments after 30 min of the last administration. The percentage of the retention time (latency) of mice open arms were used as the main index to evaluate the anxiolytic effect of KH004 and KH022, the results are shown in Table 5.

TABLE 5

Effect of different dosage of KH004 and
KH022 on the retention time of mice open arms

| Groups | dosage (mg/kg) | Number of mice | The retention time (%) |
|---|---|---|---|
| the negative control group | 0 | 10 | 10.79 ± 6.24 |
| KH022 | 1 | 10 | 31.40 ± 16.41** |
|  | 3 | 10 | 39.46 ± 11.82**** |
| KH004 | 1 | 10 | 27.21 ± 11.15*** |
|  | 3 | 10 | 36.44 ± 13.28**** |

Note:
data in the table are all expressed as mean ± standard deviation (Mean ± SD). Statistical analysis is performed on 10 animals in each experimental group and *P < 0.05, P < 0.01, *P < 0.001, ****P < 0.0001 represents different experimental groups and negative control group animals.
Conclusion: KH004 and KH022 significantly increase the percent open arm retention time of the animals, showing anxiolytic effect.

Since the drugs which are acting on GABA (A) receptor can produce behavioral anesthesia (side effects), side effects of mice during administration were observed during the course of the elevated plus maze experiment. Each group of 10 mice was observed for three behavioral manifestations: gait, mobility and prone behavior. "+" indicates severity, three "+" are the most severe, with time to resume normal action >60 minutes. The positive drug is the control compound as described in example 56 and the results are shown in table 6. KH004 and KH022 have less side effects compared to the positive drug in Table 6.

TABLE 6 summary of observation of side effects in animals during administration

| | The first day | | | | | | The second day | | | | | |
|---|---|---|---|---|---|---|---|---|---|---|---|---|
| The dosage | Gait | | mobility | | prone behavior | | Gait | | mobility | | prone behavior | |
| of 3mg/kg | Number | Level | Number | Level | Number | Level | Number | Level | Number | Level | Number | Level |
| The positive drug | 7 | ++ | 3 | +++ | 2 | + | 6 | ++ | 0 | | 0 | |
| KH004 | 0 | | 0 | | 0 | | 0 | | 0 | | 0 | |
| KH022 | 3 | + | 1 | ++ | 0 | | 2 | + | 0 | | 0 | |

| | The third day | | | | | | The forth day | | | | | |
|---|---|---|---|---|---|---|---|---|---|---|---|---|
| The dosage | Gait | | mobility | | prone behavior | | Gait | | mobility | | prone behavior | |
| of 3mg/kg | Number | Level | Number | Level | Number | Level | Number | Level | Number | Level | Number | Level |
| The positive drug | 8 | + | 4 | ++ | 0 | | 9 | + | 5 | + | 0 | |
| KH004 | 1 | + | 0 | | 0 | | 0 | | 0 | | 0 | |
| KH022 | 1 | + | 0 | | 0 | | 3 | + | 1 | + | 0 | |

The invention claimed is:

1. A compound of Formula (I):

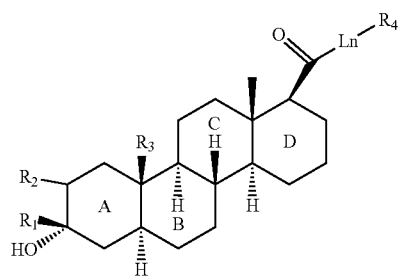

(I)

or a pharmaceutically acceptable salt thereof, wherein:

R1 is hydrogen, substituted or unsubstituted C1-6 alkyl, substituted or unsubstituted C1-6 alkoxy, substituted or unsubstituted C2-6 alkenyl, substituted or unsubstituted C2-6 alkynyl, or substituted or unsubstituted C3-6 carbocyclyl;

R2 is hydrogen, halogen, substituted or unsubstituted C1-6 alkyl, substituted or unsubstituted C1-6 alkoxy, substituted or unsubstituted C2-6 alkenyl, substituted or unsubstituted C2-6 alkynyl, substituted or unsubstituted C3-6 carbocyclyl;

R3 is unsubstituted C1-6 alkyl;

L is —C(Rb)(Rb)-, each Rb is independently hydrogen or C1-C6 alkyl, n is an integer of 0 to 3;

R4 is halogen, heteroaryloxy, heteroarylthio, or substituted or unsubstituted heteroaryl or heterocyclyl.

2. The compound of claim 1 or a pharmaceutically acceptable salt thereof, wherein $R^1$ is hydrogen, substituted or unsubstituted C1-6 alkyl; R2 is hydrogen, substituted or unsubstituted C1-6 alkyl; R3 is an unsubstituted C1-6 alkyl; Rb is hydrogen, n is an integer of 1 to 2; R4 is heteroaryl optionally substituted with cyano, nitro, hydroxy, halo, C1-C6 alkyl, C1-C6 alkoxy, C1-C6 haloalkyl, —C(O)Rd, —C(O)N(Re)(Rf), —C(O)O(Rd), —N(Re)(Rf), —OC(O)N(Re)(Rf), —OC(O)O(Rd), —OC(O)Rd, —S(O)$_{0-2}$Rd, —S(O)$_{0-2}$ORd or —S(O)$_{0-2}$N(Re)(Rf); each Rd is independently hydrogen or C1-C6 alkyl; each Re and Rf is independently hydrogen, C1-C6 alkyl, carbocyclyl, heterocyclyl, aryl, or heteroaryl.

3. The compound of claim 2 or a pharmaceutically acceptable salt thereof, wherein R4 is a five- or six-membered heteroaryl containing 2-4 nitrogen atoms and is optionally substituted with cyano, nitro, hydroxyl, halo, C1-C6 alkyl, C1-C6 alkoxy, or C1-C6 haloalkyl.

4. A compound or a pharmaceutically acceptable salt thereof, wherein the compound is a compound as shown in formula II:

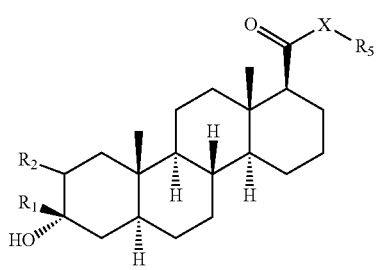

(II)

wherein:
R1 is hydrogen or C1-3 alkyl substituted or unsubstituted with halogen; R2 is hydrogen, halogen, C1-6 alkyl unsubstituted or substituted with halogen or C1-6 alkoxy unsubstituted or substituted with halogen; X is CH$_2$, N, O or S; R5 is selected from the group consisting of:

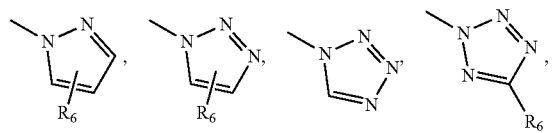

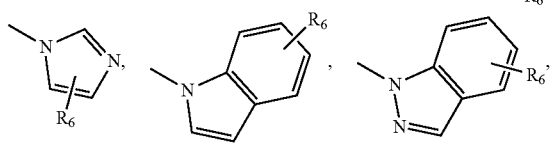

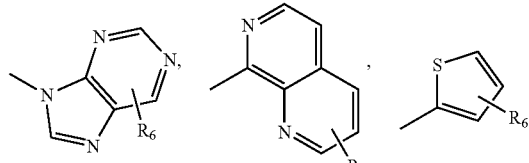

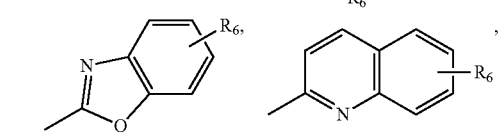

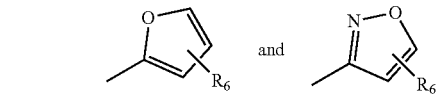

wherein R$^6$ is H, halogen, CN, CF3, NO2, C1-6 alkyl unsubstituted or substituted with halogen or C1-6 alkoxy unsubstituted or substituted with halogen.

5. The compound of claim 1 or a pharmaceutically acceptable salt thereof, wherein the compound is selected from the group consisting of:

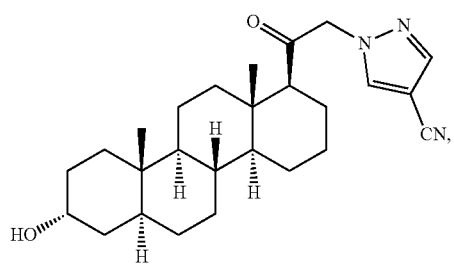

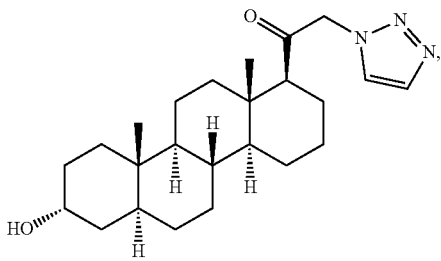

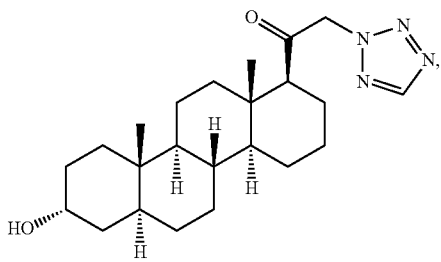

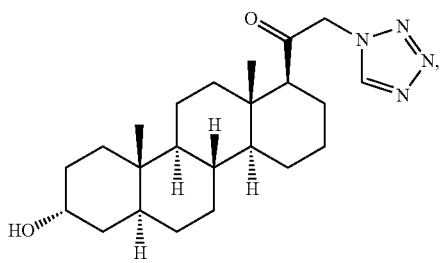

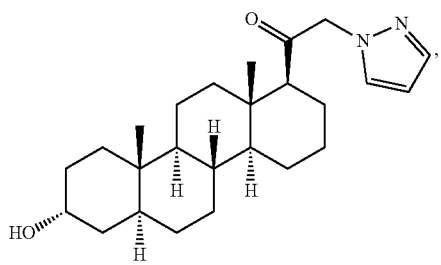

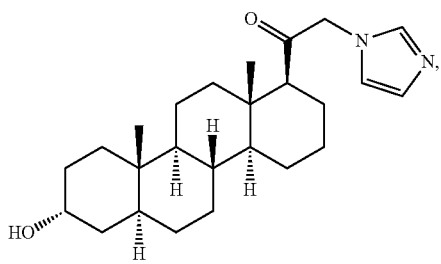

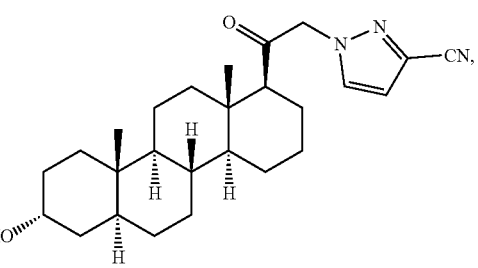

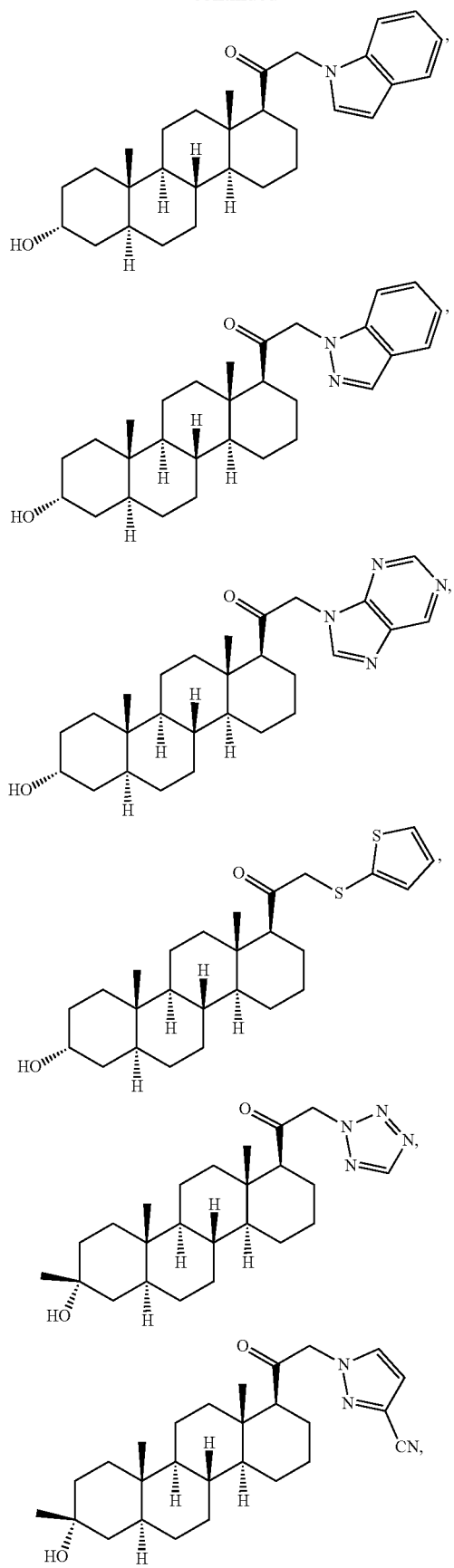
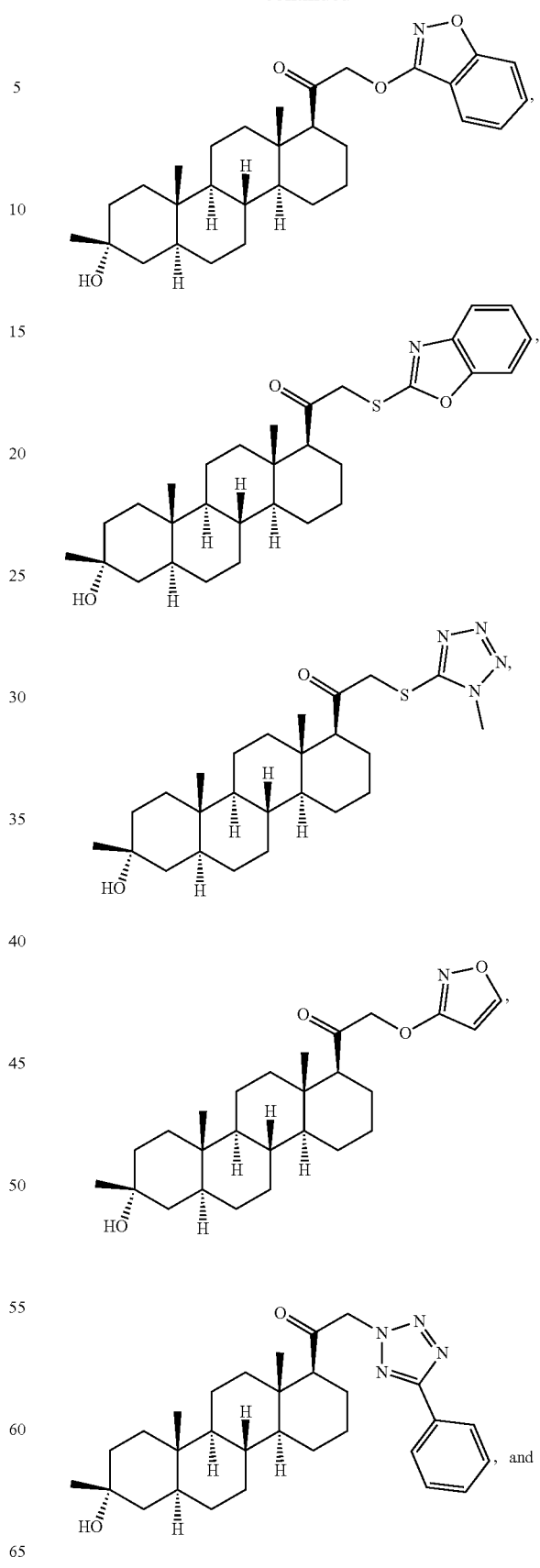

-continued

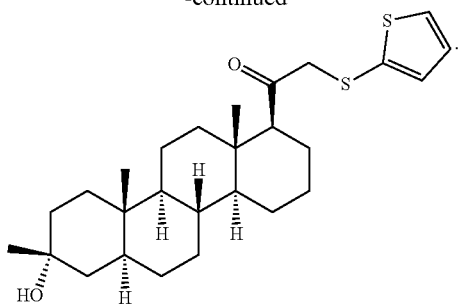

6. A pharmaceutical composition comprising a compound of claim 1, or a pharmaceutically acceptable salt thereof, and a pharmaceutically acceptable excipient.

7. The pharmaceutical composition of claim 6, wherein the pharmaceutical composition is administered orally, subcutaneously, intravenously, or intramuscularly.

8. The compound of claim 4 or a pharmaceutically acceptable salt thereof, wherein X is $CH_2$.

9. The compound of claim 8 or a pharmaceutically acceptable salt thereof, wherein R5 is

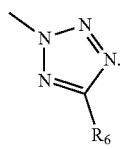

10. The compound of claim 9 or a pharmaceutically acceptable salt thereof, wherein R6 is H.

11. The compound of claim 8 or a pharmaceutically acceptable salt thereof, wherein the compound is

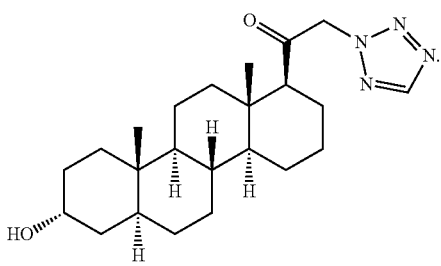

12. The compound of claim 8 or a pharmaceutically acceptable salt thereof, wherein the compound is

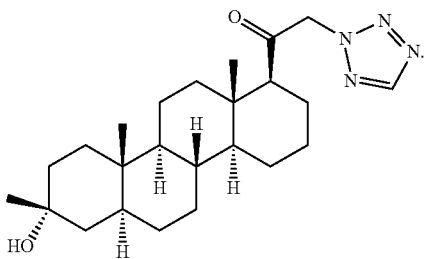

13. A pharmaceutical composition comprising a compound of claim 4, or a pharmaceutically acceptable salt thereof, and a pharmaceutically acceptable excipient.

* * * * *